(12) United States Patent
Ramos Martin et al.

(10) Patent No.: US 9,453,004 B2
(45) Date of Patent: Sep. 27, 2016

(54) FORMYLATED XANTHOCILLIN ANALOGUES AS NEUROPROTECTIVE AGENTS

(71) Applicant: NEURON BIOPHARMA, S.A., Granada (ES)

(72) Inventors: Maria del Carmen Ramos Martin, Granada (ES); Sonia Campoy Garcia, Granada (ES); Javier Santos Burgos Muñoz, Granada (ES); José Luis Adrio Fondevila, Granada (ES); Javier Velasco Alvarez, Granada (ES)

(73) Assignee: NEURON BIOPHARMA, S.A., Granada (ES)

( * ) Notice: Subject to any disclaimer, the term of this patent is extended or adjusted under 35 U.S.C. 154(b) by 0 days.

(21) Appl. No.: 14/377,143

(22) PCT Filed: Feb. 6, 2013

(86) PCT No.: PCT/ES2013/070065
§ 371 (c)(1),
(2) Date: Aug. 6, 2014

(87) PCT Pub. No.: WO2013/117789
PCT Pub. Date: Aug. 15, 2013

(65) Prior Publication Data
US 2015/0011621 A1    Jan. 8, 2015

(30) Foreign Application Priority Data
Feb. 7, 2012   (ES) .................................. 201230174

(51) Int. Cl.
| | | |
|---|---|---|
| C07D 407/06 | (2006.01) |
| C07C 233/03 | (2006.01) |
| C07C 233/22 | (2006.01) |
| A61K 31/165 | (2006.01) |
| A61K 31/36 | (2006.01) |
| A61P 39/06 | (2006.01) |
| A61P 25/28 | (2006.01) |
| A61K 31/137 | (2006.01) |
| C12R 1/82 | (2006.01) |
| C12P 13/02 | (2006.01) |
| C07C 233/25 | (2006.01) |
| C07C 233/18 | (2006.01) |

(52) U.S. Cl.
CPC ........... *C07D 407/06* (2013.01); *A61K 31/137* (2013.01); *C07C 233/03* (2013.01); *C07C 233/18* (2013.01); *C07C 233/22* (2013.01); *C07C 233/25* (2013.01); *C12P 13/02* (2013.01); *C12R 1/82* (2013.01)

(58) Field of Classification Search
CPC . C07D 407/06; C07C 233/03; C07C 232/22; A61K 31/165; A61K 31/36

USPC .......... 514/466, 616; 549/441; 564/155, 158
See application file for complete search history.

(56) References Cited

FOREIGN PATENT DOCUMENTS

| | | |
|---|---|---|
| EP | 2241561 A1 | 10/2010 |
| JP | 2007 191460 A | 8/2007 |

OTHER PUBLICATIONS

Longo et al. NeuroRx 2004, 1, 117-127.*
Mangialasche et al. Lancet Neurology 2010, 9, 702-716.*
Athauda et al. Nature Reviews Neurology 2015, 11, 25-40.*
K. M. Zuck et al.,"Induced Production of N -Formyl Alkaloids from Aspergillus fumigatus by Go-culture with Streptomyces peucetius", J. Nat. Prod., Jul. 22, 2011, vol. 74, No. 7, pp. 1653-1657.
M. Isaka et al., "A Xanthocillin-like Alkaloid from the Insect Pathogenic Fungus Cordyceps brunnearubra BCC 1395", J. Nat. Prod., Apr. 1, 2007, vol. 70, No. 4, pp. 656-658.
K. Tatsuta et al., "The first stereoselective total synthesis of antiviral antibiotic, xanthocillin X dimethylether and its stereoisomer", Tetrahedron Letters, Elsevier, Amsterdam, NL, Jul. 25, 2005, vol. 460, No. 30, , pages.
International Search Report dated Sep. 27, 2013 for PCT/ES2013/070065.
Barcia, E., et al., "Protective effects of clioquinol on human neuronal-like cells: a new formulation of clioquinol-loaded PLGA microspheres for Alzheimer's disease", Journal of Drug Targeting, 2011, pp. 637-646, 19(8).
D'Amelio, Marcello, et al., "Caspase-3 triggers early synaptic dysfunction in a mouse model of Alzheimer's disease", Nature Neuroscience, Jan. 2011, pp. 69-79, 14(1).
Geula, Changiz, et al., "Relationship Between Plaques, Tangles, and Loss of Cortical Cholinergic Fibers in Alzheimer Disease", Journal of Neuropathology and Experimental Neurology, Jan. 1998, pp. 63-75, 57(1).
Gilman, S., MD, FRCP, et al., "Clinical effects of Aβ immunization (AN1792) in patients with AD in an interrupted trial", Neurology, May 2005, pp. 1553-1562, 64.
Green, Robert, et al., "Effect of Tarenflurbil on Cognitive Decline and Activities of Daily Living in Patients With Mild Alzheimer Disease: A Randomized Controlled Trial", National Institutes of Health, Dec. 2009, pp. 2557-2564, 302(23).
Gu, Yaping, et al., "Mutant Prion Protein D202N associated with Familial Prion Disease is Retained in the Endoplasmic Reticulum and Forms 'Curly'Intracellular Aggregates", National Institutes of Health, 2007, pp. 90-96, 32(1).
Lee, Hyun Pil, et al., "Antioxidant approaches for the treatment of Alzheimer's disease", Expert Reviews Neurother, 2010, pp. 1201-1208, 10(7).
Lopes, Fernanda Martins, et al., "Evaluation of the Neurotoxic/Neuroprotective Role of Organoselenides Using Differentiated Human Neuroblastoma SH-SY5Y Cell Line Challenged with 6-Hydroxydopamine", Neurotox Res, 2012, pp. 138-149, 22.

(Continued)

*Primary Examiner* — Sreeni Padmanabhan
*Assistant Examiner* — Irina Neagu
(74) *Attorney, Agent, or Firm* — Knobbe, Martens, Olson & Bear LLP

(57) ABSTRACT

Formylated xanthocillin analogs can be used in the treatment of neurodegenerative diseases. The analogs can be prepared synthetically, and at least some of the analogs can be obtained from a microorganism strain of the *Penicillium chrysogenum* species.

10 Claims, 30 Drawing Sheets

(56) References Cited

OTHER PUBLICATIONS

Maarouf, Chera L., et al., "Alzheimer's Disease and Non-Demented High Pathology Control Nonagenarians: Comparing and Contrasting the Biochemistry of Cognitively Successful Aging", PLoS ONE, Nov. 2011, pp. e27291 1-17, 6(11).

Majima, Hideyuki, J., et al., "Mitochondria as Possible Pharmaceutical Targets for the Effects of Vitamin E and its Homologues in Oxidative Stress-Related Diseases", Current Pharmaceutical Design, Jul. 2011, pp. 2190-2195, 17(21).

Miller, Elzbieta, et al., "Oxidative modification of patient's plasma proteins and its role in pathogenesis of multiple sclerosis", Elsevier: Clinical Biochemistry, 2012, pp. 26-30, 45.

Mirshafiey, Abbas, et al., "Therapeutic approach by Aloe vera in experimental model of multiple sclerosis", Immunopharmacology and Immunotoxicology, Mar. 2010, pp. 410-415, 32(3).

Napolitano, Maddalena, et al., "NF-kB/NOS cross-talk induced by mitochondrial complex II inhibition: Implications for Huntington's disease", Elsevier: Science Direct, 2008, pp. 241-246, 434.

Novoselova, Tatiana V., et al., "Treatment with extracellular HSP70/HSC70 protein can reduce polyglutamine toxicity and aggregation", Journal of Neurochemistry, 2005, pp. 597-606, 94.

Pratico, Domenico MD, et al., "Increase of Brain Oxidative Stress in Mild Cognitive Impairment: A Possible Predictor of Alzheimer Disease", Arch Neurol, Jun. 2002, pp. 972-976, 59.

Richards, Shane A., et al., "The accumulation of un-repairable DNA damage in laminopathy progeria fibroblasts is mused by Ros generation and is prevented by treatment with N-acetyl cysteine", Human Molecular Genetics, Aug. 2011, pp. 3997-4004, 20(20).

Satoh, Jun-Ichi MD, PhD, et al., "The 14-3-3 Protein Forms a Molecular Complex with Heat Shock Protein Hsp60 and Cellular Prion Protein", J Neuropathol Exp Neurol, Oct. 2005, pp. 858-868, 64(10).

Schor, Nina F., MD, PhD., "What the Halted Phase III γ-Secretase Inhibitor Trial May (or May Not) Be Telling Us", American Neurological Association, 2011, pp. 237-239, 69(2).

Stack, Edward C., et al., "Evidence of Oxidant Damage in Huntington's Disease: Translational Strategies Using Antioxidants", Mitochondria and Oxidative Stress in Neurodegenerative Disorders, 2008, pp. 79-92.

Nang, Jing, et al., "Protective effects of resveratrol through the up-regulation of SIRT1 expression in the mutant hS0D1-G93A-bearing motor neuron-like cell culture model of amyotrophic lateral sclerosis", Elsevier: Neuroscience Letters, 2011, pp. 250-255, 503.

Weir, David W., et al., "Development of biomarkers for Huntington's disease" Lancet Neurol, 2011, pp. 573-590, vol. 10.

Yan, Tao, et al. "Altered Levels of Primary Antioxidant Enzymes in Progeria Skin Fibroblasts", Biochemical and Thophysical Research Communications, 1999, pp. 163-167, 257(1).

Zeng, Guang, et al., "Salvianolic Acid B Protects SH-SY5Y Neuroblastoma Cells from 1-Methyl-4-phenylpyridinium-Induced Apoptosis", Biol. Pharm. Bull., 2010, pp. 1337-1342, 33(8).

* cited by examiner

Figure 4

| FET: 48 hours post-treatment | EXTRACT DILUTION | | |
|---|---|---|---|
| ZEBRAFISH EMBRYO TOXICITY | 1/100 | 1/200 | 1/400 |
| Lethal parameters: | | | |
| Coagulated eggs | 0% | 0% | 0% |
| Tail detachment | + | + | + |
| Heart rate: | + | + | + |
| -    Slow heart rate | 0% | 0% | 0% |
| -    Very slow heart rate | 0% | 0% | 0% |
| -    Pericarditis | 0% | 0% | 0% |
| Somite formation | + | + | + |
| Sub-lethal parameters: | | | |
| Spontaneous movements | 100% | 100% | 100% |
| Pigmentation | 100% | 100% | 100% |
| Edema formation | 0% | 0% | 0% |
| Clot formation: | | | |
| -    Clot in head | 0% | 0% | 0% |
| -    Clot in head-eye | 0% | 0% | 0% |
| -    Clot in yolk | 0% | 0% | 0% |
| -    Clot in pericardium | 0% | 0% | 0% |
| -    Clot in tail | 0% | 0% | 0% |
| Teratogenic parameters: | | | |
| Malformations in organs and structures | | | |
| -    General malformation | 0% | 0% | 0% |
| -    Malformation in yolk-tail | 0% | 0% | 0% |
| -    Malformation in yolk | 0% | 0% | 0% |
| -    Malformation at end of tail | 0% | 0% | 0% |
| Scoliosis | 0% | 0% | 0% |
| Rachischisis | 0% | 0% | 0% |
| Growth retardation | 0% | 0% | 0% |
| General toxicological parameters | | | |
| $LC_{50}$ | >1/100 | | |
| NOEC | 1/100 | | |
| LOEC | >1/100 | | |

Figure 5

CccgcgtccgaGCCGAgCGCGTTCCTCGGTCTAGGCAGGTCGCATTGCACCCTCGGCTATAAGACGCC
CCTAGGGGCGTTACCTTCCGAGGGCCTTTGACCGACCGCCCAAACCGACGCTGGCCCGCCCGCGGGGA
AGTACACCGGCACGAATGCCGGCTGAACCCCGCGAGCGAGTCTGGTCGCAAGCGCTTCCCTTTCAACA
ATTTCACGTGCTTTTTAACTCTCTTTTCAAAGTGCTTTTCATCTTTCGATCACTCTACTTGTGCGCTA
TCGGTCTCCGGCCAATATTTAGCTTTAGATGAAATTTACCACCCATTTAGAGCTGCATTCCCAAACAA
CTCGACTCGTCGAAGGAGCTTCACACGGGCGCGGACACCCCATCCCATACGGGATTCTCACCCTCTAT
GACGTCCCGTTCCAGGGCACTTAGATGGGGACCGCTCCCGAAGCATCCTCTACAAATTACAATGCGGA
CCCCGAAgGAGCCaGCTTTCAAATTTGAGCTCTTGCCGCTTCACTCGCcgTTaCtGGGGCAATCCCTG
TTGGTTTCttttcctccgct

Figure 10

| Position | $\delta_C$ | $\delta_H$ (mult. $J$ in Hz) |
|---|---|---|
| 1, 1' | 130.4-131.0 | |
| 2, 2' | 123.3, 122.1, 120.5 | 6.48 (s), 6.48 (s), 6.47 (s), 6.41 (s) |
| 3, 3' | 126.5, 126.2, 126.1 | |
| 4, 4', 8, 8' | 130.4-131.0 | 7.30-7.37 (m) |
| 5, 5', 7, 7' | 115.5, 115.4, 115.3, 115.2 | 6.72-6.76 (m) |
| 6, 6' | 157.5, 157.1, 156.9, 156.7 | |
| 9, 9' | | 9.50 (s), 9.38 (s), 9.30 (d, 11.0), 9.22 (d, 11.4) |
| 10, 10' | 164.5, 160.2 | 8.18 (s), 8.17 (s), 7.85 (d, 11.0), 7.78 (d, 11.4) |
| 6-OH, 6'-OH | | 9.68 (s), 9.66 (s), 9.62 (s), 9.60 (s) |

Figure 14

| Position | $\delta_C$ | $\delta_H$ (mult. $J$ in Hz) |
|---|---|---|
| 1 | 129.5-131.1 | |
| 2 | 120.3-123.6 | 6.46 (s), 6.46 (s), 6.43 (s), 6.39 (s) |
| 3 | 126.5-126.9 | |
| 4 | 115.8-116.6 | 7.02 (d, 2.0), 7.00 (d, 2.0), 6.94 (d, 2.0), 6.92 (d, 2.0) |
| 5 | 144.9-145.3 | |
| 6 | 145.1-145.6 | |
| 7 | 115.3-115.8 | 6.70 (m) |
| 8 | 121.3-121.6 | 6.76-6.82 (m) |
| 9[a] | | 8.19 (s), 9.18 (s), 7.84 (d, 11.1), 7.77 (d, 11.1) |
| 10[a] | 164.6, 160.3 | 9.48 (s), 9.36 (s), 9.30 (d, 11.1), 9.22 (d, 11.1) |
| 5-OH[c] | | 9.20 (s), 9.16 (s), 9.13 (s), 9.10 (s) |
| 6-OH[c] | | 9.02 (s), 8.97 (s), 8.97 (s), 8.92 (s) |
| 1' | 130.4-130.8 | |
| 2' | 120.6-123.1 | 6.39 (s), 6.38 (s), 6.36 (s), 6.32 (s) |
| 3' | 126.1-126.5 | |
| 4', 8' | 130.7, 130.6, 130.5, 130.4 | 7.30-7.38 (m) |
| 5', 7' | 115.3-115.7 | |
| 6' | 156.7-157.2 | 6.72-6.76 (m) |
| 9'[a] | | 8.18 (s), 8.17 (s), 7.86 (d, 11.3), 7.79 (d, 11.2) |
| 10'[a] | 164.6, 160.3 | 9.48 (s), 9.35 (s), 9.26 (d, 11.3), 9.17 (d, 11.2) |
| 6'-OH | | 9.68 (s), 9.66 (s), 9.62 (s), 9.60 (s) |

[a,b,c] Interchangeable assignments

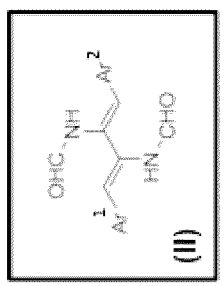
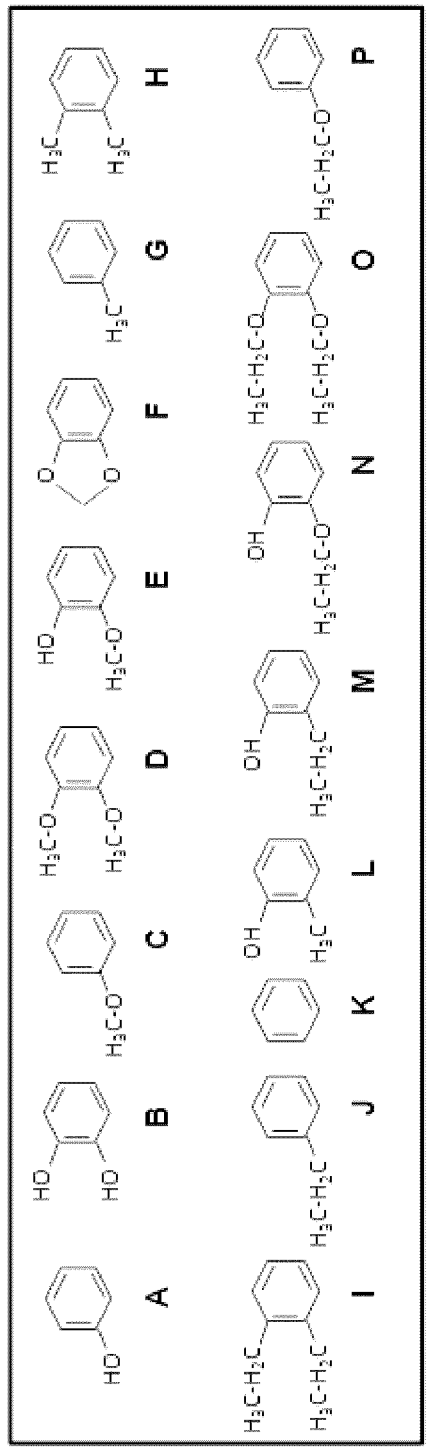
Figure 22

Figure 23

| Air1/Air2 | A | B | C | D | E | F | G | H | I | J | K | L | M | N | O | P |
|---|---|---|---|---|---|---|---|---|---|---|---|---|---|---|---|---|
| A | 3.71 | - | - | - | - | - | - | - | - | - | - | - | - | - | - | - |
| B | 3.41 | 5.61 | - | - | - | - | - | - | - | - | - | - | - | - | - | - |
| C | 3.90 | 3.60 | 4.09 | - | - | - | - | - | - | - | - | - | - | - | - | - |
| D | 3.79 | 3.50 | 6.49 | 3.88 | - | - | - | - | - | - | - | - | - | - | - | - |
| E | 6.10 | 5.80 | 6.30 | 6.19 | 6.00 | - | - | - | - | - | - | - | - | - | - | - |
| F | 6.61 | 6.31 | 6.80 | 6.70 | 6.50 | 7.01 | - | - | - | - | - | - | - | - | - | - |
| G | 6.82 | 6.52 | 7.02 | 6.91 | 6.72 | 7.22 | 7.44 | - | - | - | - | - | - | - | - | - |
| H | 7.14 | 6.84 | 7.33 | 7.23 | 7.03 | 7.55 | 7.75 | 8.07 | - | - | - | - | - | - | - | - |
| I | 7.85 | 7.55 | 8.05 | 7.94 | 7.75 | 8.25 | 8.46 | 8.78 | 7.49 | - | - | - | - | - | - | - |
| J | 7.18 | 6.88 | 7.37 | 7.27 | 7.07 | 7.58 | 7.79 | 8.11 | 8.82 | 8.15 | - | - | - | - | - | - |
| K | 4.00 | 3.71 | 4.20 | 6.60 | 6.40 | 6.91 | 7.12 | 7.44 | 8.15 | 7.48 | 4.30 | - | - | - | - | - |
| L | 6.52 | 6.22 | 6.72 | 6.61 | 6.42 | 6.92 | 7.14 | 7.45 | 8.17 | 7.49 | 6.82 | 6.84 | - | - | - | - |
| M | 6.88 | 6.58 | 7.07 | 7.00 | 6.78 | 7.28 | 7.49 | 7.81 | 8.52 | 7.85 | 7.18 | 7.55 | 7.55 | - | - | - |
| N | 6.54 | 6.24 | 6.73 | 6.63 | 6.43 | 6.94 | 7.15 | 7.47 | 8.18 | 7.51 | 6.84 | 6.85 | 7.21 | 6.87 | - | - |
| O | 7.17 | 6.87 | 7.36 | 7.26 | 7.06 | 7.57 | 7.78 | 8.10 | 8.81 | 8.14 | 7.47 | 7.48 | 7.84 | 7.50 | 8.13 | - |
| P | 6.84 | 6.54 | 7.03 | 6.93 | 6.73 | 7.24 | 7.45 | 7.77 | 8.48 | 7.81 | 7.14 | 7.15 | 7.51 | 7.17 | 7.80 | 7.47 | ns.

FORMYLATED XANTHOCILLIN ANALOGUES AS NEUROPROTECTIVE AGENTS

CROSS REFERENCE TO RELATED APPLICATIONS

This application is the U.S. National Phase of International Application No. PCT/ES2013/070065, filed Feb. 6, 2013, designating the U.S. and published in Spanish as WO 2013/117789 on Aug. 15, 2013 which claims the benefit of Spain Patent Application No. P201230174 filed Feb. 7, 2012.

REFERENCE TO SEQUENCE LISTING

The present application incorporates by reference the sequence listing submitted as an ASCII text filed via EFS-Web. The Sequence Listing is provided as a file entitled SEQ.txt, created on Aug. 5, 2014, which is 1.59 Kb in size.

FIELD OF THE INVENTION

The invention relates to the use of formylated xanthocillin analogues and of their derivatives for the treatment of neurodegenerative diseases, cognitive deficits, dementias and especially Alzheimer's disease.

BACKGROUND OF THE INVENTION

Alzheimer's disease (AD) is the most common cause of dementia. According to the WHO, in the year 2006 the number of people suffering dementia amounted to 37 million worldwide, 18 million of which were Alzheimer's patients. In this sense, the number of patients is expected to double in the next 25 years, reaching 34 million in 2025. In Spain alone it is estimated that over half a million people currently suffer AD (Mount & Downtown, Nat Med 2006; 12[7]: 780-4).

The costs associated with this disease are proportionally high. In 2005, health costs for Alzheimer's disease and other dementias in the 27 countries forming the European Union were estimated to be in 130,000 million Euros, about 21,000 Euros per patient and year. The total cost derived from caring for Alzheimer's patients in the United States in 2005 was calculated to be 91,000 million dollars, detecting an increase in medical expenses associated with the disease, which exceeded 160,000 million dollars in 2010 (Mount & Downtown, Nat Med 2006; 12[7]: 780-4).

Based on the foregoing reasons, AD and diseases associated with aging such as cognitive deficits or dementias have become a major problem worldwide. However, there are no efficient drugs that prevent or impede neurodegenerative diseases (ND), therefore the search for and validation of new neuroprotective compounds preventing neuronal damage have become a necessity, especially taking into account that the pathophysiological mechanisms thereof have yet to be clarified. Neurodegenerative pathologies are a consequence of neuronal death and of the subsequent loss of brain mass, a consequence of the absence of neurons in specific areas of the brain. For this reason, one of the valid strategies for the treatment and/or prevention of ND is the search for drugs impeding neuronal death, i.e., they are neuroprotective drugs. However, the drugs used until now for AD have been symptomatic, and do not prevent disease progression or onset. Until now there have been two types of drugs on the market: acetylcholinesterase (AChE) inhibitors and memantine, an NMDA (N-methyl-D-aspartic acid) glutamatergic receptor inhibitor. Current therapeutic options for AD are based on inhibiting acetylcholinesterase with drugs such as donepezil, galantamine or rivastigmine, or on the capacity of memantine to antagonize the NMDA receptor. Nevertheless, it has been proven that the use of rivastigmine does not stop or slow down the progression of mild cognitive impairment (MCI) or of AD (Feldman et al. Lancet Neurol 2007; 6[6]: 501-12), whereas the use of donepezil only shows modest short-term benefits, but with the drawback of presenting significant side effects (Birks and Flicker, Cochrane Database Syst Rev 2006; 3: CD006104). According to the American Alzheimer's Association, the emergence of drugs that delay disease onset by only 5 years would save 50,000 million dollars in the United States alone. In this sense, the use of preventive strategies, such as intervention in mild cognitive impairment (MCI) processes would be a valid alternative.

MCI, also known as incipient dementia or isolated memory impairment, is one of the prior stages associated with AD and other dementias. MCI is recognized as a risk factor of AD; it affects about 30 million people worldwide and is considered a first step towards AD, where between 10 and 15% of individuals with MCI progress to AD each year (Grundman et al. Arch. Neurol 2004; 61[1]: 59-66). Despite the significant prevalence of MCI and of the high likelihood of patients to progress to a dementias, there is currently no treatment or therapy for this clinical condition, whereby the use of antioxidants or anti-AD drugs is recommended for the treatment of MCI. So there are currently no drugs for treating MCI, and current anti-AD drugs offer few benefits to patients which temporarily delay (by one year in a best-case scenario) some symptoms of the disease but do not prevent their progression.

Due to the very limited success of drugs against NDs, new lines of research have opened up. Search strategies for finding for new chemical entities (NCE) based on natural biodiversity stand out among them. In fact, the search for bioactive compounds against different pathologies is one of the central themes of natural product chemistry. Massive search strategies for finding compounds and extracts based on different biological sources, among which microorganisms can be found, have recently started to be applied. The search for active biomolecules therefore requires the isolation and culture of microorganisms that produce compounds from different environments. In fact, more 20,000 of the 250,000 bioactive metabolites that are calculated to exist are produced by microorganisms. Filamentous fungi, single-cell bacteria and actinomycetes are the most prolific groups when it comes to producing such compounds. Approximately only 1% of these compounds, about 160, are used directly in human and animal medicine and in agriculture. This ratio (0.2-0.3%) is, however, much higher than that attained by the pharmaceutical industry by means of new chemical entities obtained by synthesis (0.001%). Between the years of 2005 and 2007 alone, 19% of the drugs launched on the market were natural products or products derived from natural products. The chemical variety of these metabolites is enormous because it depends on the microorganism, on the composition of the culture medium and on the conditions under which said culture is performed.

In this sense, formylated xanthocillin analogues with a single substituent in each aromatic ring obtained by mixed fermentation of *A. fumigatus* with *S. peucetis* have been described (Zuck et al., J. Nat. Prod. 2011, 74, 1653-1657), which demonstrated antitumor activity using the 60 NCI-60 cell line panel. Two of these compounds showed activity against some cell lines (of lung cancer, central nervous system cancer, melanoma, ovarian cancer, renal cancer and leukemia), whereas the remaining compounds were inactive. The activity of one of the two compounds against *Escherichia coli*, *Candida albicans*, *Staphylococcus aureus*, *Burkholderia thailandesis* and *Fusarium pallidoroseum* was evaluated, but no activity was shown in said assays.

It has also been proven that the formylated xanthocillin analogue isolated from *Cordyceps brunnearubra* BCC 1395, as well as the hexamethylated and hexaacetylated compounds obtained by methylation and acetylation, show activity against the malaria parasite *Plasmodium falciparum*, cytotoxicity against breast cancer cells, while lacking activity against human oral epidermoid carcinoma and lung cancer cells and non-cancerous Vero cells (Isaka et al., J. Nat. Prod. 2007, 70, 656-658).

Nevertheless, neuroprotective activity has not been proven for any of these compounds isolated from the mentioned microorganisms.

BRIEF DESCRIPTION OF THE INVENTION

The authors of the present invention have identified a series of compounds that correspond with formylated xanthocillin analogues, obtained from an extract produced by a strain of the *Penicillium chrysogenum* species, which have proven a surprising neuroprotective effect against neuronal death caused by oxidative damage, which gives them excellent properties as neuroprotective compounds.

Furthermore, the analysis of the in vitro antioxidant capacity of these compounds has surprisingly found that these compounds are antioxidants.

It has also been proven that these compounds protect against apoptosis caused by modifications of the amyloid precursor protein (APP) in two cell models carrying the wild-type and Swedish mutant variants of said protein, which is related to Alzheimer's disease.

The obtained experimental results clearly show the potential use of formylated xanthocillin analogues in the prevention and/or treatment of neuronal death associated with neurodegenerative diseases, cognitive deficits, dementias, diseases associated with aging, pathological processes associated with age and progeria.

The obtained results can be extrapolated for prophylactic or therapeutic purposes for their application to the risk population.

Therefore, a first aspect of the present invention is a compound of formula (I):

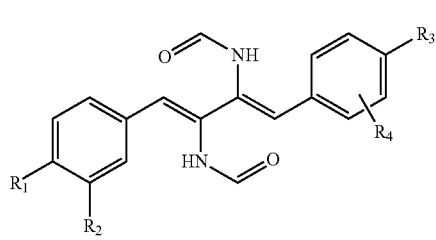

where:
$R_1$ is selected from alkyl, OH, O-alkyl, SH, S-alkyl, $NH_2$, NH-alkyl, $N(alkyl)_2$ and halogen,
$R_2$, $R_3$ and $R_4$ are selected independently from hydrogen, alkyl, OH, O-alkyl, SH, S-alkyl, $NH_2$, NH-alkyl, $N(alkyl)_2$ and halogen, or $R_1$ and $R_2$ and/or $R_3$ and $R_4$ form an —O-alkylene-O— group, or a pharmaceutically acceptable salt, solvate or prodrug thereof, for use in the prevention and/or treatment of neurodegenerative diseases.

In a second aspect, the invention relates to compounds of formula (II):

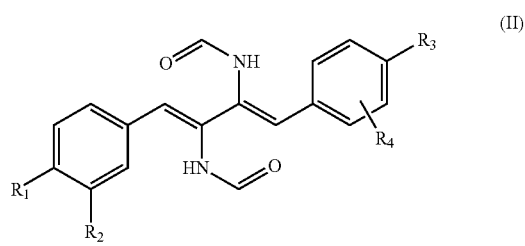

where
$R_1$ is selected from alkyl, OH, O-alkyl, SH, S-alkyl, $NH_2$, NH-alkyl, $N(alkyl)_2$ and halogen,
$R_2$, $R_3$ and $R_4$ are selected independently from hydrogen, alkyl, OH, O-alkyl, SH, S-alkyl, $NH_2$, NH-alkyl, $N(alkyl)_2$ and halogen, or $R_1$ and $R_2$ and/or $R_3$ and $R_4$ form an —O-alkylene-O— group, or a pharmaceutically acceptable salt, solvate or prodrug thereof, with the proviso that formula (II) does not include:
  the compound in which $R_1$-$R_4$ are OH and $R_4$ is in the meta position of the aromatic ring;
  the compound in which $R_1$-$R_4$ are $OCH_3$ and the $R_4$ substituent is in the meta position of the aromatic ring;
  compounds in which $R_2$ and $R_4$ are hydrogen and $R_1$ and $R_3$ are selected independently from OH and methoxy.

In a third aspect, the invention relates to a pharmaceutical formulation comprising a compound of formula (II) and a pharmaceutically acceptable vehicle.

The invention also relates to a compound of formula (II) for use in medicine.

The invention additionally relates to a method for the preparation of a compound of formula (II) from an extract produced by the *Penicillium chrysogenum* species.

The invention also relates to a method for the preparation of a compound of formula (II) comprising:
  a) a condensation reaction whereby the aryl propionic acid ester of formula (III) is converted into its corresponding amide of formula (IV):

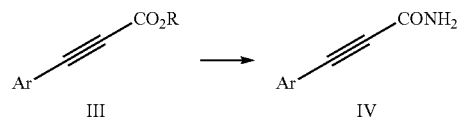

where R represents an alkyl group;
  b) reacting the amide of formula (IV) with an alkyl tin hydride to produce the stannane of formula (V):

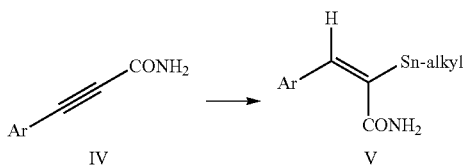

and,
then subjecting the compound of formula (V) to a reaction sequence comprising:
c.1) Baumgarten oxidation reaction to provide the protected carbamate of formula (VI):

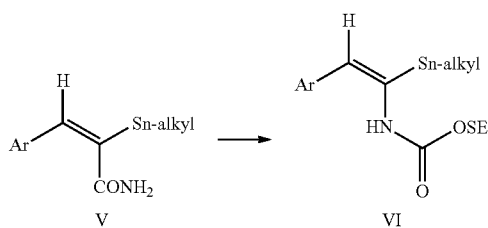

where SE means a protecting group;
d.1) subjecting the carbamate of formula (VI) to a homo-coupling reaction to give the compound of formula (VII):

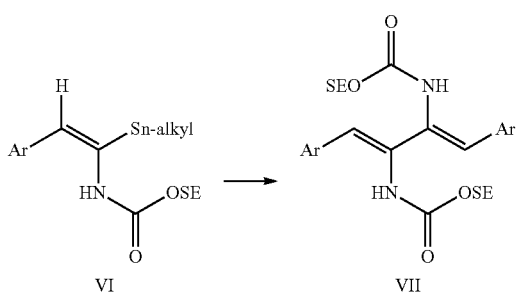

and
e.1) deprotecting the carbamate groups and introducing the formamido groups to obtain the compound of formula (II) of the invention;
or
subjecting the compound of formula (V) to a reaction sequence comprising:
c.2) Baumgarten oxidation reaction to provide the protected carbamate of formula (VI):

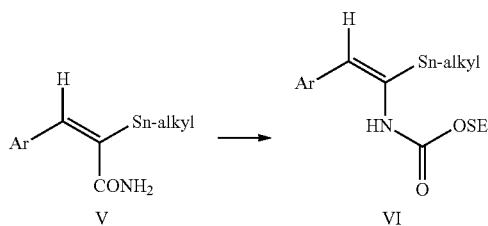

d.2) deprotecting the carbamate groups and introducing the formamido groups to obtain the compound of formula (VIII):

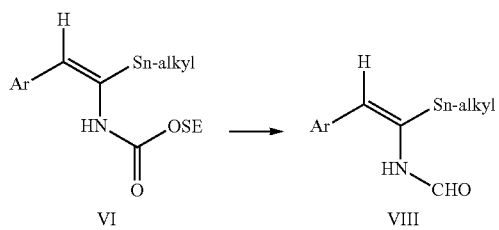

and
e.2) subjecting the formamide of formula (VIII) to a homo-coupling reaction to provide the compound of formula (II) of the invention;
or
subjecting the compound of formula (V) to a reaction sequence comprising:
c.3) Baumgarten oxidation reaction to provide the isocyanate of formula (IX):

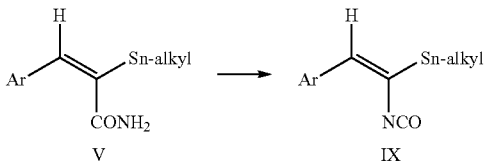

d.3) converting the isocyanate of formula (IX) into the formamide of formula (VIII):

and
e.3) subjecting the formamide of formula (VIII) to a homo-coupling reaction to provide the compound of formula (II) of the invention;
where the aryl group (Ar) includes the $R_1$ to $R_4$ substituents depending on the compound of formula (II) that is to be obtained.

Finally, the invention relates to a microorganism strain of the *Penicillium chrysogenum* species deposited in the CECT (Spanish Type Culture Collection) with accession number CECT 20783.

BRIEF DESCRIPTION OF THE DRAWINGS

FIG. 4 is a listing of the lethal, sub-lethal, teratogenic and toxicological parameters observed at 48 hours post-treatment in zebrafish embryos exposed to extract 08_055 C08 at 1/100, 1/200 and 1/400 dilutions.

FIG. 5 is the sequencing of the fragment obtained by strain 0882-08 28S gene PCR.

FIG. 10 shows the chemical shifts of $^1H$ (500 MHz) and $^{13}C$ (125 MHz) for compound NPS0156 in DMSO-d6.

FIG. 14 shows the chemical shifts of $^1H$ (500 MHz) and $^{13}C$ (125 MHz) for compound NPS0155 in DMSO-d6.

FIG. 22 shows the nature of groups A to P representing $Ar^1$ and $Ar^2$ in the schematic structure in (II), which defines a family of xanthocillin derivatives.

FIG. 23 is a matrix showing the value of C LOG P, defined as log P of a compound, which is the partition coefficient between n-octanol and water, $log(c_{octanol}/c_{water})$, of the different combinations of substituents of the molecule of formula (II).

FIGS. 25-28 correspond respectively to the results of analogues NPS0158 (G+G), NPS0159 (F+F), NPS0160 (P+P) and NPS0161 (H+H). The results are the mean±SD of 2-3 assays performed in duplicate. * Significant difference with respect to treatment with XXO according to the Student's t test ($p<0.05$).

DETAILED DESCRIPTION OF THE INVENTION

Definitions

Figure 1:
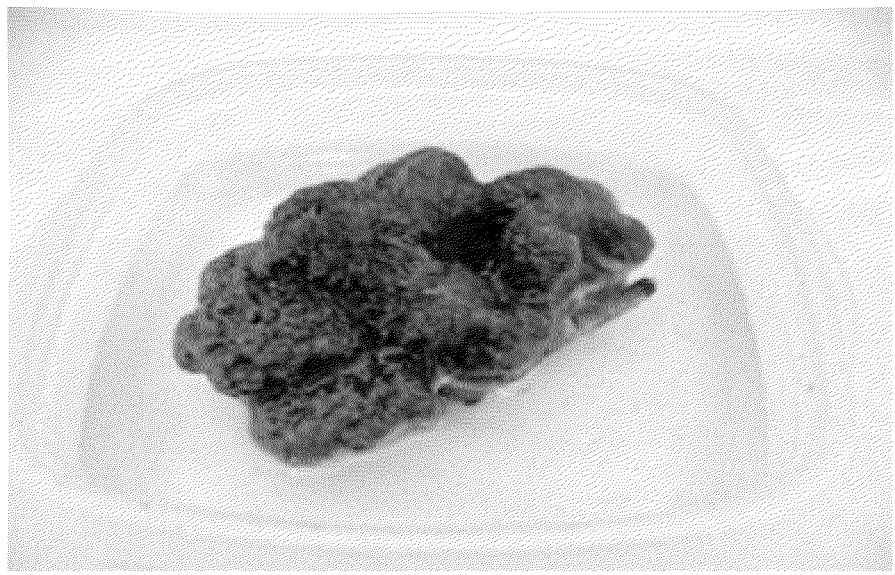
FIG. 1 is a photograph of sample M082-08, which is from a marine sponge collected in Cabo de Gata (Almeria).

To aid in understanding the invention object of this patent application, the meaning of some terms and expressions used in the context of the invention is explained below.

As it is used herein, a "neurotoxic substance" refers to chemical substances that produce functional, structural and biochemical alterations of the central nervous system. These adverse effects involve changes that produce a deregulation or alteration of the nervous system. The nature of said change can be neurochemical, morphological, or behavioral-related and can temporarily or permanently present itself.

As it is used herein, the term "neurodegenerative disease" includes diseases which result from the degeneration or deterioration of nervous tissue, particularly of neurons, leading over time to a dysfunction or to a disability; the term degeneration includes loss of cell viability, loss of the cell function and/or loss of the number of cells (neurons and others). Illustrative, non-limiting examples of neurodegenerative diseases include Alzheimer's disease, mild cognitive impairment, Huntington's disease, Parkinson's disease, Creutzfeldt-Jakob disease, Alexander disease, cognitive and/or psychomotor deficits, ataxias, dementias, cerebrovascular diseases, amyotrophic lateral sclerosis (ALS), multiple sclerosis (MS), as well as diseases associated with aging, pathological processes associated with age and progeria. In a particular embodiment, said neurodegenerative disease is a disease related to neuronal death caused by a neurotoxic substance, for example, a substance that produces endoplasmic reticulum stress, apoptosis, cytoskeleton disorganization, degeneration of the basal ganglia or mitochondrial damage.

As they are used herein, the terms "neuroprotection" and "neuroprotective", refer to the attenuation of the effects of neuronal death or degeneration by means of any known mechanism or to be known, for example, necrosis, apoptosis, autophagy, excitotoxicity, oxidative damage, mitochondrial damage, endoplasmic reticulum damage, deposition of byproducts, loss of the cell architecture, etc., or to the disappearance of the effects of neuronal death or degeneration by means of any mechanism known or to be known, for example, necrosis, apoptosis, autophagy, excitotoxicity, oxidative damage, mitochondrial damage, endoplasmic reticulum damage, deposition of byproducts, loss of cell architecture, etc., or to the reduction or disappearance of the side effects thereof.

As it is used herein, the term "subject" refers to a member of a mammal species, and includes but is not limited to domestic animals, primates and humans; preferably, the subject is a male or female human of any age or race. In a particular embodiment, said subject is a mammal that suffers, or is susceptible to suffering, a neurodegenerative disease, such as a chronic neurodegenerative disease or a disease associated with aging.

The term "salt" must be understood to mean any form of xanthocillin derivatives in which the compound takes on an ionic form, or is charged and coupled to a counterion (a cation or anion) or are in a solution. For this reason, it must also be understood as complexes of the active compound with other molecules and ions, and particularly complexes that are complexed through ionic interactions.

The term "solvate" according to this invention must be understood to mean any form of the xanthocillin derivative of formula (I) which has another molecule bound thereto (most likely a solvent) through a non-covalent bond. Examples of solvates include hydrates and alcoholates, for example methanolate. Preferably, the solvates are pharmaceutically acceptable solvates.

The term "prodrug" is used in its broadest meaning and encompasses those derivatives which are converted in vivo into the compounds of the invention. The persons skilled in the art would easily produce such derivatives, and include, depending on the functional groups present in the molecule, and without limitation, the following derivatives of the present compounds: esters, amino acid esters, phosphate esters, carbamates, amides, etc. Examples of well-known methods for producing a prodrug of a compound having a given action are known by those persons skilled in the art and can be found, for example, in Krogsgaard-Larsen et al., "Textbook of Drug Design and Discovery" Taylor & Francis (April 2002). Particularly favorable prodrugs or derivatives are those which increase the bioavailability of the compounds of this invention when such compounds are administered to a patient (for example, allowing a compound administered by oral route to be more easily absorbed in the blood) or those which increase the administration of the original compound to a biological compartment (for example, the brain or lymphatic system) in relation to the original species.

The expression "pharmaceutically acceptable" refers to molecular entities and compositions which are physiologically tolerable and usually do not produce allergic reactions or similar unfavorable reactions such as gastric disorders, dizziness, and reactions of the same class, when they are administered in humans or animals.

The expression "pharmaceutically acceptable" means that it is approved by a regulatory agency of a state or federal government or is included in the US Pharmacopoeia or another pharmacopoeia generally recognized for use in animals, and more particularly in human beings.

The term "alkyl" refers to a linear or branched hydrocarbon chain that consists of carbon and hydrogen atoms, does not contain unsaturations, and has from one to twelve carbon atoms, preferably from one to eight carbon atoms, more preferably from one to six carbon atoms, and is bound to the rest of the molecule through a single bond. Examples of alkyl groups include but are not limited to methyl, ethyl, n-propyl, isopropyl, n-butyl, tert-butyl and hexyl.

The term "halogen" includes fluorine, chlorine, bromine or iodine.

The term "alkylene" in the "O-alkylene-O" substituent refers to a linear or branched hydrocarbon chain which consists of carbon and hydrogen atoms, does not contain unsaturations, and has from one to twelve carbon atoms, preferably from one to eight carbon atoms, more preferably from one to six carbon atoms, and is bound to the oxygen atoms through a single bond. Examples of the "O-alkylene-O" substituent include O-methylene-O (O—$CH_2$—O), O-ethylene-O (O—$CH_2$—$CH_2$O), O-propylene-O (O—$CH_2$—$CH_2$—$CH_2$O) or O-butylene-O (O—$CH_2$—$CH_2$—$CH_2$—$CH_2$O).

In a first aspect, the present invention relates to a compound of formula (I) as defined above, or to a pharmaceutically acceptable salt, prodrug or solvate for use in the prevention and/or treatment of neurodegenerative diseases.

In a particular embodiment, $R_1$ is selected from alkyl, OH and O-alkyl, or $R_1$ is bound to $R_2$ forming an —O-alkylene-O group.

In another particular embodiment, $R_2$, $R_3$ and $R_4$ are selected independently from hydrogen, alkyl, OH and O-alkyl, or $R_2$ is bound to $R_1$ forming an —O-alkylene-O group, and/or $R_3$ and $R_4$ are bound to one another forming an —O-alkylene-O group.

Preferably, $R_4$ is in the meta position of the aromatic ring.

Also preferably, $R_1$ is OH, alkyl or forms, together with $R_2$, an —O-alkylene-O group. More preferably, $R_1$ is OH, methoxy, ethoxy, ethyl, methyl or forms, together with $R_2$, an —O-alkylene-O group.

Also preferably, $R_2$ is hydrogen, OH, alkyl or forms, together with $R_1$, an —O-alkylene-O group. More preferably, $R_2$ is hydrogen, OH, ethyl, methyl or forms, together with $R_1$, an —O-alkylene-O group.

Also preferably, $R_3$ is OH, alkyl or forms, together with $R_4$, an —O-alkylene-O group. More preferably, $R_3$ is OH, ethyl, methyl or forms, together with $R_4$, an —O-alkylene-O group.

Also preferably, $R_4$ is hydrogen, OH, alkyl or forms, together with $R_3$, an —O-alkylene-O group. More preferably, $R_4$ is hydrogen, OH, ethyl, methyl or forms, together with $R_3$, an —O-alkylene-O group.

In an even more preferred embodiment, the compound of formula (I) is selected from the following compounds:

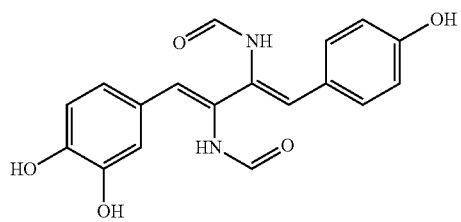

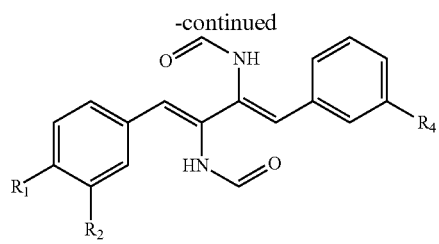

$R_1 = R_2 = R_4 = $ Me, Et

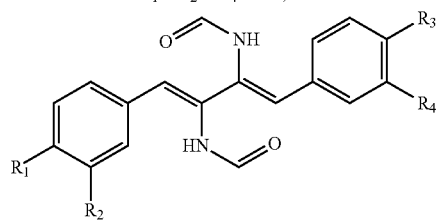

$R_1 = R_2 = R_3 = R_4 = $ Me, Et

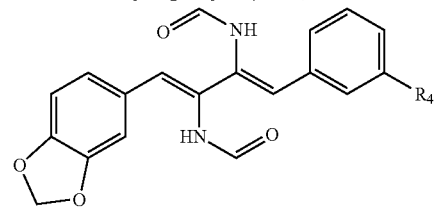

$R_4 = $ OH, Me, Et

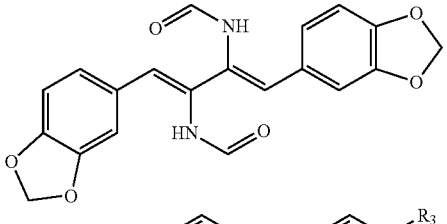

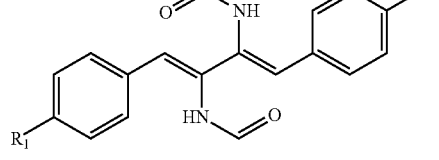

$R_1 = R_3 = $ OH, Me, Et, OEt

The results of the research conducted by the inventors prove that the prevention and/or treatment of neurodegenerative diseases, mild cognitive impairment, cognitive deficits, dementias, diseases associated with aging and/or pathological processes associated with age and progeria with the xanthocillin analogues described in the present invention, occurs, at least partially, by means of neuroprotection, particularly by means of the direct inhibition of neuronal death, i.e., by means of inhibiting the death of the neuronal cells of the nervous system. Therefore, this mechanism of action would occur without the participation of the immune system.

A number of assays performed by the inventors have clearly shown both the neuroprotective effect of extracts rich in xanthocillin derivatives, and of xanthocillin analogues, against the action of different neurotoxic substances, and the antiapoptotic effect thereof in human cholinergic neurons.

In a particular embodiment, the neurodegenerative diseases are selected from Alzheimer's disease, mild cognitive impairment, Huntington's disease, Parkinson's disease, Creutzfeldt-Jakob disease, Alexander disease, cognitive and/ or psychomotor deficits, ataxias, dementias, cerebrovascular diseases, amyotrophic lateral sclerosis (ALS), multiple sclerosis (MS), as well as diseases associated with aging, pathological processes associated with age and progeria. Preferably, said neurodegenerative disease is Alzheimer's disease.

The compounds of formula (I) can be in the form of salts, preferably pharmaceutically acceptable salts, in the form of solvates, preferably pharmaceutically acceptable solvates, or in the form of prodrugs. When said pharmaceutically acceptable salts, solvates or prodrugs of the compound of formula (I) are administered to the receptor, they can provide (directly or indirectly) a compound of formula (I) such as the compound described herein. Pharmaceutically unacceptable salts are also within the scope of the invention because they can be useful for preparing pharmaceutically acceptable salts.

The preparation of salts and solvates can be carried out by means of methods known in the art. For example, the pharmaceutically acceptable salts of compounds provided herein are synthesized from the original compound, which contains one or more basic residues, by means of conventional chemical methods. Such salts are generally prepared, for example, by reacting the free base forms of these compounds with the suitable base or acid in water or in an organic solvent or in a mixture thereof. Non-aqueous media such as ether, ethyl acetate, ethanol, isopropanol or acetonitrile, are generally preferred. Examples of the acid addition salts include inorganic acid addition salts such as, for example, hydrochloride, hydrobromide, hydroiodide, sulfate, nitrate, phosphate, etc., and organic acid addition salts such as, for example, acetate, maleate, fumarate, citrate, oxalate, succinate, tartrate, malate, mandelate, methanesulfonate, p-toluenesulfonate, etc.

A preferred pharmaceutically acceptable form is the crystalline form, including such form in a pharmaceutical composition. In the case of salts and solvates, the additional ionic and solvent residues must also be non-toxic. The compounds of the invention can have different polymorphic forms; the invention seeks to encompass all these forms.

Any compound which is a prodrug of a compound of formula (I) is within the scope of the invention.

The compounds of the invention also seek to include compounds which differ only in the presence of one or more isotopically enriched atoms. For example, compounds having the present structures, except for the substitution of a hydrogen with a deuterium or tritium, or the substitution of a carbon with a $^{13}$C- or $^{14}$C-enriched carbon, or a $^{15}$N-enriched nitrogen, are within the scope of this invention.

The compounds of the present invention represented by formula (I) described above can include isomers, such as enantiomers or diastereoisomers, depending on the presence of chiral centers. The unique isomers, enantiomers or diastereoisomers and mixtures thereof are within the scope of the present invention.

For administration in the prevention and/or treatment of neurodegenerative diseases, the xanthocillin analogues of formula (I) can be formulated in a pharmaceutical composition, in a therapeutically effective amount, together with one or more pharmaceutically acceptable vehicles or excipients.

Said pharmaceutical composition can contain one or several xanthocillin analogues of formula (I) or one or more different drugs, together with one or more pharmaceutically acceptable vehicles or excipients. In a particular embodiment, said pharmaceutical composition comprises only one xanthocillin derivative of formula (I). Said pharmaceutical composition is useful for the treatment of neurodegenerative diseases.

The pharmaceutical compositions comprising the xanthocillin analogues of formula (I) can be formulated in any pharmaceutical dosage form suitable for administration by the chosen route of administration. By way of non-limiting example, the pharmaceutical compositions can be formulated in a solid dosage form for administration by oral route (e.g., granules, tablets, capsules, etc.), in a liquid dosage form for administration by oral route (e.g., solutions, suspensions, emulsions, etc.), in a dosage form for administration by parenteral route (e.g., solutions, suspensions, emulsions, etc.). To that end, in each case, the suitable pharmaceutically acceptable vehicles and excipients will be chosen for the chosen pharmaceutical dosage form and route of administration, for example, binding agents, diluents, disintegrating agents, lubricants, wetting agents, etc., for the formulation of solid pharmaceutical dosage forms, and buffers, surfactants, etc., for the formulation of liquid pharmaceutical dosage forms. Said vehicles and excipients must be pharmaceutically acceptable and pharmacologically tolerable and have to be able to be combined with other components of the formulation without exerting any adverse effect on the treated subject. Information about said vehicles and excipients, as well as about said pharmaceutical dosage forms of said active ingredient can be found in Galenic pharmacy treatises. A review of the different pharmaceutical dosage forms of drugs, in general, and of their methods of preparation can be found in the book "Tratado de Farmacia Galénica", by C. Faulí i Trillo, 1$^{st}$ Edition, 1993, Luzán 5, S. A. de Ediciones.

The pharmaceutical composition used in the present invention comprises at least one xanthocillin analogue of formula (I) in a therapeutically effective amount. In the sense used herein, the expression "therapeutically effective amount" refers to the amount of drug calculated to produce the desired effect. The drug dose to be administered to a subject can vary within a wide range depending on a number of factors, among which the characteristics of the drug used, e.g., biological half-life and activity, the concentration of the compound in the pharmaceutical composition, the clinical situation of the subject, the severity of the pathology, the chosen pharmaceutical dosage form, etc., are included. The pharmaceutical composition provided by this invention can be administered once or more times a day for preventive or therapeutic purposes or with other administration regimens which are not necessarily daily but also at precise times, weekly, etc.

In an additional aspect, the present invention relates to the use of a compound of formula (I), or a pharmaceutically acceptable salt, prodrug or solvate thereof, for manufacturing a medicinal product for the prevention and/or treatment of neurodegenerative diseases.

In another additional aspect, the present invention relates to a method for the prevention or treatment of neurodegenerative diseases in a subject in need of treatment, comprising the administration to said subject of a pharmaceutical composition comprising a therapeutically effective amount of one or more compounds of formula (I), or a pharmaceutically acceptable salt, prodrug and/or solvate thereof. In a preferred aspect, this method for prevention or treatment acts by means of neuroprotection, particularly by means of the direct inhibition of neuronal death.

In a particular embodiment, the pharmaceutical composition used for the prevention or treatment of the mentioned diseases can be used together with other drugs, for example, drugs useful in the treatment of neurodegenerative diseases, cognitive deficits, dementias or diseases associated with aging, for the purpose of increasing the effectiveness of the pharmaceutical composition, a combination therapy therefore being generated. Said additional drugs can be part of the same pharmaceutical composition, or they can alternatively be provided as a separate pharmaceutical composition for administration at the same time (simultaneous administration) as the pharmaceutical composition used or at different times (sequential administration). By way of illustrative, non-limiting example, examples of additional drugs which can be part of the same therapy or pharmaceutical composition together with the xanthocillin analogues of formula (I) are: drugs for the treatment of Alzheimer's (tacrine, rivastigmine, memantine, donepezil, galantamine, statins . . . ), of Parkinson's (carbidopa, levodopa, bromocriptine, pramipexole, ropinirole, amantadine, rasagiline . . . ), antipsychotics such as haloperidol, antidepressants such as amitriptyline, anxiolytics such as lorazepam, anti-inflammatories such as aspirin, dietary supplements such as vitamins E, C, B, folate or *Ginkgo biloba* extract, or drugs against the other neurodegenerative diseases indicated in the patent.

In an additional aspect, the present invention relates to a compound of formula (II) as defined above, or to a pharmaceutically acceptable salt, prodrug or solvate thereof. The following are excluded from said formula:

the compound in which $R_1$-$R_4$ are OH and $R_4$ is in the meta position of the aromatic ring;

the compound in which $R_1$-$R_4$ are $OCH_3$ and the $R_4$ substituent is in the meta position of the aromatic ring; and compounds in which $R_2$ and $R_4$ are hydrogen and $R_1$ and $R_3$ are selected independently from OH and methoxy.

In a particular embodiment, if $R_2$ is hydrogen, $R_1$ is selected from methyl, ethyl and ethoxy.

In another particular embodiment, $R_1$ is selected from alkyl, OH and O-alkyl, or $R_1$ is bound to $R_2$ forming an —O-alkylene-O group.

In another particular embodiment, $R_2$, $R_3$ and $R_4$ are selected independently from hydrogen, alkyl, OH and O-alkyl, or $R_2$ is bound to $R_1$ forming an —O-alkylene-O group, and/or $R_3$ and $R_4$ are bound to one another forming an —O-alkylene-O group.

Preferably, $R_4$ is in the meta position of the aromatic ring.

Also preferably, $R_1$ is OH, O-alkyl, alkyl or forms, together with $R_2$, an —O-alkylene-O group. More preferably, $R_1$ is OH, methoxy, ethoxy, ethyl, methyl or forms, together with $R_2$, an —O-alkylene-O group.

Also preferably, $R_2$ is hydrogen, OH, alkyl or forms, together with $R_1$, an —O-alkylene-O group. More preferably, $R_2$ is hydrogen, OH, ethyl, methyl or forms, together with $R_1$, an —O-alkylene-O group.

Also preferably, $R_3$ is OH, O-alkyl, alkyl or forms, together with $R_4$, an —O-alkylene-O group. More preferably, $R_3$ is OH, methoxy, ethoxy, ethyl, methyl or forms, together with $R_4$, an —O-alkylene-O group.

Also preferably, $R_4$ is hydrogen, OH, alkyl or forms, together with $R_3$, an —O-alkylene-O group. More preferably, $R_4$ is hydrogen, OH, ethyl, methyl or forms, together with $R_3$, an —O-alkylene-O group.

In an even more preferred embodiment, the compound of formula (II) is selected from the following compounds:

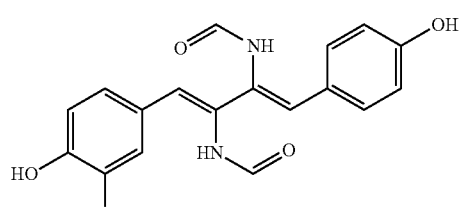

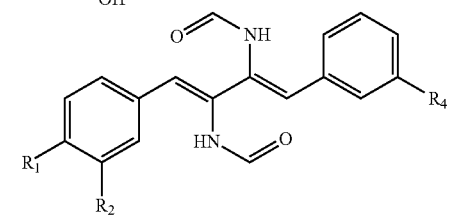

$R_1 = R_2 = R_4$ = Me, Et

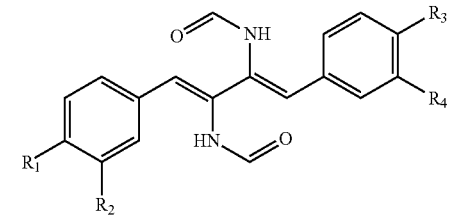

$R_1 = R_2 = R_3 = R_4$ = Me, Et

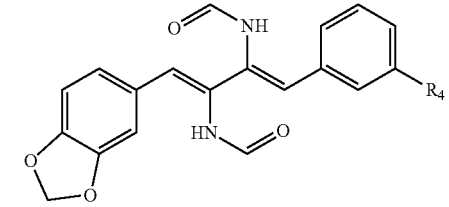

$R_4$ = OH, Me, Et

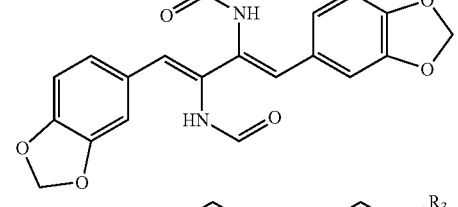

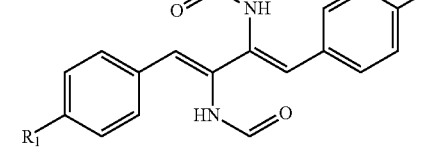

$R_1 = R_3$ = Me, Et, OEt

In an additional aspect, the present invention relates to a pharmaceutical composition comprising a compound of formula (II), or a pharmaceutically acceptable salt, prodrug or solvate thereof, and a pharmaceutically acceptable vehicle.

The term "vehicle" refers to a diluent, adjuvant or excipient with which the active ingredient is administered. Such pharmaceutical vehicles can be sterile liquids, such as water and oils, including petroleum, animal, vegetable or synthetic oils, such as oil of peanut, soybean oil, mineral oil, sesame oil and the like. Water or aqueous solutions of a saline and aqueous solutions of dextrose and glycerol, particularly for injectable solutions, are preferably used as vehicles. Suitable pharmaceutical vehicles are described in "Remington's Pharmaceutical Sciences" by E. W. Martin, 1995. Preferably, the vehicles of the invention are approved by a regulatory agency of a state or federal government or are listed in the US Pharmacopoeia or another pharmacopoeia generally recognized for use in animals, and more particularly in human beings.

Examples of pharmaceutical compositions include any solid composition (tablets, pills, capsules, granules, etc.) or liquid composition (solutions, suspensions or emulsions) for oral, topical or parenteral administration.

The administration of the compounds or compositions of the present invention can be by means of any suitable method, such as intravenous infusion, oral preparations and intravenous and intraperitoneal administration. Pharmaceutical compositions containing compounds of the invention can be administered by means of encapsulation in liposomes or nanospheres, in sustained release formulations or by means of other standard administration means.

The formulations can be prepared according to conventional methods such as methods which are described in the Spanish, European or US Pharmacopoeias, or in similar references texts, for example "Tratado de Farmacia Galénica", by C. Faulí i Trillo, 10$^{th}$ Edition, 1993, Luzán 5, S. A. de Ediciones.

The correct dosage of the compounds will vary according to the particular formulation, the method of application, the application site and the particular neurodegenerative disease being treated. Other factors such as age, body weight, sex, diet, administration time, excretion rate, combinations of drugs, reaction sensitivities and severity of the disease must also be taken into account. Administration can be carried out continuously or periodically within the maximum tolerated dose.

The compounds and compositions of this invention can be used with other drugs to provide a combination therapy. The other drugs can be part of the same composition, or they can be provided as a separate composition for administration at the same time or at a different time.

An additional aspect of the present invention is a compound of formula (II) as described above for use in medicine.

Another additional aspect of the present invention is the use of a compound of formula (II) for the preparation of a medicinal product.

In an additional aspect, the present invention relates to a method for the preparation of a compound of formula (II) starting from an extract produced by the *Penicillium chrysogenum* species. Said extract is particularly produced by a microorganism strain of the *Penicillium chrysogenum* species deposited in the CECT (Spanish Type Culture Collection) with accession number 20783.

In a particular embodiment, a sample from a marine sponge collected in the area of Cabo de Gata (Almeria), from which a strain corresponding to the *Penicillium chrysogenum* species is grown, is used as starting material for obtaining the compounds of formula (II). Said strain allows obtaining an extract from which the compounds of formula (II) are obtained by means of fractionation and purification, as described in Examples 1 and 5 of the present application.

Alternatively, the compounds of formula (II) can be obtained synthetically by means of a method comprising:
a) a condensation reaction whereby the aryl propionic acid ester of formula (III) is converted into its corresponding amide of formula (IV):

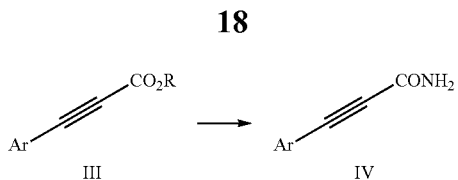

where R represents an alkyl group;

b) reacting the amide of formula (IV) with an alkyl tin hydride to produce the stannane of formula (V):

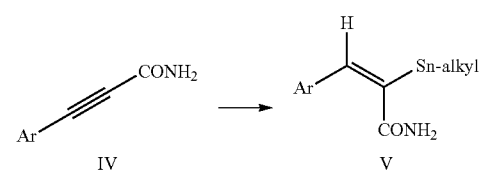

and, then subjecting the compound of formula (V) to a reaction sequence comprising:

c.1) Baumgarten oxidation reaction to provide the protected carbamate of formula (VI):

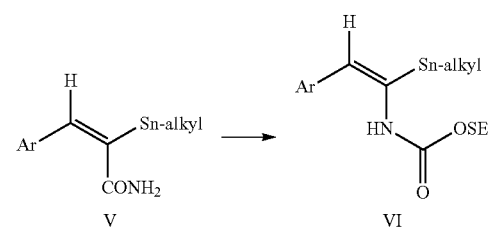

where SE means a protecting group;

d.1) subjecting the carbamate of formula (VI) to a homo-coupling reaction to give the compound of formula (VII):

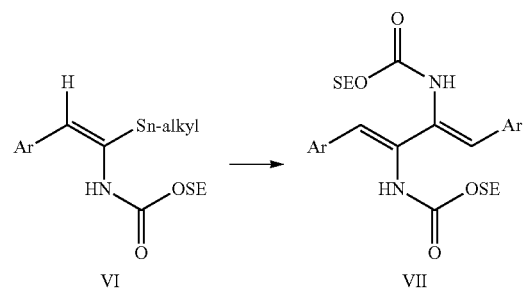

and e.1) introducing the formamido groups and deprotecting the carbamate groups to obtain the compound of formula (II) of the invention;

or subjecting the compound of formula (V) to a reaction sequence comprising:

c.2) Baumgarten oxidation reaction to provide the protected carbamate of formula (VI):

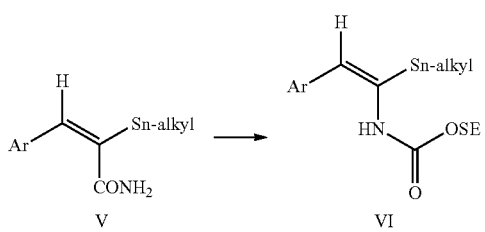

d.2) introducing the formamido groups and deprotecting the carbamate groups to obtain the compound of formula (VIII):

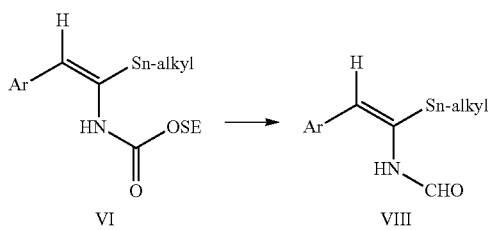

and e.2) subjecting the formamide of formula (VIII) to a homo-coupling reaction to provide the compound of formula (II) of the invention;

or subjecting the compound of formula (V) to a reaction sequence comprising:

c.3) Baumgarten oxidation reaction to provide the isocyanate of formula (IX):

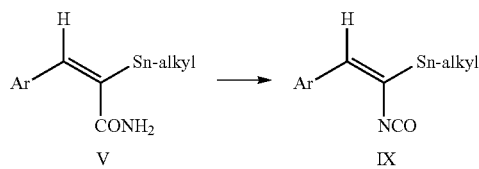

d.3) converting the isocyanate of formula (IX) into the formamide of formula (VIII):

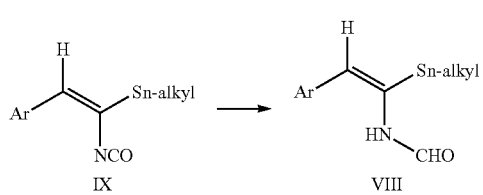

and e.3) subjecting the formamide of formula (VIII) to a homo-coupling reaction to provide the compound of formula (II) of the invention;

where the aryl group includes the $R_1$ to $R_4$ substituents depending on the compound of formula (II) that is to be obtained.

Step a) of the pathway involves converting an alkyl ester of the aryl propionic acid of formula (III) into its corresponding amide of formula (IV). In a particular embodiment, said reaction is carried out by treatment with ammonia. Preferably, the alkyl ester of the aryl propionic acid is the methyl ester of aryl propionic acid.

Step b) of the synthesis pathway involves hydrostannylation, such that the triple bond of the compound of formula (IV) is reduced, an alkyl stannane group being incorporated. In a particular embodiment, this reaction is carried out in the presence of an alkyl tin hydride and is catalyzed by a palladium compound. Preferably, the alkyl tin hydride is tributyltin hydride and the catalyst is a Pd and triphenylphosphine complex, particularly, $Pd(PPh_3)_4$.

In a particular embodiment, the Baumgarten oxidation reaction of step c.1) leading to obtaining the protected carbamate of formula (VI) is performed using an oxidant, such as $Pb(OAc)_4$, in the presence of a silanol, such as for example $TMS(CH_2)_2OH$ (2-trimethylsilanyl-ethanol). Said silanol allows incorporating silyl ether groups for the purpose of protecting the carbamate groups.

In another particular embodiment, the homo-coupling reaction of d.1) is performed using a copper catalyst, for example $CuCl_2$ and air.

Step e.1) of the synthesis pathway is carried out in two phases, a first phase in which formamido groups are incorporated by means of a formylation reaction in the presence of a strong base, and a second phase in which the protecting groups are removed from the carbamate group.

In a particular embodiment, the mentioned incorporation of the formamido groups is performed with a formic acetic anhydride after treatment with a strong base such as lithium hexamethyldisilylazanide (commonly known as LiHMDS), for example. In turn, the phase of deprotecting the carbamate groups in step e.1) can be carried out using a quaternary ammonium fluoride, specifically, tetra-n-butylammonium fluoride, either in its trihydrate form or dissolved in THF, given that it is a salt commonly used for removing silyl ether protecting groups.

The Baumgarten oxidation reaction of step c.2) corresponds to step c.1) and is therefore carried out with an oxidant in the presence of a silanol, as mentioned for the step c.1).

Step d.2) of the synthesis pathway is carried out in two phases, a first phase in which a formamido group is incorporated by means of a formylation reaction after treatment with a strong base, and a second phase in which the protecting group is removed from the carbamate group. In a particular embodiment, the mentioned incorporation of the formamido group is performed with a formic acetic anhydride after treatment with a strong base such as lithium hexamethyldisilylazanide (commonly known as LiHMDS), for example. In turn, the phase of deprotecting the carbamate group can be carried out using a quaternary ammonium fluoride, specifically, tetra-n-butylammonium fluoride, either in its trihydrate form or dissolved in THF, given that it is a salt commonly used for removing silyl ether protecting groups.

In another particular embodiment, the homo-coupling reaction of e.2) is also performed using a copper catalyst, for example $CuCl_2$ and air, as described for step d.1).

The Baumgarten oxidation reaction of step c.3) is carried out with an oxidant, as mentioned for the steps c.1) and c.2), but in the absence of the silanol given that protection of the isocyanate group is not necessary.

In turn, the reaction of d.3) for converting the carbamate of formula (VI) into the formamide of formula (IX) is performed in the presence of a reducing agent. In a particular embodiment, said reducing agent is a lithium borohydride, preferably lithium triethyl borohydride.

In another particular embodiment, the homo-coupling reaction of e.3) is also performed using a copper catalyst, for example $CuCl_2$ and air, as described for steps d.1) and e.2).

Such synthesis pathway allows obtaining the compounds in which the $R_1$ and $R_3$ and $R_2$ and $R_4$ substituents of each aromatic ring are the same. A method such as the method described in *Tetrahedron Letters*, 2005, 46, 5017-5020 can be followed to obtain compounds in which this circumstance is not present, i.e., for asymmetrical compounds.

A final aspect of the invention refers to a microorganism strain of the *Penicillium chrysogenum* species deposited in the CECT (Spanish Type Culture Collection) with accession number 20783.

Said strain was obtained from a marine sponge, as described in Example 1 herein. The strain was identified by means a PCR and sequencing technique as described in Example 4 herein, as well as by microscopic and macroscopic observation.

It is possible to obtain from said strain an extract from which the compounds used in the present invention as described above and as clearly shown in Examples 1 and 5 herein are isolated.

The following examples serve to illustrate the invention and must not be considered in a limiting sense thereof.

EXAMPLE 1

Growth of Strain 0882-08 and Obtaining Extract 08_055 C08

1.1. Isolation and Growth of the Strain

Sample M082-08 was isolated from a marine sponge collected in Cabo de Gata (Almeria) (FIG. 1). To process the sample, a piece of the sponge was extracted with the aid of sterile clamps and scissors, and several washings were performed with Artificial Seawater (ASW), the composition of which in g/L is: 0.1 KBr; 23.48 NaCl; 10.61 $MgCl_2.6H_2O$; 1.47 $KCl_2.2H_2O$; 0.66 KCl; 0.04 $SrCl_2.6H_2O$; 3.92 $Na_2SO_4$; 0.19 $NaHCO_3$; 0.03 $H_3BO_3$; sterilized in autoclave (J.P. Selecta Presoclave II 75 L) at 121° C. for 20 minutes.

Two pieces of 0.5 $cm^3$ were then extracted, depositing them in a 90 mm Petri dish containing 30 ml of PDA-marine medium, the composition of which in g/L is: 39 potato dextrose agar; 5 agar; sterilized in autoclave (J.P. Selecta Presoclave II 75 L) at 121° C. for 20 minutes.

Figure 2:
FIG. 2 is a photograph of the isolate as a pure culture of sample M082-08 inoculated in a Petri dish with PDA-marine medium; the isolate strain was called 0882-08.

The plate was incubated in a universal oven (Memmert INE700) at 28° C. for 3-5 days, periodically checking colony growth. The colony of strain 0882-08 was isolated as a pure culture with the aid of a sterile inoculation loop, inoculating it in a 90 mm Petri dish with 30 ml of PDA-marine medium, after which it is incubated in an oven at 28° C. (FIG. 2).

Once the pure culture was obtained, it was grown in agar slant tubes with Power (PW) medium, the composition of which in g/L is: 15 sucrose; 2.5 bacteriological peptone; 2.5 lactose; 0.5 corn mash solids; 2 NaCl; 1 $NaNO_3$; 26.1 KCl; 0.25 $K_2HPO_4$; 0.25 $MgSO_4.7H_2O$; 0.03 $KH_2PO_4$; 0.005 $FeSO_4.7H_2O$; 0.0015 $FeCl_3.6H_2O$; 0.0005 $CuSO_4.5H_2O$; 20 agar; pH 5.5; sterilized in autoclave (J.P. Selecta Presoclave II 75 L) at 121° C. for 20 minutes.

After 7 days and having found that the culture had grown and sporulated, a suspension of spores was prepared using the following method: 10-15 glass beads 5 mm in diameter and 5 ml of sterile 40% (w/v) glycerol are added to each tube. The culture is shaken until achieving a homogenous suspension and thereby generating the cryovials which are conserved at −80° C. in an ultra-low temperature freezer (Thermo Scientific 905-86 C ULT Freezer).

1.2. Obtaining the Extract

The culture for obtaining the natural extract was prepared by inoculating a 13 ml polypropylene tube with 3 ml of agar slant with solid YES medium, the composition of which in g/L was: 150 sucrose; 20 yeast extract; 0.5 $MgSO_4.7H_2O$; 10 agar; with 0.05 ml of the suspension of spores conserved at −80° C. The tube was incubated in an oven at 28° C. for 14 days. After that time, 3 mL of ethyl acetate were added to the culture, after which it was vigorously shaken with a vortex for several seconds. It was then introduced in an ultrasonic bath for 15 minutes, after which 1 g of anhydrous sodium sulfate was added, and it was shaken again for several seconds in a vortex. It was centrifuged at 3000×g for 10 minutes, after which the supernatant was collected. An additional 3 mL of ethyl acetate were added to the pellet resulting from centrifugation, and another extraction cycle was performed (without adding sodium sulfate), at the end of which cycle the supernatant bound to the previous extract. It was evaporated to dryness in a rotavapor or under nitrogen stream, yielding between 1 to 10 mg of dry crude extract. It was evaporated to dryness in a rotavapor and speed-vac.

EXAMPLE 2

Evaluation of the Neuroprotective and Antioxidant Capacity of Extract 08_055 C08

2.1. Evaluation of the Neuroprotective Capacity

The crude extract obtained was resuspended in 800 μL of DMSO to test it on the model of oxidative stress-induced cell death. This assay is performed on SK-N-MC human neuroblastoma culture cells from the American Type Culture Collection (ATCC, Cod. HTB-10™), following strict sterility standards and handling them in class II biological safety cabinets which follow European standard EN 12469. The cells were maintained in MEM medium (Minimum Essential Medium Eagle) supplemented with 1 mM sodium pyruvate, 2 mM L-glutamine, 0.1 mM non-essential amino acids, 0.05 mg/ml gentamicin and 10% fetal bovine serum. The inhibition in these cells caused by the extract with respect to cell death caused by treatment with xanthine/xanthine oxidase (XXO) which generates oxidative damage (production of free radicals such as hydrogen peroxide, superoxide anion, hydroxyl radical), which triggers cell death, was analyzed. These cells, not exceeding 15 passages, were seeded on 96-well plates treated for adherent cells with a cell density of $5 \times 10^4$ cells/well. After 24 hours of cell incubation at 37° C. and 5% $CO_2$, the cell treatments for the control conditions (culture medium); XXO (xanthine 10 μM/xanthine oxidase 60 mU/mL, which causes the death of 50% of the cells); XXO plus the extract at a final dilution of 1/100, 1/400, 1/1,000, 1/4,000 and 1/10,000, were performed. After 22 hours of incubation, WST-1 reagent (Roche) was added following the manufacturer's specifications. The WST-1 test is based on the measurement of metabolic activity such that the metabolically active (live) cells reduce the tetrazolium salt of WST-1 to formazan by means of the succinate-tetrazolium reductase system of the mitochondrial respiratory chain. The formazan produced is colorimetrically detected.

Figure 3:
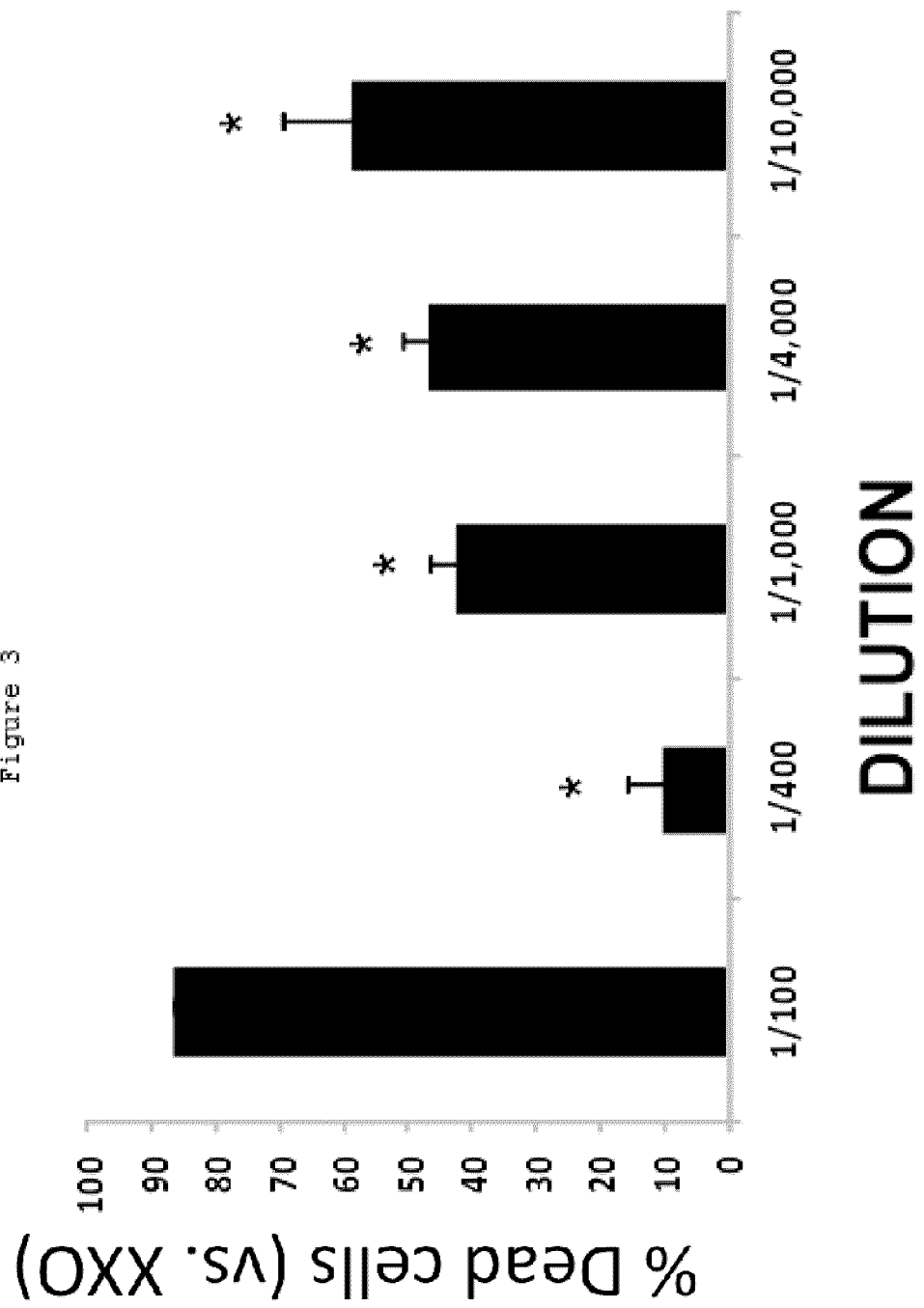
FIG. 3 is a bar graph showing the protection of different dilutions of extract 08_055 C08 against cell death caused by 10 μM xanthine/60 mU xanthine oxidase/mL (XXO). The figure shows the percentage of cell death (the cell death caused by XXO being 100%) of the cultures treated with 1/100, 1/400, 1/1,000, 1/4,000 and 1/10,000 dilutions of the extract in the presence of XXO, representing the means±SD of one experiment in triplicate. * Significant difference with respect to treatment with XXO according to the Student's t test (p<0.05).

The obtained results are shown in FIG. 3 as the percentage of cell death for each dilution relating to death caused by XXO. Protection at the dilutions of 1/400, 1/1,000, 1/4,000 and 1/10,000 was observed, maximum protection being 90% at 1/400, so extract 08_055 C08 shows a protective effect against human neuronal cell death caused by oxidative stress.

2.2. Evaluation of Antioxidant Capacity

Based on the preceding results, the inventors decided to evaluate in vitro antioxidant capacity of the extract, for which the TEAC assay (absorbance capacity by electron transfer) was used. This method is based on the formation of the ferryl-myoglobin radical produced by reacting metmyoglobin with hydrogen peroxide, followed by the oxidation of the ABTS [2,2'-azino-bis(3-ethylbenzthiazoline-6-sulfonic acid] reagent by ferryl-myoglobin, which produces the radical cation ABTS*+, which can be colorimetrically determined. In this assay, the compounds with antioxidant capacity suppress the production of the radical in a concentration-dependent manner. A standard curve with increasing concentrations of trolox (6-hydroxy-2,5,7,8-tetramethylchroman-2-carboxylic acid, hydrosoluble vitamin E analogue) is used to quantify antioxidant capacity, such that the results are indicated as a measurement of trolox equivalents (TE). The assay on extract 08_055 C08 at a dilution of 1/1,000 yielded 101±18 µM TE, which indicates that this extract shows in vitro antioxidant capacity.

EXAMPLE 3

Evaluation of the Biosafety of Extract 08_055 C08

3.1. Evaluation of Safety in Human Cell Lines

Based on the preceding results, the inventors decided to additionally evaluate the safety of this extract in two human cell lines: human neuronal cell lines (SK-N-MC, Cod. ATCC HTB-10™) and human hepatic cell lines (HepG2, Cod. ATCC HB8065™), by means of measuring cell viability with extract 08_055 C08 at the maximum dilution (1/100), for which purpose the measurement of the metabolic activity by means of the WST-1 test (Roche) is used. Viability of 126±7% is obtained with respect to the control in SK-N-MC cells and viability of 101±7% is obtained in HepG2, so extract 08_055 C08 does not show in vitro toxicity.

3.2. Evaluation of Safety in Zebrafish Embryos

Based on the preceding results, the inventors decided to evaluate the biosafety in zebrafish embryos following the specifications defined in the Draft Guideline of May 30, 2006 (1st Version) called "OECD guideline for the testing of chemicals draft proposal for a new guideline: Fish Embryo Toxicity (FET) Test". This test is an alternative method with respect to the acute toxicity test with young and adult fish (OECD Test Guideline 203). Three zebrafish embryos, in 10 replicates (n=30 per condition), were individually exposed in a 96-well microtiter plate at three concentrations of the substance to be evaluated (1/100, 1/200, 1/400). The test began immediately after fertilization and continued for 48 hours without replacing treatment. The lethal effects, described by four endpoints, were determined by comparison with the controls to identify the LC50, NOEC and LOEC values, which parameters are defined next. LC50: Concentration of the test sample causing mortality of 50% of the animals. NOEC: Highest concentration not causing mortality. LOEC: Lowest concentration causing 100% mortality. The test methodology was based on using a series of concentrations of the compound to be evaluated as well as a suitable control. The following toxicological parameters were determined in this study. Lethal parameters: i) determination of the number of coagulated eggs; ii) tail detachment; iii) heart rate (presence or absence); iv) somite formation (somites are longitudinal series of the mesoderm which become the axial skeleton, dermis and dorsal muscles and the body wall and limbs by delamination, fusion and migration). Furthermore, the following sub-lethal parameters were also studied: i) spontaneous movements; ii) pigmentation; iii) edema formation; iv) clot formation. Finally, the following teratogenic parameters were studied: i) malformations in organs and structures; ii) scoliosis; iii) rickets, iv) general developmental delay. The obtained results are shown in FIG. 4, showing the toxicity parameters in a zebrafish embryo in an assay based on the FET at 48 hours post-treatment (hpt) of extract 08_055 C08. It is observed that at the doses used and at end time (48 hours post-treatment), no toxicological phenomenon was determined in the zebrafish embryos, so said extract showed extraordinary safety in the evaluated models.

EXAMPLE 4

Identification and Scaling-Up of Strain 0882-08

4.1. Identification of the Strain

The strain was identified by means of PCR amplifying 560 bp of the 28S gene. The PCR mixture contains the following components: PCR buffer, 1.5 mM $MgCl_2$, mixture of 0.2 mM dNTPs, 0.4 µM oligonucleotides (NL1: 5'-gca tat caa taa gcg gag gaa aag-3' (SEQ ID No:1) and NL4: 5'-ggt ccg tgt ttc aag acg g-3' (SEQ ID No:2)), PFU DNA polymerase (Bioneer) 1 U, genomic DNA was isolated from the strain with the Wizard SV Genomic DNA Purification System kit (Promega) at a final dilution of 1:50.

The PCR program consisted of: denaturation in 1 cycle at 96° C. for 5 minutes; amplification in 30 cycles with three temperature ramps: 94° C. for 30 seconds, 60° C. for 40 seconds and 72° C. for 1 minute; elongation in 1 cycle at 72° C. for 10 minutes.

The obtained 28S gene fragment (FIG. 5, SEQ ID No:3) was sequenced and showed similarity with the *Penicillium* genus by comparison with the Basic Local Alignment Search Tool (BLAST) database of the National Center for Biotechnology Information (NCBI, USA), which coincided with its microscopic and macroscopic characteristics. Based on this result, a first approximation of this strain to the *Penicillium* genus was performed. Therefore, according to the method described by Samson and Frisvad (2004) [Frisvad & Samson, Stud. Mycol. 2004; 49: 1-173], the strain was inoculated in the following culture media and incubated for 7 days at different temperatures:

Czapek Yeast Extract Agar (CYA). Incubated at 5° C., 26° C. and 37° C.

Malt Extract Agar (MEA). Incubated at 26° C.

Yeast Extract Sucrose Agar (YES). Incubated at 26° C.

Creatine Sucrose Agar (CREA). Incubated at 26° C.

25% Glycerol Nitrate Agar (G25N). Incubated at 26° C.

The characteristics used in the classification were: microscopic observation, data on growth, colony morphology and formation of the teleomorph state, where appropriate. The microscopic observation results showed fruiting bodies (paintbrushes) characteristic of the *Penicillium* genus. Conidiophores with three branch points (terverticillate) characteristic of the *Penicillium* subgenus. Smooth-walled stipe. Ampulliform phialides. Smooth, spherical to ellipsoidal conidia.

The characteristics studied in the macroscopic observation were: size, texture and color of the colonies, production of exudate and diffusible pigment and observation of the back. The results are the following:

Growth in CYA at 26° C.: colonies 35 mm in diameter. Velvety to floccose, fasciculate texture. White mycelium. Grayish green conidia. Does not produce exudate. Produces yellow diffusible pigment to the medium. Yellow back.

Growth in CYA at 5° C. and 37° C.: colonies 10 mm in diameter. Velvety texture. White conidia. Does not produce exudate or diffusible pigment into the medium. Cream back.

Growth in MEA and G25N at 26° C.: colonies 33 mm and 27 mm in diameter, respectively. Floccose texture. Grayish green conidia. Does not produce exudate or diffusible pigment into the medium. Cream back.

Growth in YES at 26° C.: colonies of 40 mm in diameter. Velvety to floccose texture. White mycelium. Grayish green conidia. Does not produce exudate or diffusible pigment into the medium. Cream back with grayish center.

Growth in CREA at 26° C.: little growth, colonies 9 mm in diameter. Production of acid.

Identification was made at the molecular level by the following molecular methods:
  a) Amplification and sequencing of rDNA intergenic spacer (ITS1 and ITS2), including the 5.8S rDNA gene.
  b) Amplification and subsequent partial sequencing of the β-tubulin gene (with readings in two directions), with Bt2a and Bt2b primers (Glas & Donaldson, Appl Environ Microb 1995; 61:1323-30).

The PCR products had 495 and 477 base pairs, respectively. As a result of the comparison thereof with the sequences in the databases, a 100% similarity was obtained for the ITS-5.8S rDNA area, and 99% similarity was obtained for the β-tubulin gene with the *Penicillium chrysogenum* species, strain CBS 306.48.

It is therefore concluded that the strain belongs to the *Penicillium chrysogenum* species.

4.2. Scaling-Up the Culture

The cultures for obtaining the natural extract were prepared for scaled-up culture growth by inoculating 25 Petri dishes of 14 cm diameter containing 80 mL of YES medium, with 1.2 ml of a suspension of spores each. The medium composition is (g/L): 150 sucrose; 20 yeast extract; 0.5 $MgSO_4 \cdot 7H_2O$; 10 agar; and incubating said plates at 28° C. for 14 days.

The extraction of the culture was performed by grinding with the aid of a blender such that it was completely homogenous, then 2300 mL of ethyl acetate were added and it was maintained under stirring for 6 hours with the aid of a rod stirrer. After this time, the supernatant was collected and filtered through a paper funnel. The extraction was repeated adding 1900 mL of ethyl acetate and was maintained under stirring for another 4 hours. The supernatant was collected and pooled with the previous supernatant. It was all evaporated to dryness by means of a rotavapor, yielding 3.3 g of the dry crude extract.

EXAMPLE 5

Fractionation, Bio-Guided Purification, and Resolution of the Structure of the Active Compound Present in Extract 08_055 C08 of the Culture of Strain 0882-08

5.1. Fractionation and Purification

Extract 08_055 C08 was analyzed by analytical HPLC (Agilent 1100-DAD, Zorbax RX-C8 5 μm 4.6×250 mm Column) with 5-100% acetonitrile/water for 40 minutes and it was observed that the extract contained metabolites in all the ranges of polarity, as a result was performed a generic low-pressure fractionation by broad range adsorption/resorption fractionation by broad range adsorption/resorption resin (SP207ss) in a Combiflash® automated chromatograph. To that end, 1.2 g of the extract were dissolved in 2 mL of 50/50 ethyl acetate/methanol and then 5 grams of water drained sp207ss resin were added, evaporating all the solvent to dryness, thereby obtaining the head space of the chromatography column. Therefore, all the crude product was fractionated in a Combiflash automated chromatograph by means of 70 mL (100 mm×35 mm) SP207ss resin column in a 10-100% parabolic gradient of acetone in water for 25 minutes with additional 100% acetone washing lasting 35 minutes.

Seventeen fractions were obtained to which 1.4 mL of DMSO were added per fraction and the chromatography solvents were evaporated by means of a Genevac centrifugal evaporator for 7 hours, yielding the fractions in 100% DMSO at 715×WBE (whole broth equivalent or equivalent concentration during fermentation).

The fractions were analyzed with respect to xanthine/xanthine oxidase-induced death (with the same method used for the screening analysis described in Example 2), obtaining protection in several of the analyzed fractions, so the purification was focused on the area of greater activity at high dilutions.

To that end, fractionation of the positive fractions was scaled-up, by means of preparative HPLC, with a gradient of 2 to 20% acetonitrile/water with a Zorbax SB-C8 7 μm 21.2×250 mm column with a flow rate of 20 mL/min and detection at 210 and 280 nm. The preparative HPLC fractions were tested to locate which chromatography peak or peaks showed protective activity against death.

Figure 6:
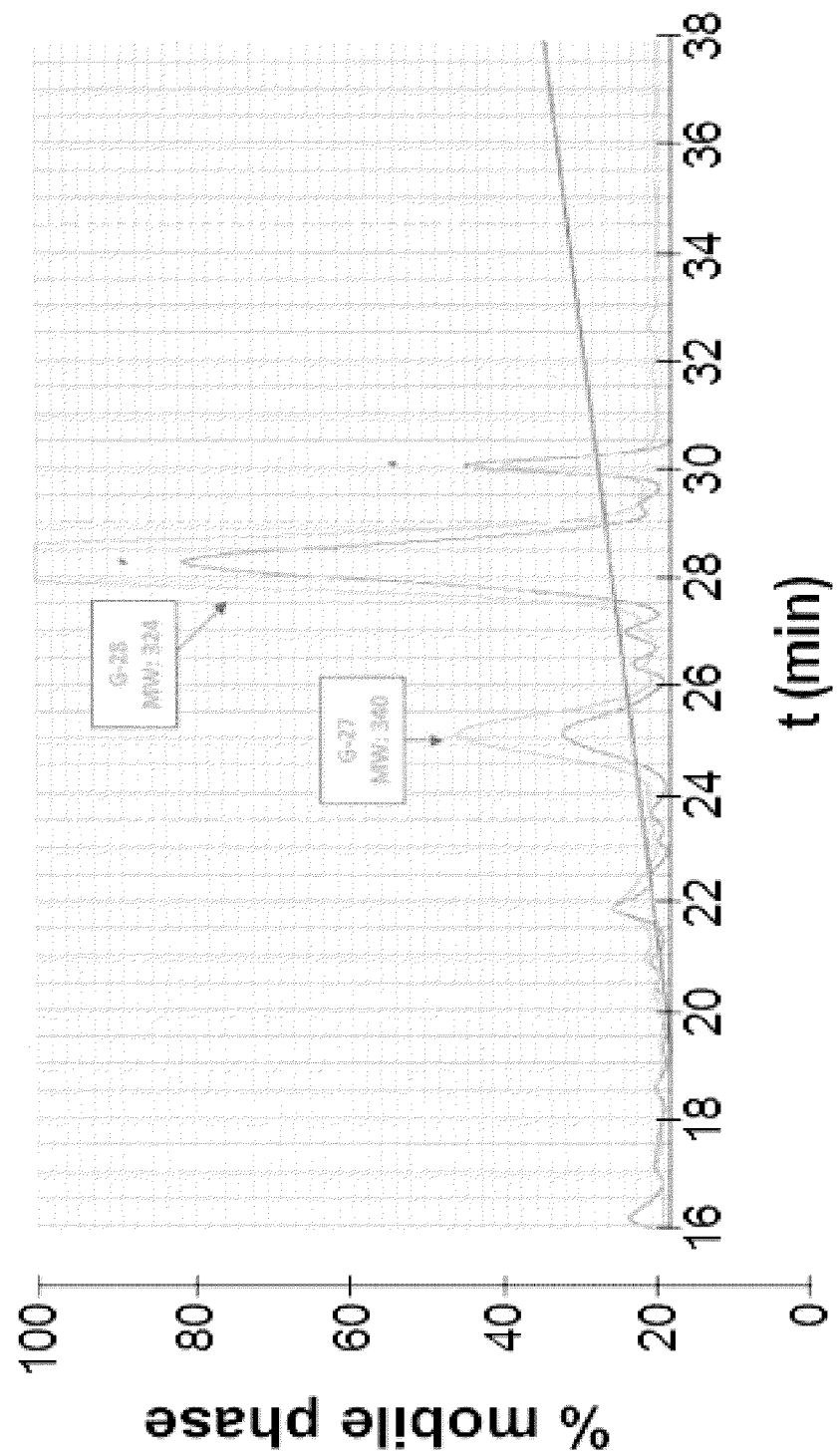
FIG. 6 is the chromatogram of the low-resolution HPLC/MS analysis of the compounds with molecular weights of 340 m/z (corresponding to peak G27) and 324 m/z (peak G28) obtained from fractioning extract 08_055 C08.

Two majority compounds (FIG. 6) were obtained in fractions G27 and G28, the low resolution HPLC/MS analysis of which showed that they had molecular weights of 340 and 324 m/z, respectively. During re-purification, a third peak appeared for which the low resolution HPLC/MS analysis indicated a molecular weight of 324 m/z, and it was confirmed by analytical HPLC and NMR/MS to be a conformer present in equilibrium with the original G28.

5.2. Resolution of the Structure

To carry out structural elucidation of the two purified bioactive compounds G27 (340 m/z) and G28 (324 m/z), a combination of spectroscopic techniques was used, including high resolution ESI-TOF mass spectrometry and both one- and two-dimensional nuclear magnetic resonance (NMR) spectrometry, supported with searches in databases using the molecular formula and/or structural characteristics that can be deduced from the NMR spectra of the compound. The latest edition of the Chapman & Hall Dictionary of Natural Products (Chapman & Hall, 2011) was used to do this.

5.2.1. Elucidation of the Structure of G28 (NPS0156)

Figure 7:
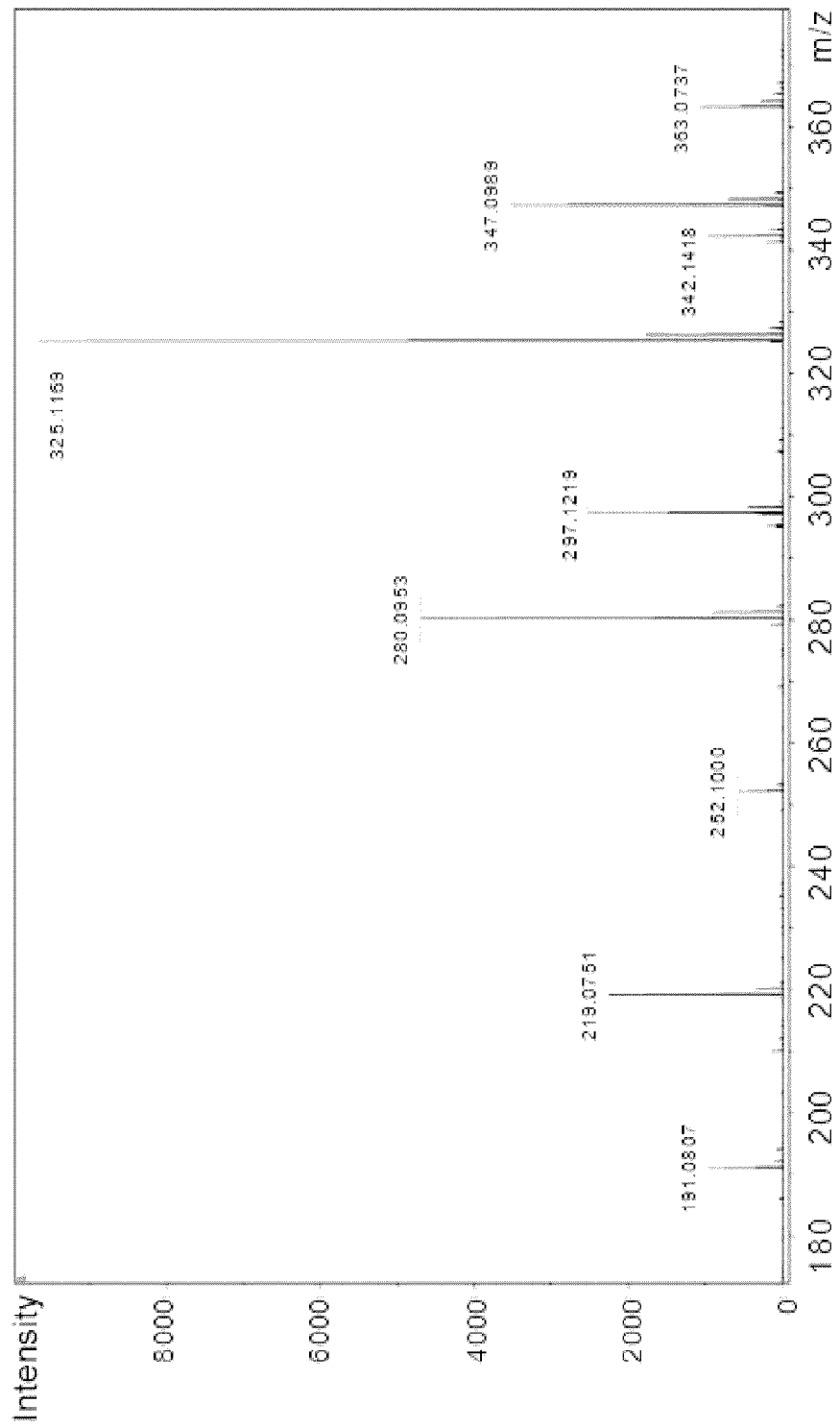
FIG. 7 is the mass spectrum (ESI-TOF) of peak G28 corresponding to compound NPS0156.

For elucidation of the structure of compound G28, high-resolution ESI-TOF analysis was performed, which indicated the presence of a pseudomolecular ion at an m/z ratio of 325.1169, consistent with a molecular formula of $C_{18}H_{16}N_2O_4$ (calculated for [M+H]+ 325.1183, Δ=-4.3 ppm). The presence of the corresponding ammonium adduct (m/z 342.1418), sodium adduct (m/z 347.0989) and potassium adduct (m/z 363.0737) in the mass spectrum (FIG. 7) confirmed the molecular formula proposed for the compound.

A search for said molecular formula in the Chapman & Hall Dictionary of Natural Products disclosed the presence of two molecules with these characteristics, N-Nitrosoxylopine, isolated from the plant *Duguetia furfuracea*, and (1Z,3Z)-1,4-Di(4-hydroxyphenyl)-2,3-diformamido-1,3-butadiene, molecule previously obtained from *Penicillium notatum* fungus culture broths. After a solubility test in different solvents, it was decided that DMSO-d6 was the most suitable for recording NMR spectra.

Figure 8:
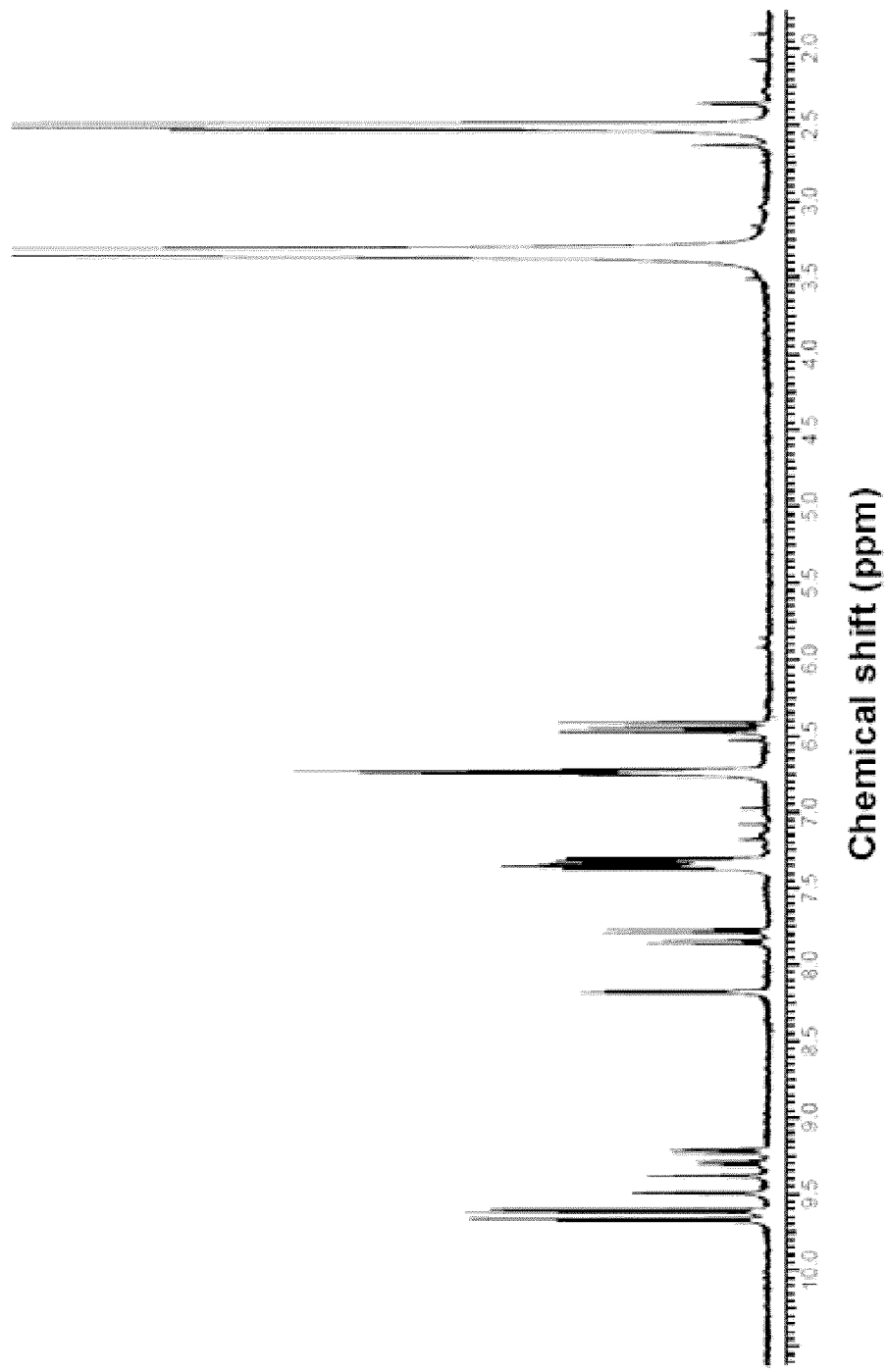
FIG. 8 is the $^1H$ NMR spectrum of peak G28 corresponding to compound NPS0156.
Figure 9:
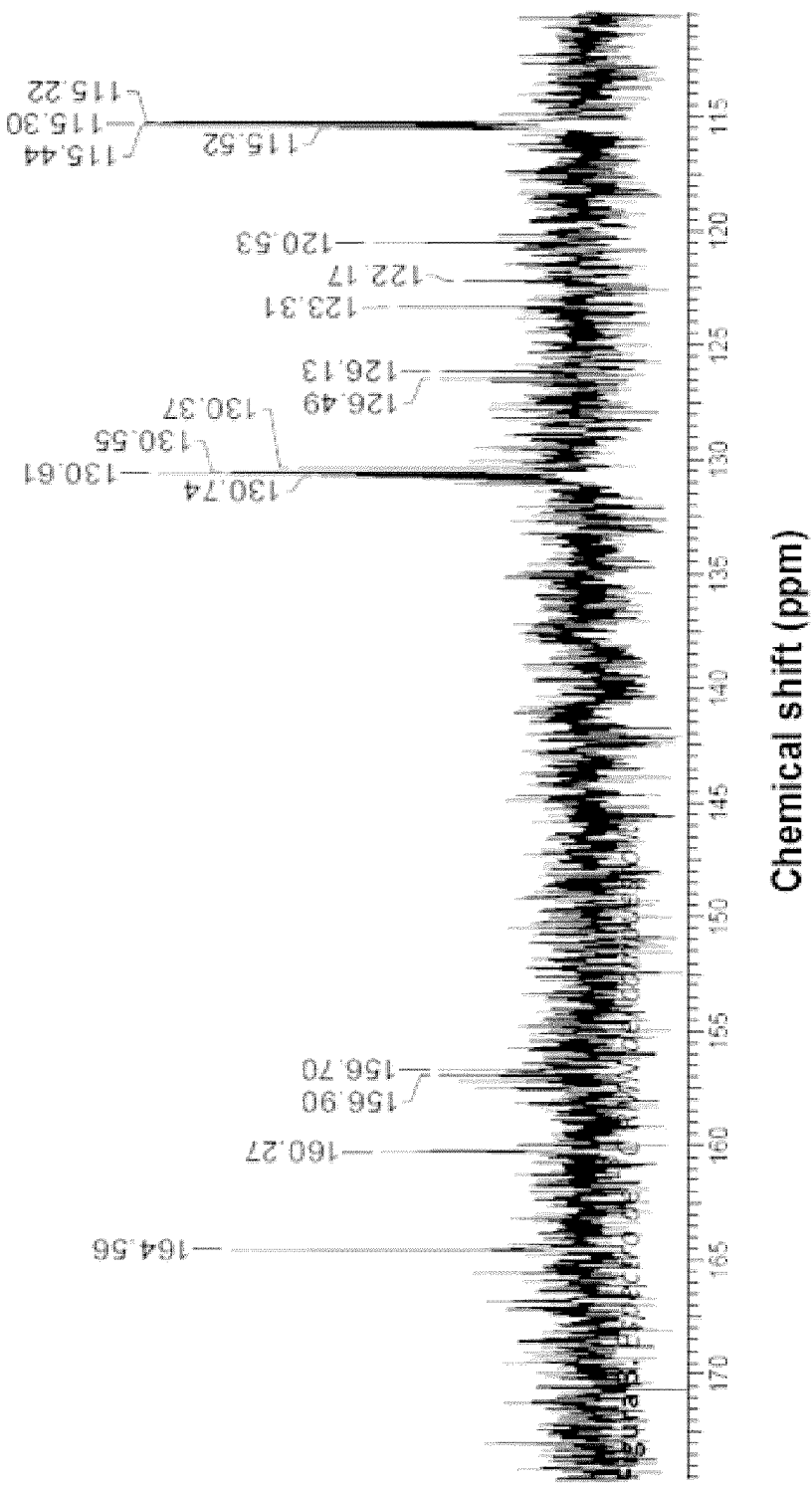
FIG. 9 is the $^{13}C$ NMR spectrum of peak G28 corresponding to compound NPS0156.

The $^1$H NMR spectrum (FIG. 8) turned out to be fairly complex, with a number of signals that indicated the presence of at least 32 protons in the molecule, which led the inventors to think that the molecule presented some type of conformational equilibrium, which was already detected during the purification process, which led to signal splitting. Besides the residual signals of the deuterated solvent, the spectrum additionally contained signals due solely to the presence of aromatic protons and/or of a double bond and of protons bound to heteroatoms, which allowed rejecting all those molecules that contain aliphatic protons such as N-Nitrosoxylopine. The other candidate found in the molecular formula search, (1Z,3Z)-1,4-Di(4-hydroxyphenyl)-2,3-diformamido-1,3-butadiene, would show structural characteristics that could be consistent with the observed spectrum and would furthermore include within its structure two formamide groups, the conformational equilibrium of which could be detected by means of NMR, leading to signal splitting. There were three possible conformations for the two amide groups: cis-cis, trans-trans and cis-trans, with two equivalent possibilities for the last conformation due to the symmetry of the molecule. Said symmetry determines that the number of different signals in the proton that would be observed for the possible conformations was 32, coinciding with the number of signals observed in the spectrum. To confirm the identity of compound G28, a $^{13}$C NMR spectrum was carried out (FIG. 9); all the described signals of the $^1$H and $^{13}$C NMR spectra are detailed in FIG. 10. Said spectrum showed a number of signals consistent with the existence of conformers in the molecule and with chemical shifts coinciding with the shifts described in the literature for (1Z,3Z)-1,4-Di(4-hydroxyphenyl)-2,3-diformamido-1,3-butadiene (Zuck et al., J. Nat. Prod. 2011; 74: 1653-7). Likewise, the number of signals and chemical shifts observed in the $^1$H NMR spectrum are also consistent with those described for this molecule. It is therefore concluded that compound G28 obtained in the bioassay-guided chromatography of extract 08_055 C08 has the structure of (1Z,3Z)-1,4-Di(4-hydroxyphenyl)-2,3-diformamido-1,3-butadiene.

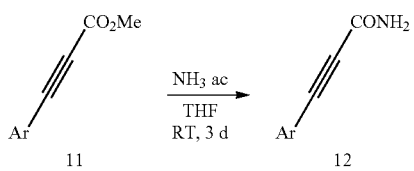

5.2.2. Elucidation of the Structure of G27 (NPS0155)

Figure 11:
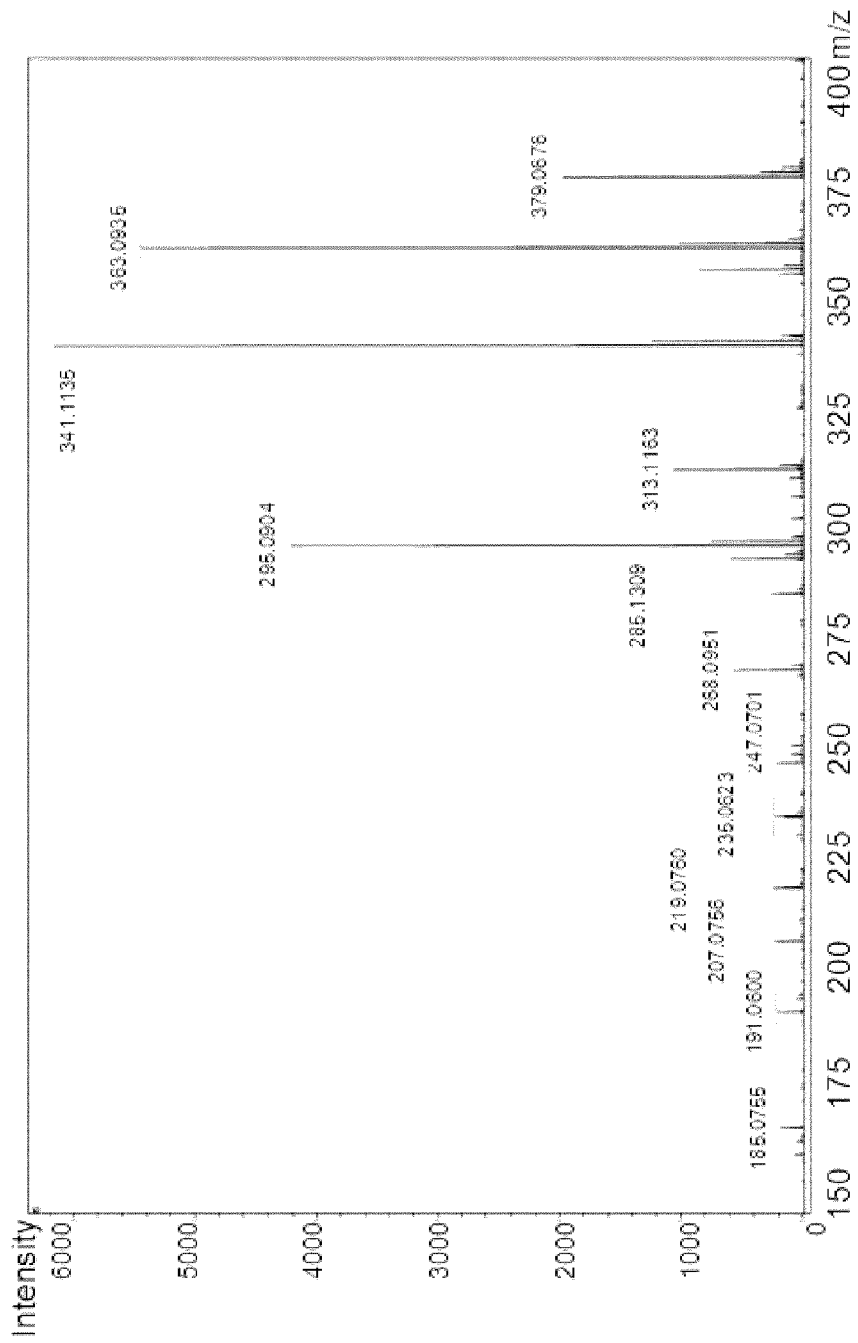
FIG. 11 is the mass spectrum (ESI-TOF) of peak G27 corresponding to compound NPS0155.
Figure 12:
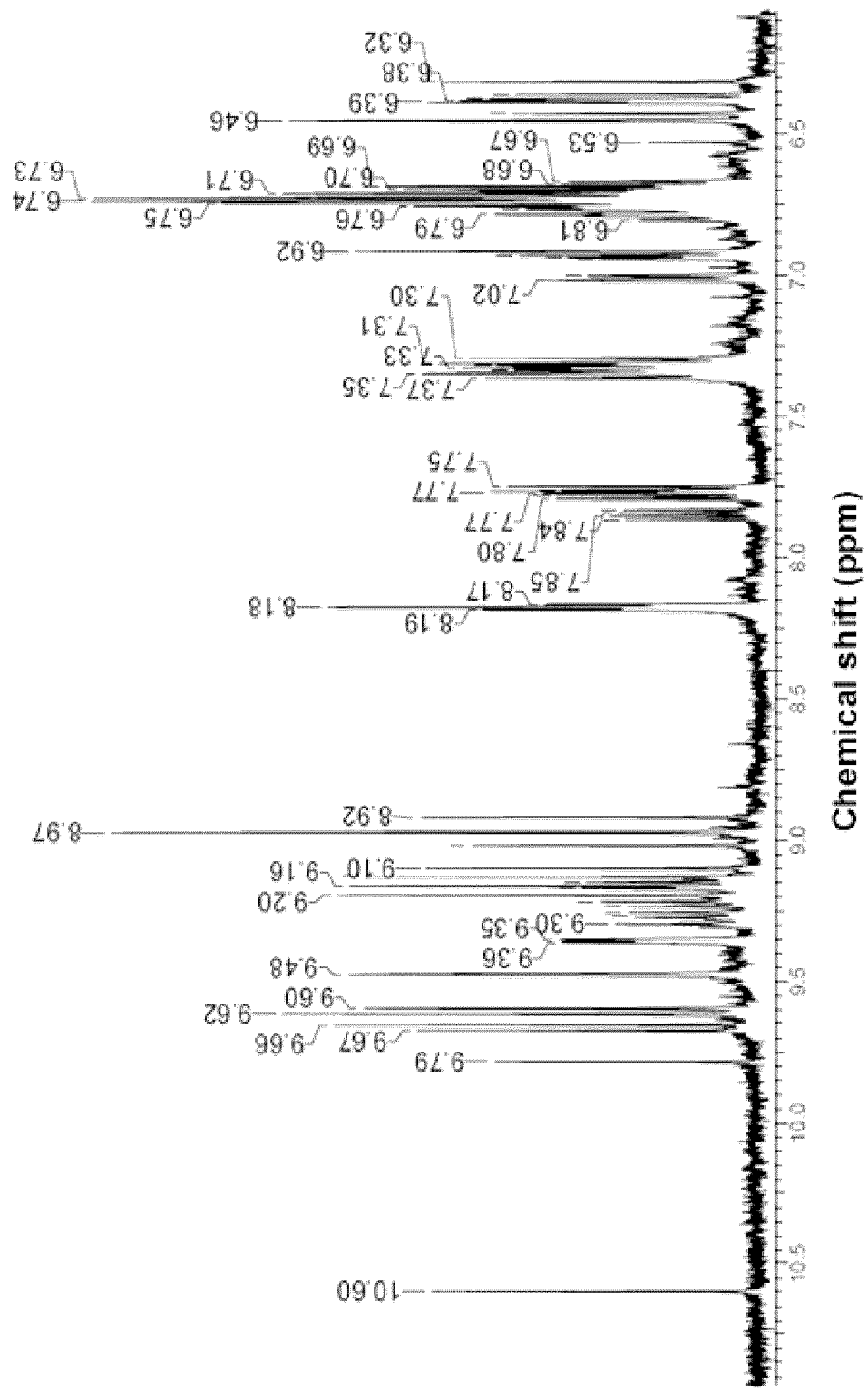
FIG. 12 is the $^1H$ NMR spectrum of peak G27 corresponding to compound NPS0155.
Figure 13:
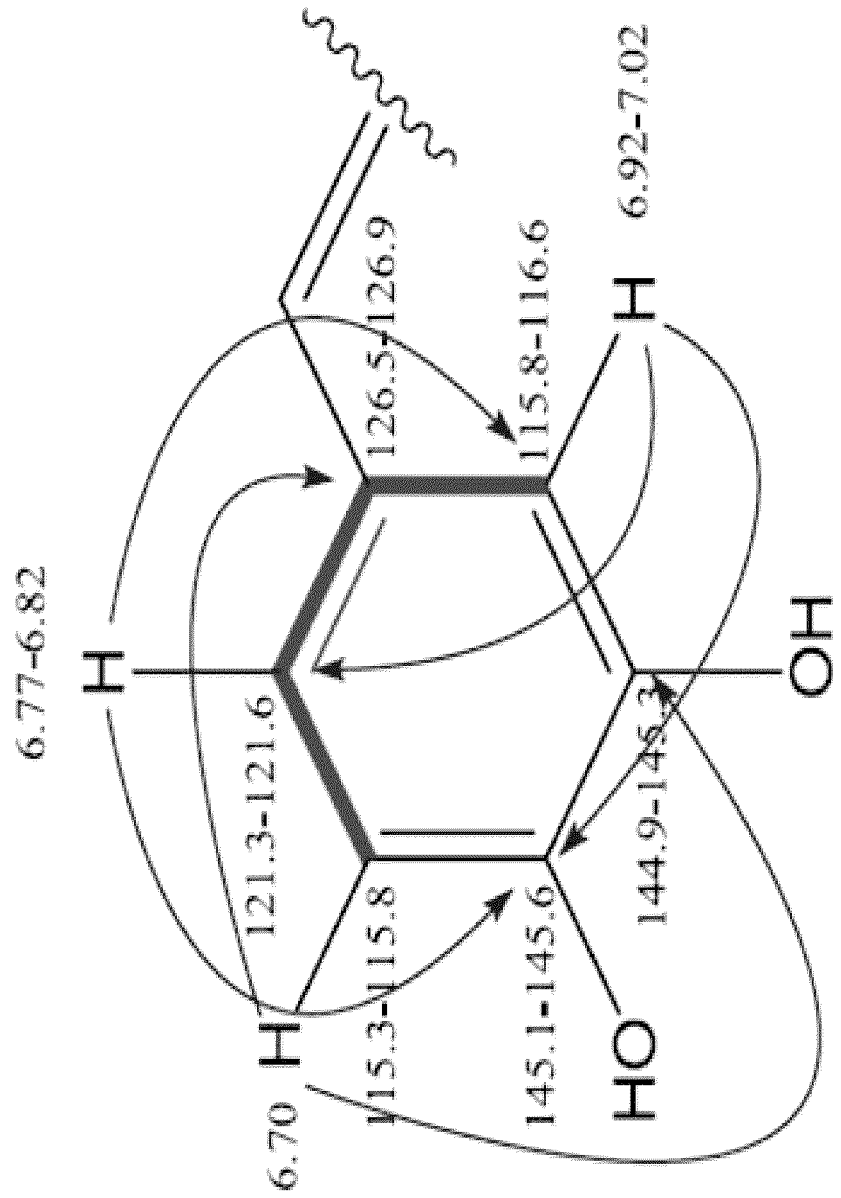
FIG. 13 is a diagram showing the correlations observed in the COSY (red) and HMBC (blue) spectra for the aromatic protons of the 3,4-dihydroxyphenyl substituent.

Compound G27 has molecular formula $C_{18}H_{16}N_2O_5$ as deduced from its mass spectrum analysis (ESI-TOF) (m/z 341.1116, calculated for [M+H]+ 341.1132, Δ=−4.6 ppm). As in the case of compound G28, the presence of ammonium adduct (m/z 358.1365), sodium adduct (m/z 363.0935) and potassium adduct (m/z 379.0676) in the mass spectrum (FIG. 11) corroborate the proposed molecular formula. The molecule therefore seems to have the same chemical nature as compound G28, including an additional oxygen atom in its structure. The search for its molecular formula in the Dictionary of Natural Products identified in this case three possible molecules, cephalinone B, acetylnybomycine and picrasidine E, none of which is related to said compound. It surprisingly seemed that compound G27 was a new natural product. Just like for compound G28, DMSO-d6 was shown to be the most suitable solvent for carrying out the NMR experiments. The $^1$H NMR proton spectrum (FIG. 12) showed greater complexity than it did for compound G28, with the existence of a number of signals in the aromatic proton and/or double bond areas and in the area of protons bound to heteroatom. The presence of an additional oxygen in the structure would disrupt the symmetry of this compound and the number of observable signals in the spectrum would considerably increase, taking into account the existence of four amide conformers (cis-cis, trans-trans, cis-trans and trans-cis) now, each of which would give rise to different signals. Therefore 64 different signals (16H×4 conformations) in the proton spectrum of the molecule would be expected. A detailed analysis of the $^1$H NMR spectrum showed the presence of 12 phenolic proton signals (δH 9.67, 9.66, 9.62, 9.60, 9.20, 9.16, 9.13, 9.10, 9.02, 8.97 (×2) and 8.92), therefore confirming the presence of an additional phenolic hydroxyl with respect to compound G28. The region of the spectrum corresponding to aromatic protons was analyzed to localize said phenolic group. The presence of doublets at 7.02 (J=2.0 Hz), 7.00 (J=2.0 Hz), 6.94 (J=2.0 Hz) and 6.92 (J=2.0 Hz), which correlated in the $^1$H-$^1$H COSY spectrum with a group of signals between 6.77 and 6.82 ppm and in HMBC with carbons at 121.3-121.6 ppm and at 145.1-145.6 ppm, is observed in said region. The group of signals at 6.77-6.82 ppm in proton correlated in turn with a multiplet centered at 6.70 ppm in the COSY spectrum and with carbon signals at 115.8-116.6 and 145.1-145.6 in the HMBC spectrum. Finally, the multiplet centered at 6.70 ppm correlated in HMBC with carbons at 126.5-126.9 ppm and at 144.9-145.3 ppm. All this data is consistent with the replacement of one of the 4-hydroxyphenyl groups present in the structure of compound G28 with 3-4-dihydroxyphenyl in compound G27 (FIG. 13). Besides the already mentioned signals, are observed in the proton spectrum other signals corresponding to the protons of amide NH groups at δH 9.48 (s, ×2), 9.36 (s), 9.35 (s), 9.30 (d), 9.26 (d), 9.22 (d) and 9.17 (d) ppm, four of which are singlets corresponding to the cis amide conformations and the other four are doublets, corresponding to the trans conformations. The signals of the protons of the two formamide groups are likewise observed at 8.19 (s), 8.18 (s×2), and 8.17 (s) (cis), and a 7.86 (d), 7.84 (d), 7.79 (d) and 7.77 (d) (trans). The signals observed in the spectrum are completed with those corresponding to the protons of the 4-hydroxybenzyl substituent (7.30-7.38 and 6.72-6.77 ppm) and those of eight singlets corresponding to the H1 and H4 protons of the butadiene present in the molecule (δH 6.46 (×2), 6.43, 6.39, 6.39, 6.38, 6.36, 6.32). All the remaining signals of the $^{13}$C NMR spectrum (FIG. 14) not described above and the correlations observed in the two-dimensional COSY, HSQC and HMBC spectra corroborate the proposed structure. Compound G27, obtained in the bioassay-guided chromatography of extract 08_055 C08, therefore has the structure of (1Z,3Z)-1-(3,4-dihydroxyphenyl)-4-(4-hydroxyphenyl)-2,3-diformamido-1,3-butadiene. The search in the literature for the structure further confirmed that it is a new natural product.

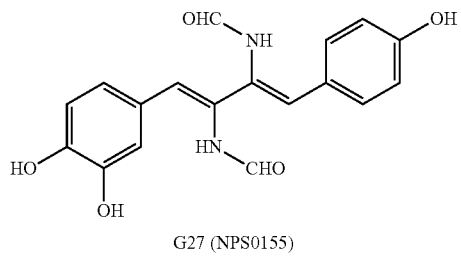 [SMILES: O=CNC(=C\c1ccc(O)cc1)/C(=C/c1ccc(O)c(O)c1)NC=O]

G27 (NPS0155)

EXAMPLE 6

Protective Effect of Peaks G27 (or Compound NPS0155) and G28 (NPS0156) on Oxidative Stress-Induced Neuronal Death Based on the preceding results, the researchers decided to analyze the neuroprotective effect of compounds NPS0155 and NPS0156. The assays were performed on SK-N-MC human neuroblastoma culture cells, maintained as detailed in Example 2.

The inhibition of cell death by both compounds caused by treatment with xanthine/xanthine oxidase, which causes oxidative damage (generating free radicals such as hydrogen peroxide, superoxide anion, hydroxyl radical) which trigger cell death, was analyzed in real time. These cells, not exceeding 15 passages, were seeded on E-plate 16 specific for a real time assay with the RTCA system (Real-Time Cell Analyzer, XCelligence, Roche) with a cell density of $5 \times 10^4$ cells/well. After 24 hours of cell incubation at 37° C. and 5% $CO_2$, the cell treatments for the control conditions (culture medium); XXO (10 μM xanthine/60 mU/mL xanthine oxidase); XXO plus G27 or G28 at 10, 40, 100, 400, 1000 or 4000 ng/ml, were performed. The cells were incubated (at 37° C. and 5% $CO_2$) with these treatments for 72 hours, was monitored every 10 minutes. The values that are obtained are arbitrary units indicated by the cell index, calculated from the impedance data, which is a electrical parameter that establishes the relationship between the voltage and current intensity of the adhered cells which is used as a measurement of cell viability.

Figure 15:
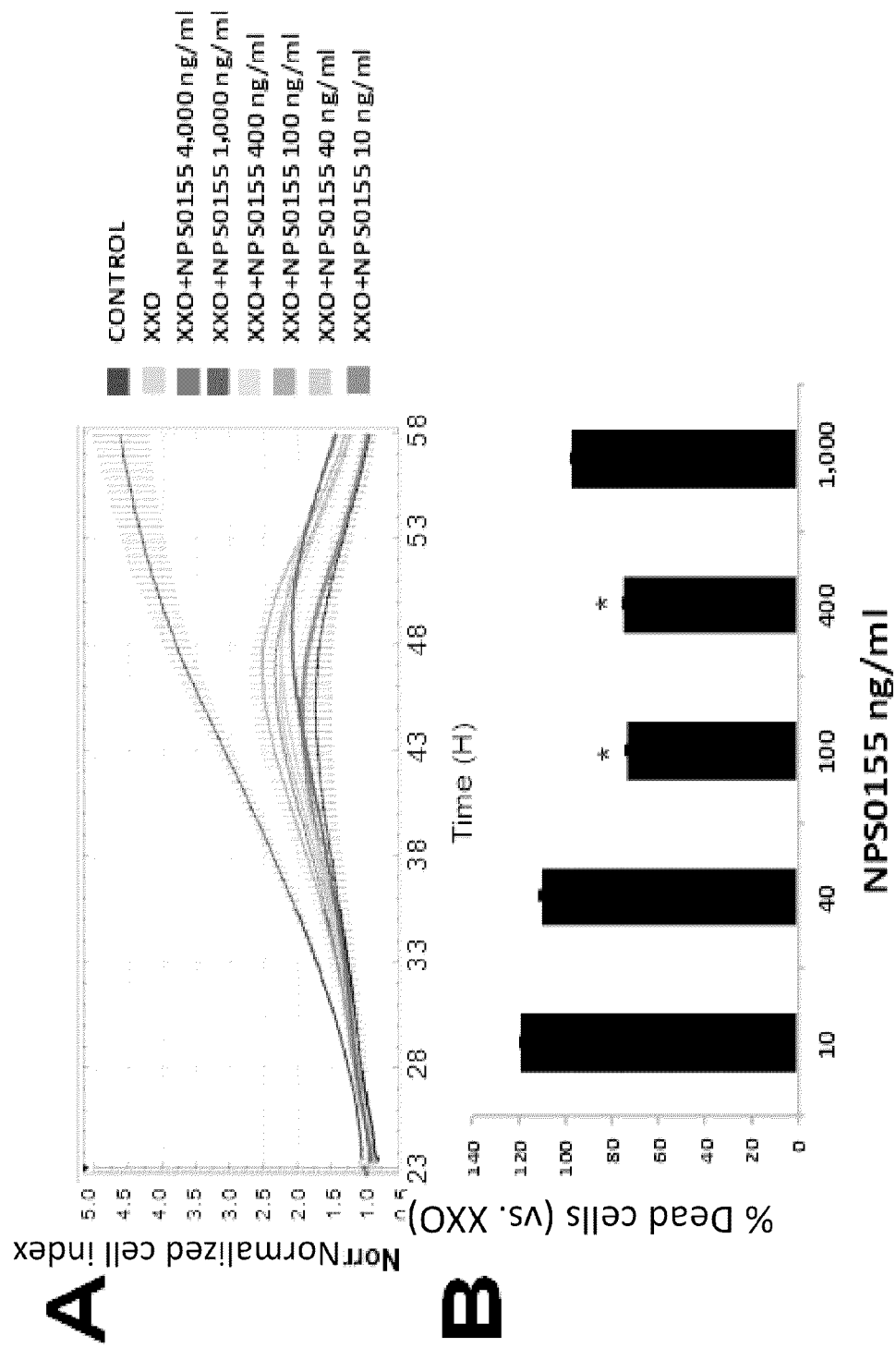
FIG. 15 shows in (A) the normalized cell index of SK-N-MC human neuroblastoma cells treated for 24 hours with XXO and several concentrations of NPS0155 (from 10 to 4,000 ng/ml). The XY scatter chart shows the real time measurement of a representative assay in measurements in duplicate; and in (B) the percentage of the normalized cell index relating to cells treated with XXO and with NPS0155 at the indicated concentrations at 20 hours post-treatment. The results are the mean±SEM of two assays performed in duplicate. * Significant difference with respect to treatment with XXO according to the Student's t test (p<0.05).

The results obtained for compound NPS0155 are shown in FIG. 15 as the normalized cell index (A) of each condition analyzed throughout treatment and as the percentage of cell death (B) for each treatment relating to death caused by XXO at 20 hours post-treatment. Protection against death by NPS0155 was observed in the range of 100 to 400 ng/ml, the maximum being 27% at 100 ng/ml, so this compound shows a protective effect against human neuronal cell death caused by oxidative stress.

Figure 16:
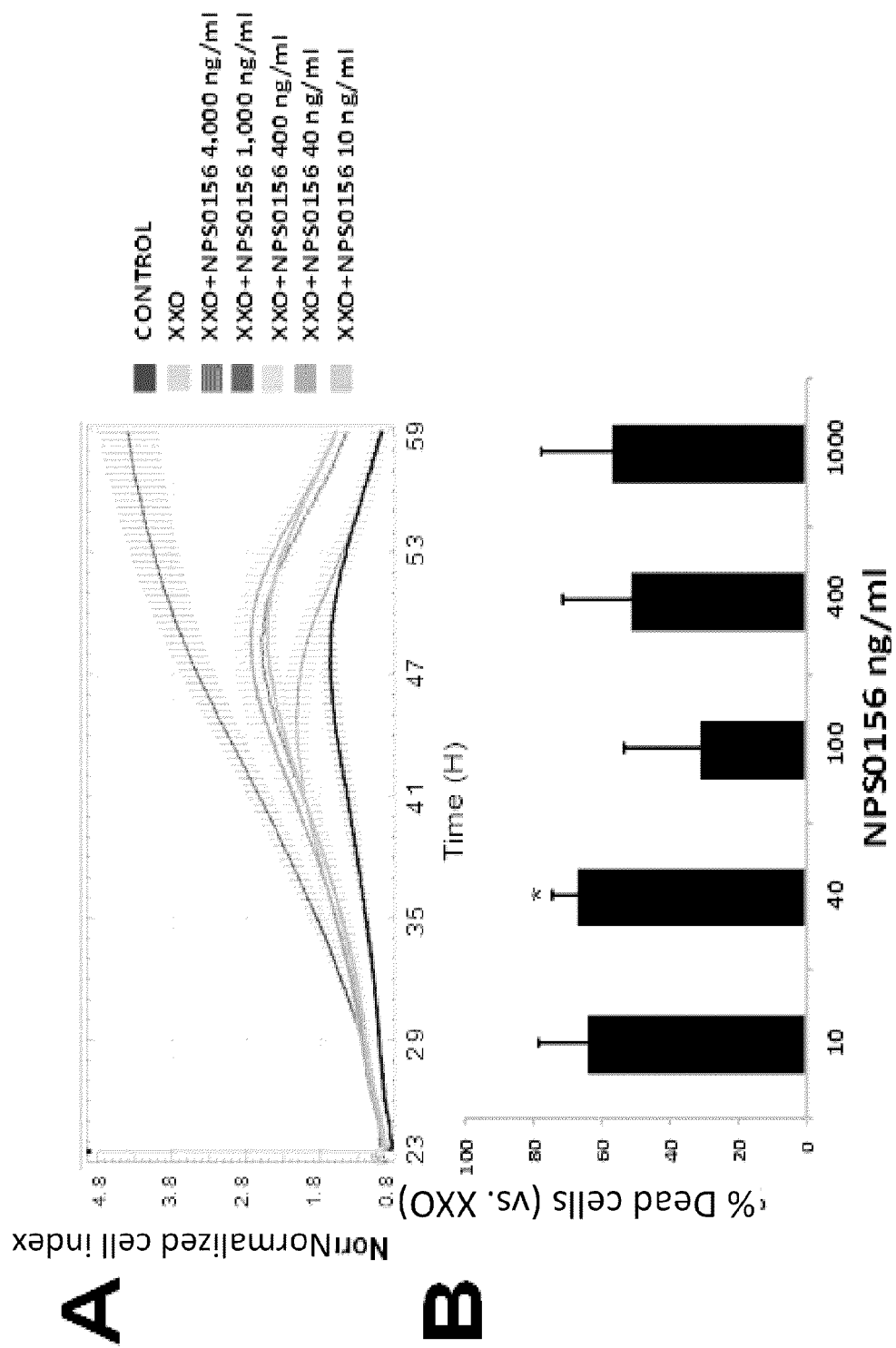
FIG. 16 shows in (A) the normalized cell index of SK-N-MC human neuroblastoma cells treated for 24 hours with XXO and several concentrations of NPS0156 (from 10 to 4,000 ng/ml). The XY scatter chart shows the real time measurement of a representative assay in measurements in duplicate; and in (B) the percentage of the normalized cell index relating to cells treated with XXO and with NPS0156 at the indicated concentrations at 20 hours post-treatment. The results are the mean±SEM of two assays performed in duplicate. * Significant difference with respect to treatment with XXO according to the Student's t test (p<0.05).

The results obtained for compound NPS0156 are shown in FIG. 16 as the normalized cell index (A) of each condition analyzed throughout treatment and as the percentage of cell death (B) for each treatment relating to death caused by XXO at 20 hours post-treatment. Protection against death by NPS0156 was observed in the range of 10 to 1.000 ng/ml, the maximum being 69% at 100 ng/ml, so this compound shows a protective effect against human neuronal cell death caused by oxidative stress.

EXAMPLE 7

Antioxidant Effect of Compounds NPS0155 (G27) and NPS0156 (G28)

Based on the preceding results, the researchers decided to analyze the in vitro antioxidant capacity of compounds NPS0155 and NPS0156 by means of the TEAC assay, described in Example 2. A standard curve with increasing concentrations of trolox (hydrosoluble vitamin E analogue) was used to quantify antioxidant capacity, such that the results are indicated as a measurement of trolox equivalents (TE). The assay on NPS0155 yielded 81±19 μM TE/μg of compound, which indicates that this compound shows in vitro antioxidant capacity. The assay on NPS0156 yielded 104±29 μM TE/μg of compound, which indicates that this compound shows in vitro antioxidant capacity.

EXAMPLE 8

Antiapoptotic Effect of Compounds NPS0155 and NPS0156 in Cells with Wild-Type and Mutated APP Based on the preceding results, the researchers decided to analyze the antiapoptotic effect of compounds NPS0155 and NPS0156. The assays were performed on two SK-N-MC human neuroblastoma culture cell lines stably transfected with constructs expressing the amyloid precursor protein (APP) gene encoding for the isoform primarily expressed in the brain, containing 695 amino acids cloned into the expression vector pcDNA3.1 (Invitrogen). One of the lines expresses the wild-type APP (APPwt) gene and the other line expresses the gene APP with the Swedish mutation (APPswe) which is a double mutation in exon 16 of the gene and produces a G to T transversion yielding the change of amino acid Lys595Asn and another A to C transversion causing the Met596Leu change, said mutation being related to the senile or hereditary forms of Alzheimer's disease. The cells were maintained as the parent cells SK-N-MC, as detailed in Example 2, using geneticin at 400 μg/ml as a selection antibiotic. To determine the effect of compounds NPS0155 and NPS0156 on apoptosis (programmed cell death), DNA fragmentation was analyzed by means of flow cytometry, produced by treatment with camptothecin (CPT) inhibiting the topoisomerase I enzyme, which impedes DNA duplication and triggers apoptotic cell death. The two cell lines, not exceeding 10 passages, were seeded on 12-well microtite plate treated for adherent cells with a cell density of $4 \times 10^5$ cells/well. After 24 hours of cell incubation at 37° C. and 5% $CO_2$, the pre-treatment of the cells with 4 and 10 μg/mL of NPS0155 or of NPS0156 for 24 hours was performed; they were subsequently treated with 50 μM CPT for 6 hours. After treatment, the cells were collected together with their culture medium and centrifuged at 300×g for 5 minutes. The medium was removed, the cells were washed with PBS solution and were fixed for 2 minutes with 500 μL of 70% ethanol at −20° C. Once they were fixed, they were centrifuged at 400×g for 5 minutes, washed with PBS and labeled with 0.05 mg/mL of propidium iodide, diluted in cycle buffer (0.1% citrate sodium, 0.3% Nonidet P-40 and 0.02 mg/mL RNAse), and were incubated for 1 hour at 37° C. They were maintained at 4° C. for 18 hours and after this time, they were analyzed by flow cytometry, measuring propidium iodide fluorescence as DNA content distribution.

Figure 17:
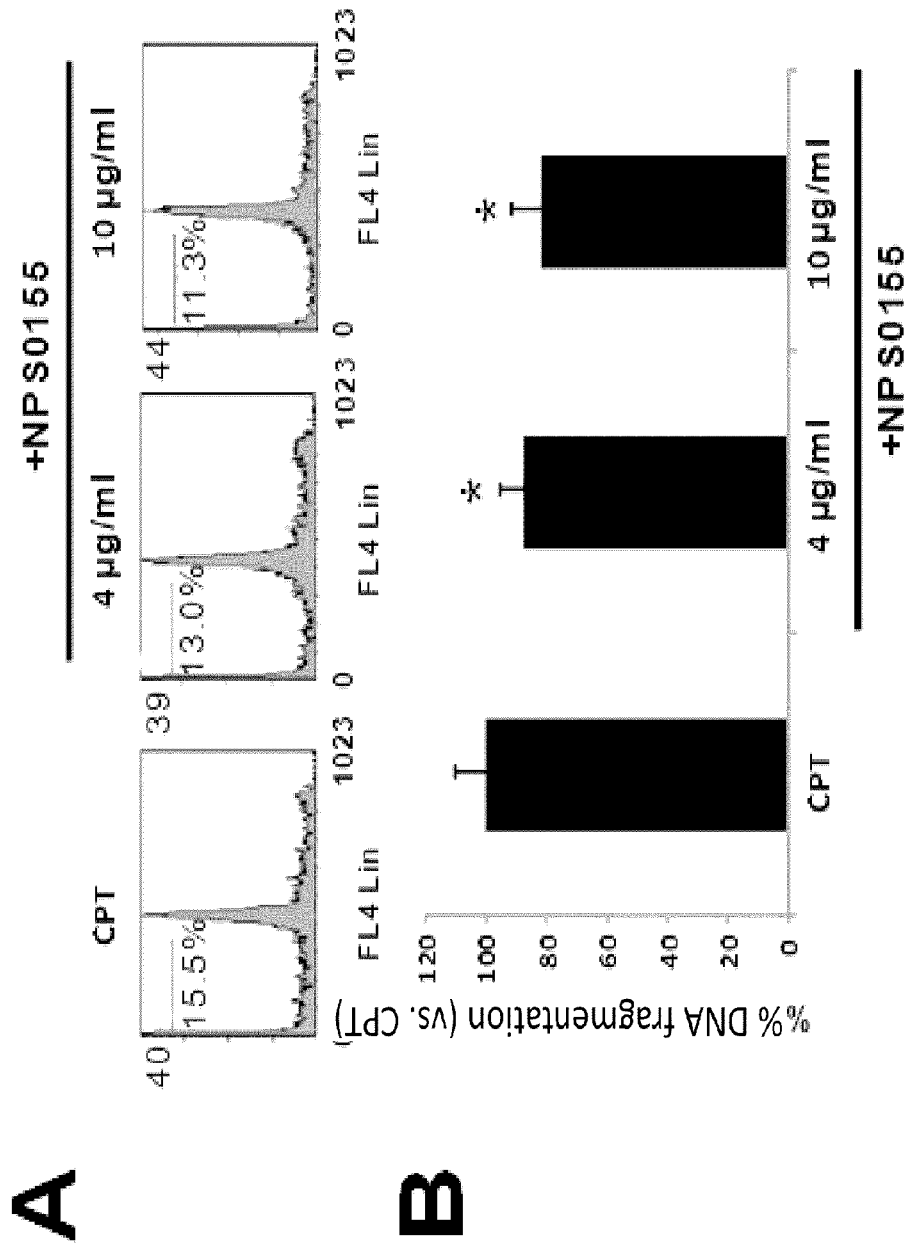
FIG. 17 shows in (A) the flow cytometry analysis of propidium iodide fluorescence with respect to the amount of DNA for cells carrying APP wild-type variant (APPwt) treated with 50 μM camptothecin (CPT) for 6 hours and for pre-treatment with NPS0155 for 24 hours at 4 and 10 μg/ml followed by treatment with CPT (the indicated percentage of apoptosis is measured on the sub-G1 region of each of the conditions); and in (B) the representative histograms showing the percentage of DNA fragmentation relating to APPwt cells treated with CPT and to pre-treatment with NPS0155 at 4 and 10 μg/ml, representing the means±SD of two independent experiments in sextuplicate. * Significant difference with respect to treatment with CPT according to the Student's t test (p<0.05).

The results obtained for compound NPS0155 in APPwt cells are included in FIG. 17, where the percentage of apoptosis in the sub-G1 region of each of the conditions (A), as well as the percentage of apoptosis inhibition of each treatment relating to apoptosis caused by CPT (B), are shown. Protection by NPS0155 was observed at the two tested doses in APPwt cells.

Figure 18:
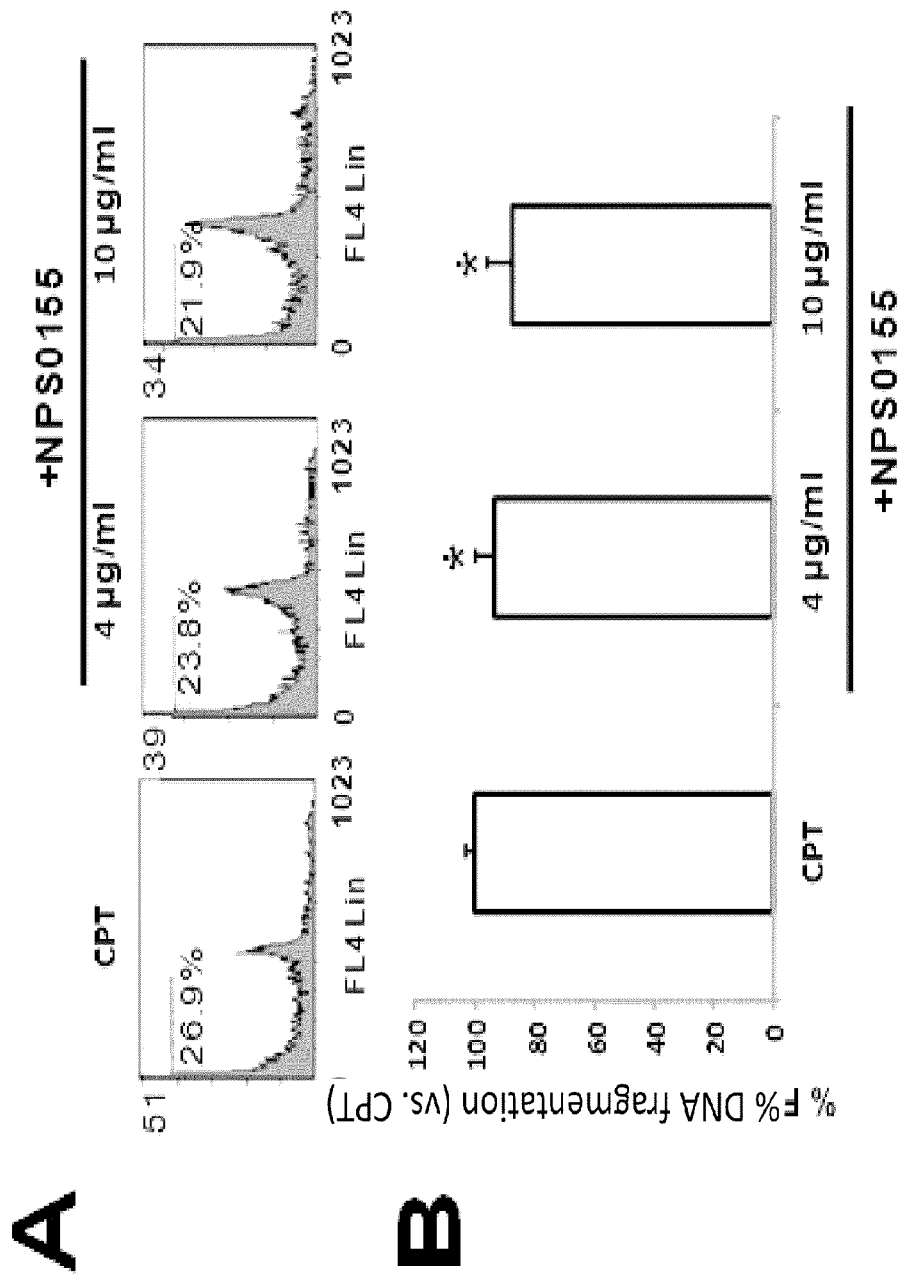
FIG. 18 shows in (A) the flow cytometry analysis of propidium iodide fluorescence with respect to the amount of DNA for cells carrying the APP Swedish mutant variant (APPswe) treated with 50 μM CPT for 6 hours and for pre-treatment with NPS0155 for 24 hours at 4 and 10 μg/ml followed by treatment with CPT (the indicated percentage of apoptosis is measured on the sub-G1 region of each of the conditions); and in (B) the representative histograms showing the percentage of DNA fragmentation relating to APPswe cells treated with CPT and to pre-treatment with NPS0155 at 4 and 10 μg/ml, representing the means±SD of two independent experiments in sextuplicate. * Significant difference with respect to treatment with CPT according to the Student's t test (p<0.05).

The results obtained for compound NPS0155 in APPswe cells are included in FIG. 18, where the percentage of apoptosis in the sub-G1 region of each of the conditions (A), as well as the percentage of apoptosis inhibition of each treatment relating to apoptosis caused by CPT (B), are shown. Protection by NPS0155 was observed at the two tested doses in APPswe cells.

Figure 19:
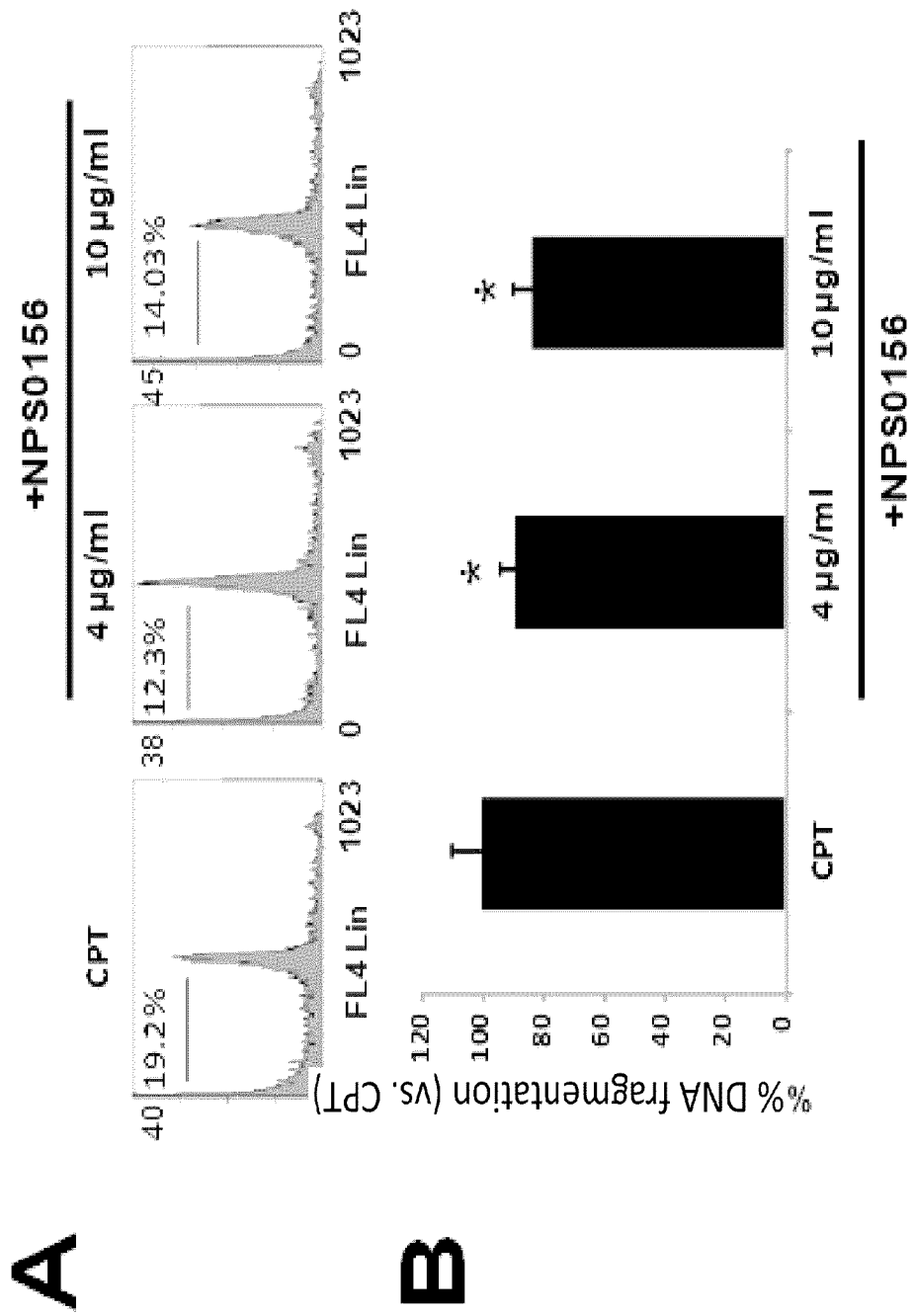
FIG. 19 shows in (A) the flow cytometry analysis of propidium iodide fluorescence with respect to the amount of DNA for cells carrying the APP wild-type variant (APPwt) treated with 50 μM CPT for 6 hours and for pre-treatment with NPS0156 for 24 hours at 4 and 10 μg/ml followed by treatment with CPT (the indicated percentage of apoptosis is measured on the sub-G1 region of each of the conditions); and in (B) the representative histograms showing the percentage of DNA fragmentation relating to APPwt cells treated with CPT and to pre-treatment with NPS0156 at 4 and 10 μg/ml, representing the means±SD of two independent experiments in sextuplicate. * Significant difference with respect to treatment with CPT according to the Student's t test (p<0.05).

The results obtained for compound NPS0156 in APPwt cells are included in FIG. 19, where the percentage of apoptosis in the sub-G1 region of each of the conditions (A), as well as the percentage of apoptosis inhibition of each treatment relating to apoptosis caused by CPT (B), are shown. Protection by NPS0156 was observed at the two tested doses in APPwt cells.

Figure 20:
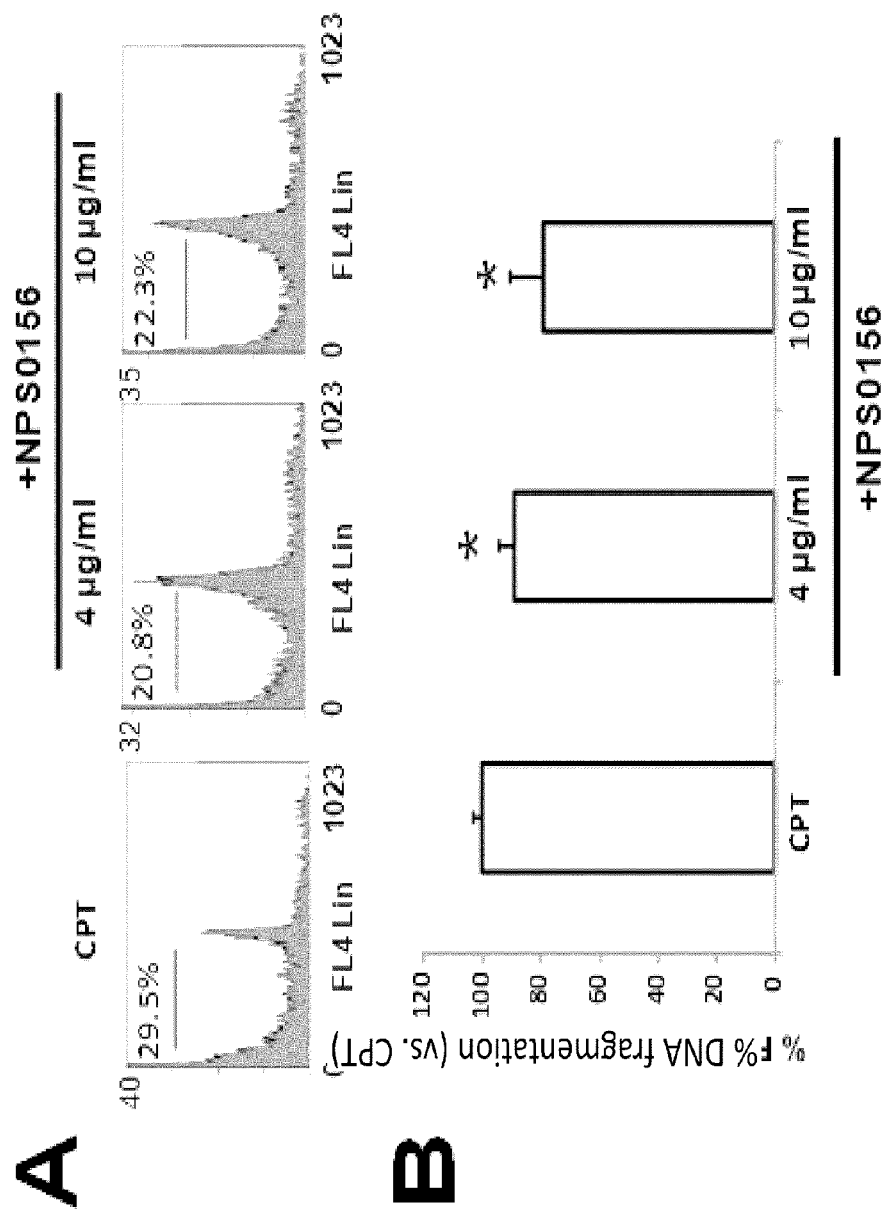
FIG. 20 shows in (A) the flow cytometry analysis of propidium iodide fluorescence with respect to the amount of DNA for cells carrying the APP Swedish mutant variant (APPswe) treated with 50 μM CPT for 6 hours and for pre-treatment with NPS0156 for 24 hours at 4 and 10 μg/ml followed by treatment with CPT (the indicated percentage of apoptosis is measured on the sub-G1 region of each of the conditions); and in (B) the representative histograms showing the percentage of DNA fragmentation relating to APPswe cells treated with CPT and to pre-treatment with NPS0156 at 4 and 10 μg/ml, representing the means±SD of two independent experiments in sextuplicate. * Significant difference with respect to treatment with CPT according to the Student's t test (p<0.05).

The results obtained for compound NPS0156 in APPswe cells are included in FIG. 20, where the percentage of apoptosis in the sub-G1 region of each of the conditions (A), as well as the percentage of apoptosis inhibition of each treatment relating to apoptosis caused by CPT (B), are shown. Protection by NPS0156 was observed at the two tested doses in APPswe cells.

In conclusion, this example shows that compounds NPS0155 and NPS0156 have a protective effect against apoptosis in human neuronal cells expressing wild-type and mutated APP.

EXAMPLE 9

Figure 21:
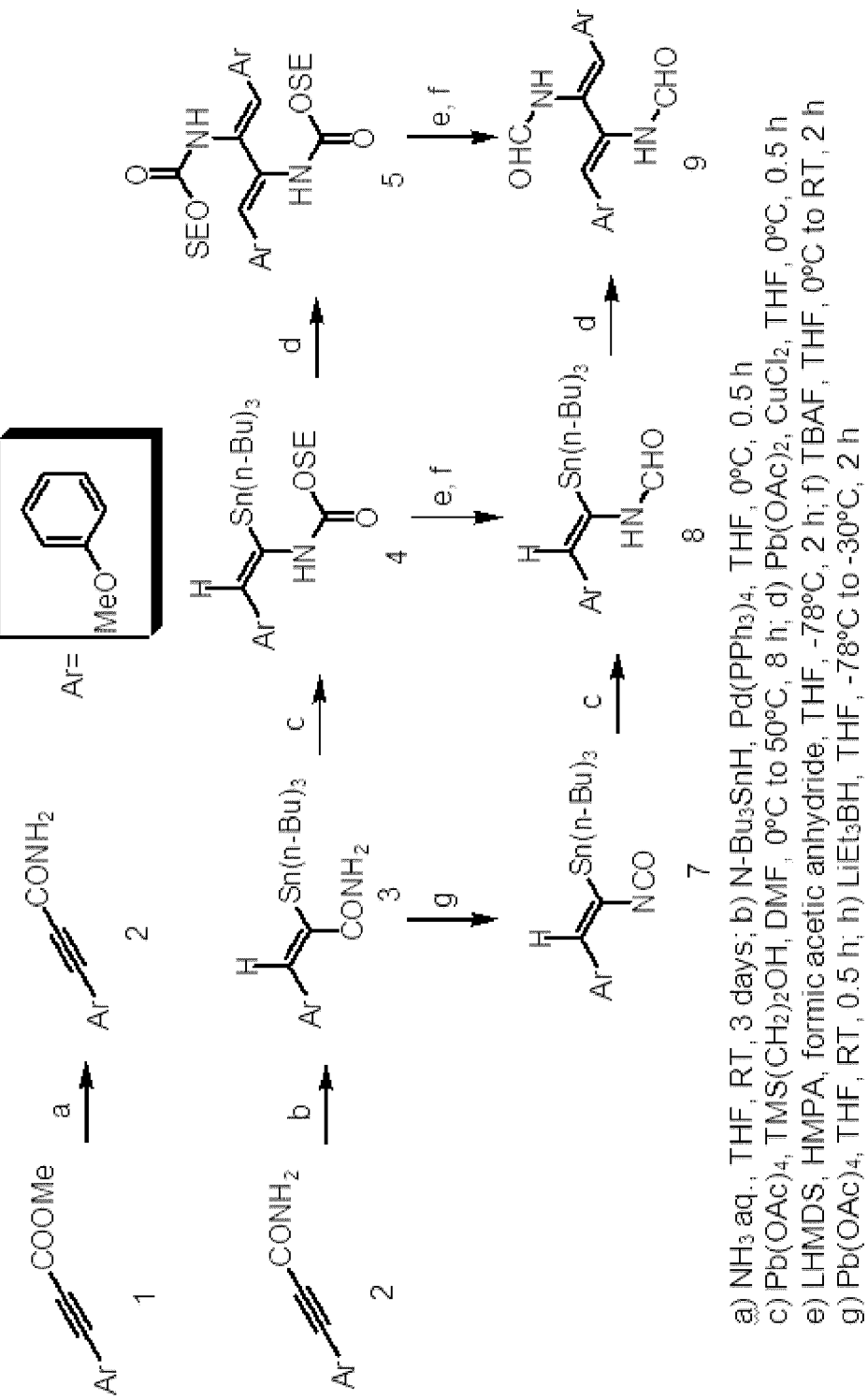
FIG. 21 shows the synthesis scheme of a xanthocillin X derivative as an example of the synthesis pathway for generating analogues of compound NPS0155. The steps that are indicated consist of: a. aqueous $NH_3$, THF, RT, 3 days; b. N-$Bu_3$SnH, Pd($PPh_3$)$_4$, THF, 0° C., 0.5 hours; c. Pb(OAc)$_4$, TMS($CH_2$)$_2$OH, DMF, 0° C. to 50° C., 8 hours; d. Pb(OAc)$_2$, $CuCL_2$, THF, 0° C., 0.5 hours; e. LHMDS, HMPA, acetic formic anhydride, THF, −78° C., 2 hours; f. TBAF, THF, 0° C. to RT, 2 hours; g. Pb(OAc)$_4$, THF, RT, 0.5 hours; h. $LiEt_3$BH, THF, −78 to −30° C., 2 hours.

Synthesis and Design of Xanthocillin Analogues with Neuroprotective Capacity 9.1. Synthesis of Xanthocillin Analogues Based on the preceding results, the inventors decided to design a process for synthesizing xanthocillin derivatives based on compound NPS0155, so the inventors used the synthesis of xanthocillin X with some modifications (Tatsuta et al. 2005. Tetrahedron Letters 46: 5017-20). The designed synthesis pathway is depicted in FIG. 21. Said synthesis consists of converting arylpropiolic acid ester (1) into its amide, (2); this amide (2) is converted into stannane (3) by adding tributyltin hydride. The carbamate (4), which has suitable stereochemistry to yield the product (5) by a palladium-catalyzed homo-coupling reaction, is obtained by Baumgarten oxidation. This product has the skeleton corresponding to the analogue type of interest. The purpose of the last two reactions is to deprotect the carbamates and introduce the formamido groups.

This synthesis strategy allows for certain flexibility. Alternatively to the 3→4→5→6 pathway, it can go from 3 to isocyanate 7 by means of Baumgarten oxidation (without trapping with silanol), convert 7 into the formamide 8 and then perform homo-coupling to give 6 (3→7→8→6 pathway), or also convert the carbamate 4 into the formamide 8 and then perform homo-coupling to give 6 (3→4→8→6 pathway).

The compound schematically shown in FIG. 22 is obtained by using the pathway described for xanthocillin X with some modifications, and the following groups for generating different analogues of compound G27 are introduced in positions Ar1 and Ar2:

hydroxyphenyl: 1 or 2 radicals (A and B) (e.g., 4-hydroxyphenyl)

methoxyphenyl: 1 or 2 radicals (C, D and E) (e.g., 4-methoxyphenyl)

1,3-benzodioxolyl (F) (e.g., 1,3-benzodioxol-5-yl)

methylphenyl: 1 or 2 radicals (G and H) (e.g., 4-methylphenyl)

ethylphenyl: 1 or 2 radicals (I and J) (e.g., 4-ethylphenyl)

phenyl (K)

alkoxyhydroxyphenyl: 1 or 2 radicals (L, M or N) (e.g., 3-hydroxy-4-methoxyphenyl or 3-hydroxy-4-ethoxyphenyl)

ethoxyphenyl: 1 or 2 radicals (O and P) (e.g., 4-ethoxyphenyl)

Studies on the combination of residues in the molecule of formula (II) were performed based on groups A to P described in FIG. 22, analyzing the effect of different structures on the theoretical lipophilicity index, which is essential for predicting the blood-brain barrier (BBB) crossing, which is a parameter that conditions the use of molecules as potential neuroprotective agents, as shown in FIG. 23.

9.2. Design of New Analogues Derived from Xanthocillin for Use as Neuroprotective Agents Based on the different derivatives shown in the preceding section, the inventors decided to analyze the lipophilicity of the combinations of substituents in positions Ar1 and Ar2 of formula (II). Lipophilicity was determined by the C LOG P value, defined as the log P of a compound, which is the partition coefficient between n-octanol and water, $\log(c_{octanol}/c_{water})$. The theoretical lipophilicity is essential for predicting the blood-brain barrier (BBB) crossing by passive diffusion, said crossing being greater the higher the C LOG P value. The C LOG P value results are shown in FIG. 23 and were calculated using the Osiris Property Explorer on-line application (http://www.organic-chemistry.org/prog/peo/). Surprisingly the different combinations in the residues considerably increase the C LOG P values, and therefore their potential BBB crossing, with respect to compounds NPS0155 (combination A+B) and NPS0156 (A+A).

9.3. Particular Synthesis of Compounds NPS0158 (G+G), NPS0159 (F+F), NPS0160 (P+P), NPS0161 (H+H) and NPS0163 (J+J)

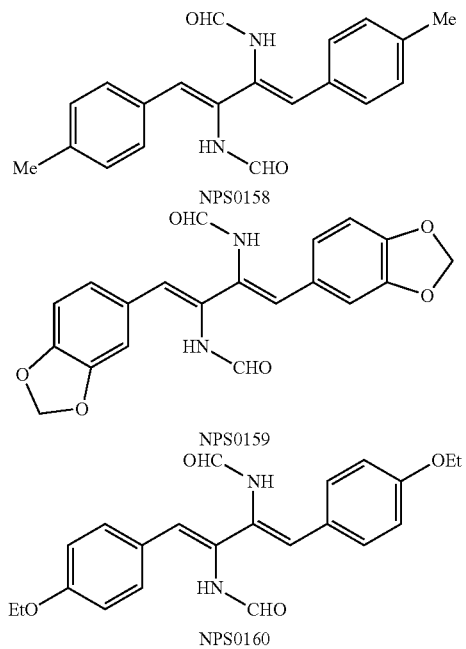

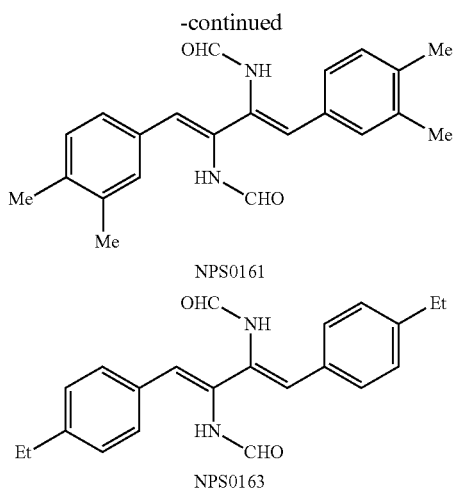

NPS0161

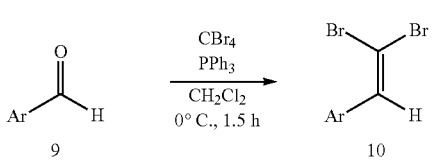

NPS0163

Figure 24:
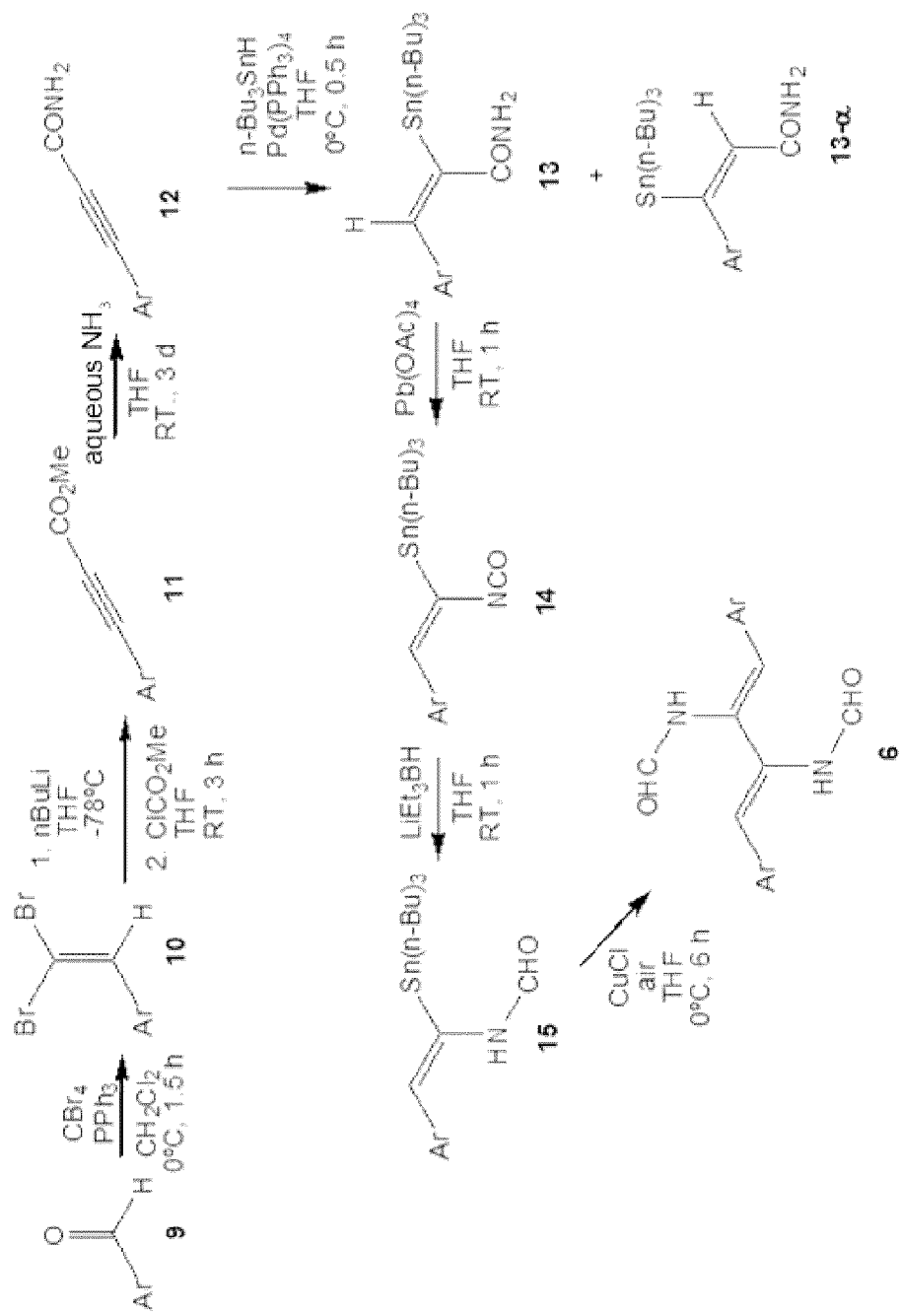
FIG. 24 shows the synthesis scheme of compounds NPS0158 (G+G), NPS0159 (F+F), NPS0160 (P+P), NPS0161 (H+ H) and NPS0163 (J+J).
Figure 25:
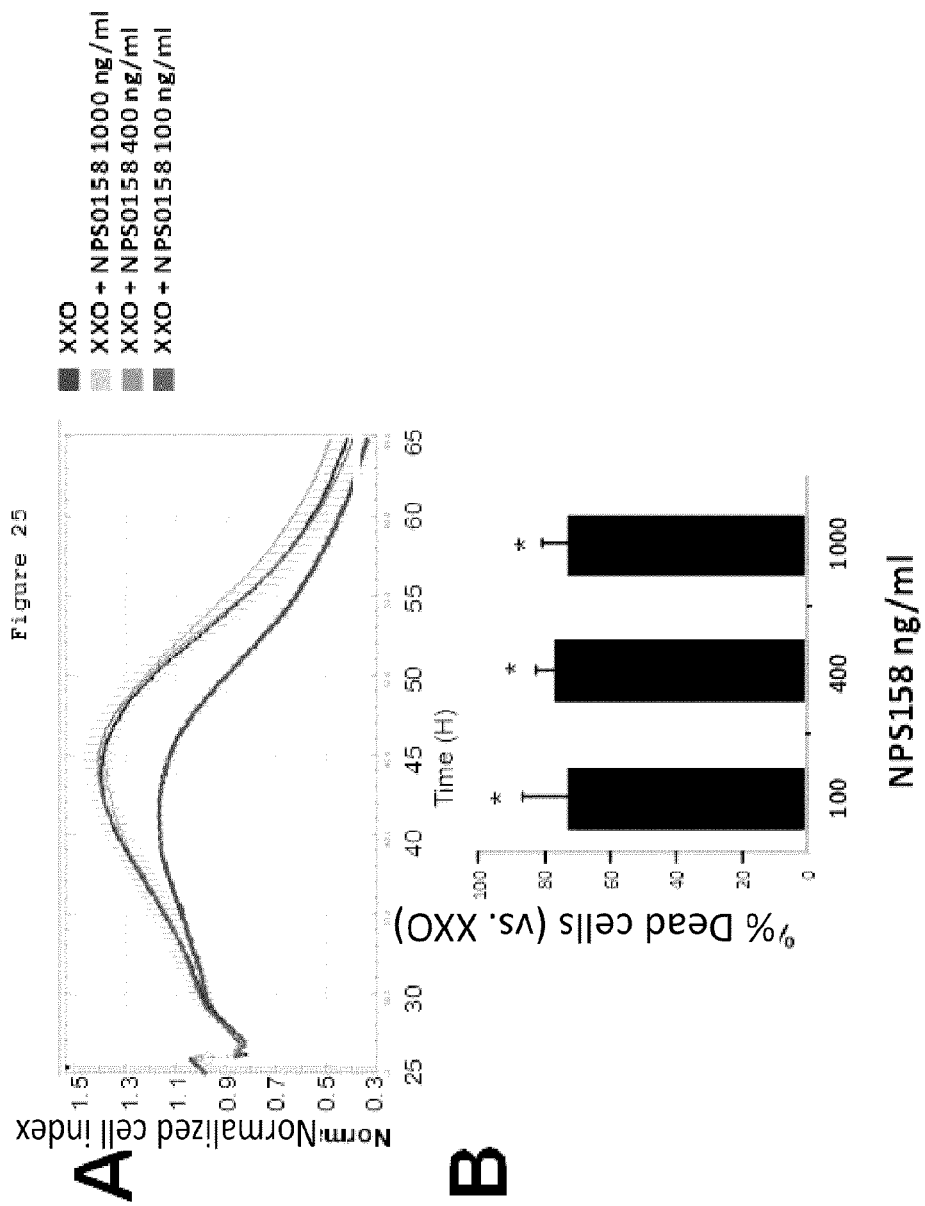
FIGS. 25-28 show in (A) the normalized cell index of SK-N-MC human neuroblastoma cells treated for 24 hours with XXO and several concentrations of the synthesized analogues (from 100 to 1000 ng/ml). The XY scatter chart shows the real time measurement of a representative assay in measurements in duplicate; and in (B) the percentage of the normalized cell index relating to cells treated with XXO and with the synthesized analogues at the indicated concentrations at 20 hours post-treatment.
Figure 26:
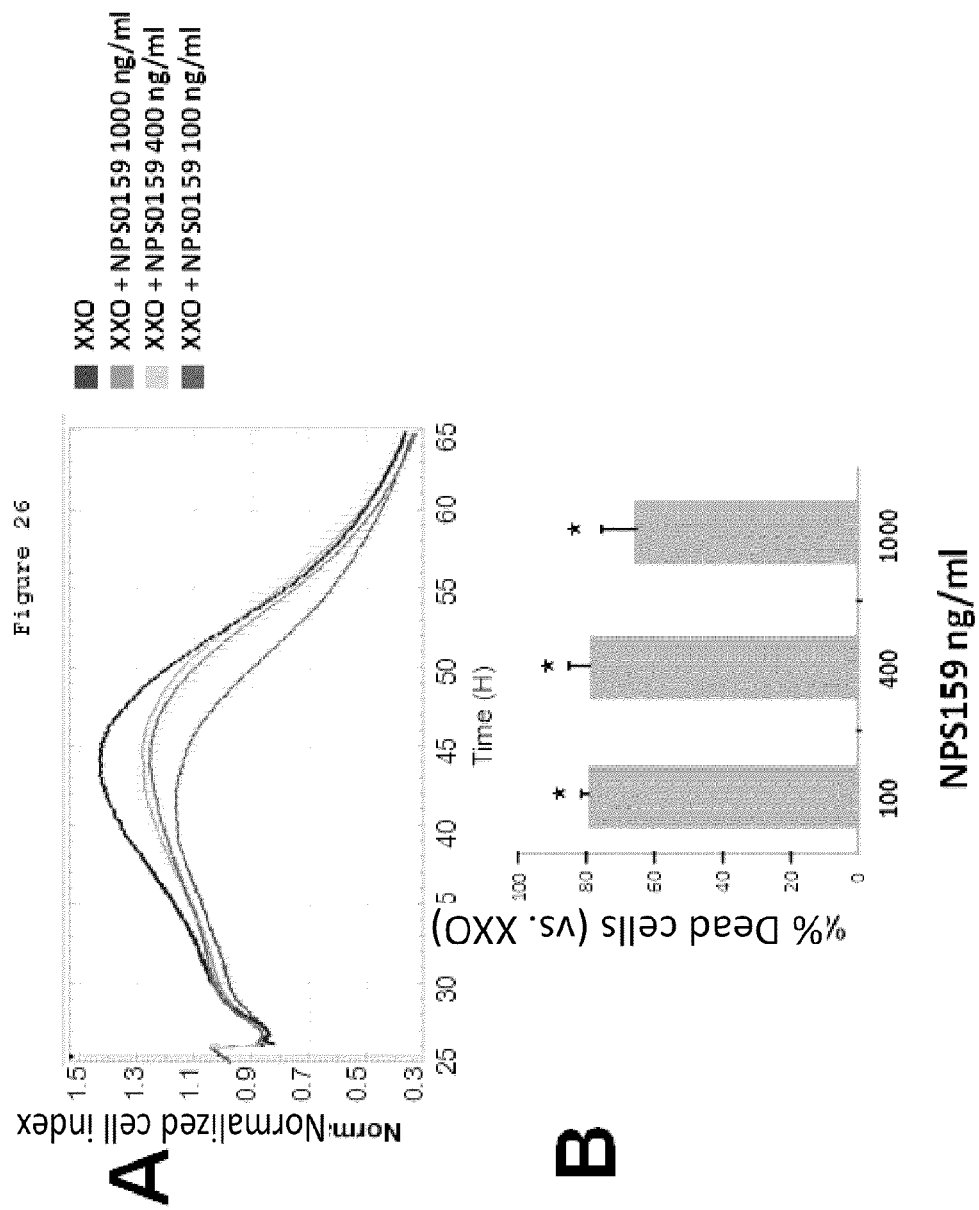
Figure 27:
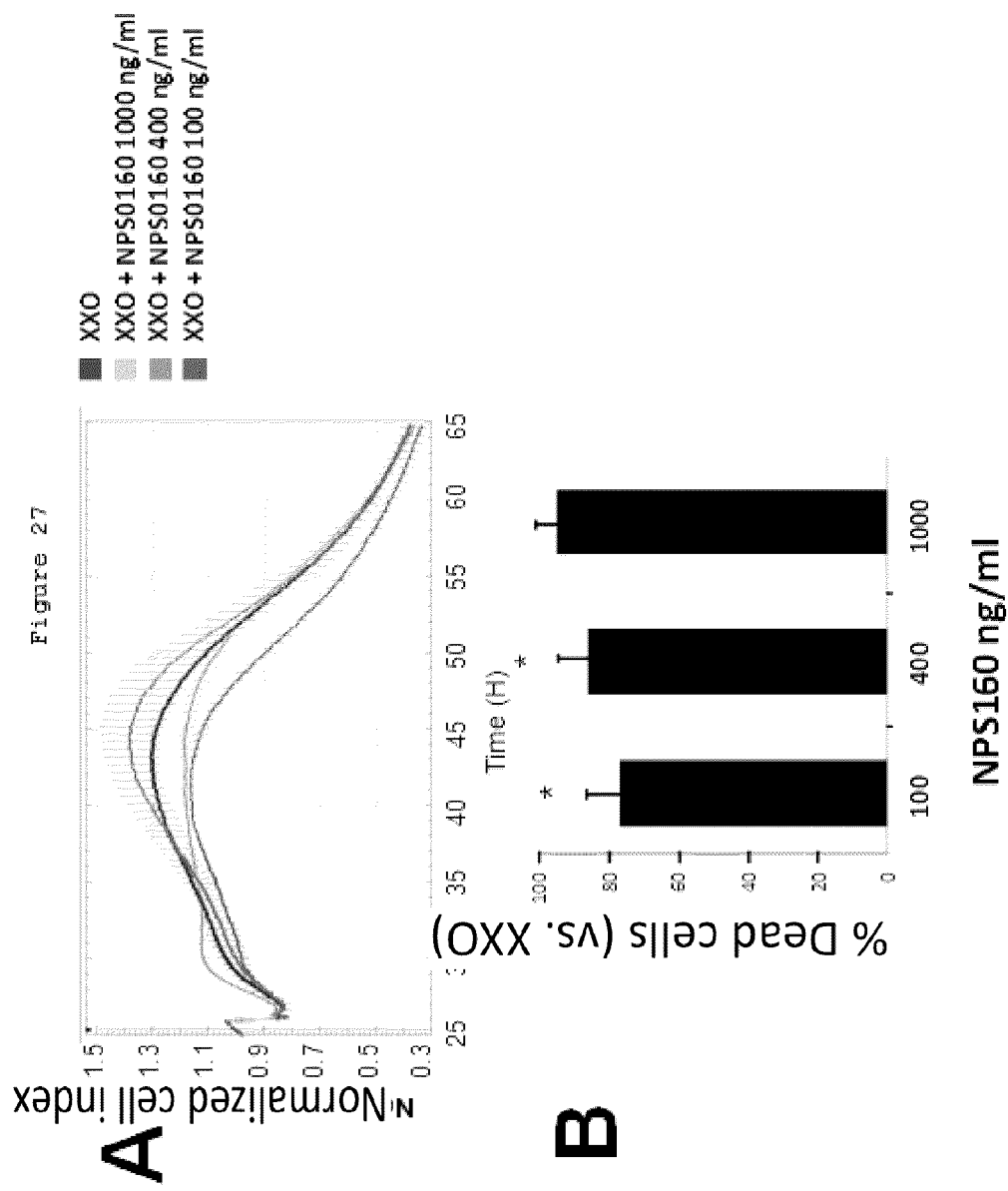
Figure 28:
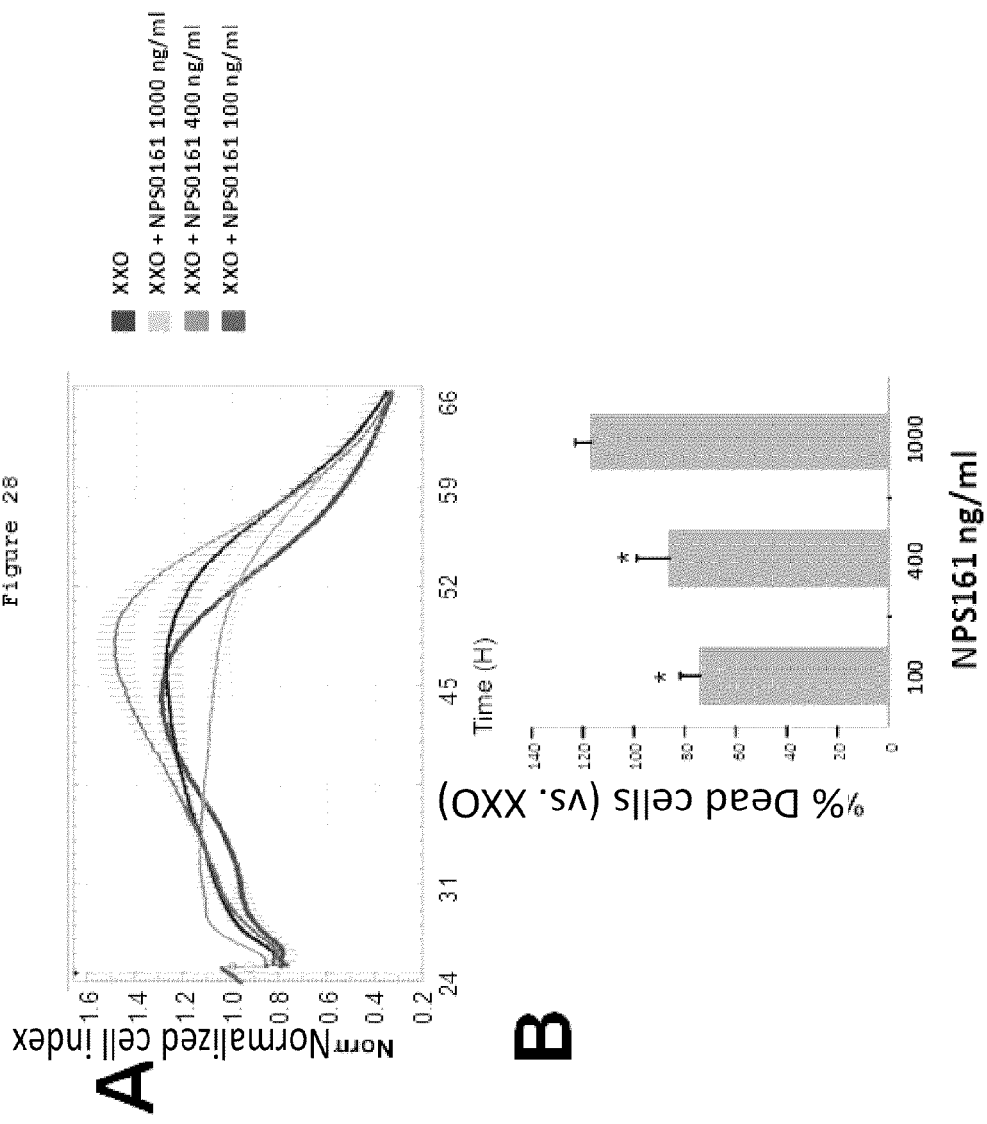

The pathway shown in FIG. 24 exemplifying the synthesis pathway described for the synthesis of the compounds of formula (II), is followed particularly for the synthesis of compounds NPS0158 (G+G), NPS0159 (F+F), NPS0160 (P+P), NPS0161 (H+H) and NPS0163 (J+J). Briefly, commercial aldehyde 9 is used as starting material, which was converted into alkyne 11 by means of a Corey-Fuchs reaction and trapped in situ by the acetylide recently formed with methyl chloroformate; the subsequent treatment with aqueous ammonia in THF allows isolating the propiolamide 12. Hydrostannylating the alkyne gives rise to the appearance of two regioisomers, primarily isomer 13, which is converted into isocyanate 14 by reaction with lead acetate (Baumgarten transposition), subsequently reducing it with superhydride. The stannyl derivative 15, which was dimerized in the presence of copper chloride, is thus obtained.

The following steps for the synthesis pathway to synthesize compounds NPS0158 (G+G), NPS0159 (F+F), NPS0160 (P+P), NPS0161 (H+H) and NPS0163 (J+J) are particularly followed.

9.3.1. Synthesis of Compounds 10 from Compounds 9:

General Method:

A solution of $CBr_4$ in $CH_2Cl_2$ (0.7 M) is added to a solution of $PPh_3$ in $CH_2Cl_2$ (1.7 M), cooled at 0° C., under argon atmosphere. The colorless solution turns to yellow and then to reddish color. It is left under stirring for 30 minutes at 0° C. Aldehyde 9 is then added dropwise, and it is left to react at 0° C. for 1.5 hours. It is diluted with $CH_2Cl_2$ (100 mL) and hexane (50 mL) is added precipitating triphenylphoshine oxide. It is vacuum-filtered and the solid is washed with more $CH_2Cl_2$/hexane mixture (2:1; 150 mL, ×2). The filtration waters are concentrated to dryness, yielding a solid which is suspended in $CH_2Cl_2$ and loaded in a silica gel chromatography column (100% $CH_2Cl_2$), yielding the desired compounds 10.

Synthesis of 1-(2,2-dibromovinyl)-4-methylbenzene

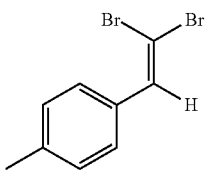

Following the general method, the mentioned compound is obtained at a quantitative yield (pale yellow solid), after 2 hours of reaction at 0° C., using 4-methylbenzaldehyde (3.05 g, 25.37 mmol), $PPh_3$ (29.94 g, 114.16 mmol) and $CBr_4$ (20.19 g, 60.89 mmol) as starting materials.

Synthesis of 5-(2,2-dibromovinyl)-1,3-benzodioxol

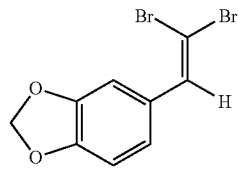 [SMILES: BrC(Br)=Cc1ccc2c(c1)OCO2]

Following the general method, the mentioned compound is obtained at a 97% yield (pale yellow oil), after 30 minutes of reaction at 0° C., using 1,3-benzodioxol-5-carbaldehyde (4.00 g, 26.64 mmol), $PPh_3$ (18.17 g, 69.27 mmol) and $CBr_4$ (11.49 g, 34.63 mmol) as starting materials.

Synthesis of 1-(2,2-dibromovinyl)-4-ethoxybenzene

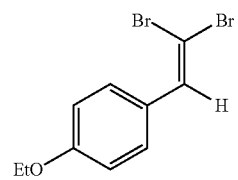 [SMILES: CCOc1ccc(C=C(Br)Br)cc1]

Following the general method, the mentioned compound is obtained at an 86% yield (pale yellow oil), after 1 hour of reaction at 0° C., using 4-ethoxybenzaldehyde (4.32 g, 28.76 mmol), $PPh_3$ (19.61 g, 74.78 mmol) and $CBr_4$ (12.40 g, 37.39 mmol) as starting materials.

Synthesis of 4-(2,2-dibromovinyl)-1,2-dimethylbenzene

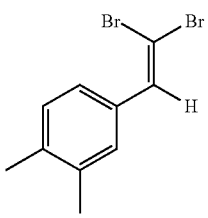

Following the general method, the mentioned compound is obtained at a 99% yield (pale yellow oil), after 2 hours of reaction at 0° C., using 3,4-dimethylbenzaldehyde (5.33 g, 39.73 mmol), PPh$_3$ (27.09 g, 103.30 mmol) and CBr$_4$ (17.13 g, 51.64 mmol) as starting materials.

Synthesis of 1-(2,2-dibromovinyl)-4-ethylbenzene

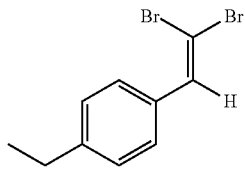

Following the general method, the mentioned compound is obtained at a 79% yield (pale yellow oil), after 3 hours of reaction at 0° C., using 4-ethylbenzaldehyde (5.00 g, 37.26 mmol), PPh$_3$ (25.41 g, 96.88 mmol) and CBr$_4$ (16.06 g, 48.44 mmol) as starting materials.

9.3.2. Synthesis of Compounds II from Compounds 10:

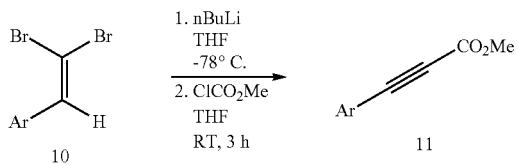

General Method:

N-BuLi (2.5 M in hexanes) is added dropwise to a solution of starting material 10 in THF (0.07 M), cooled at −78° C. The solution is left under stirring at this temperature for 1 hour. It is then left to reach RT (t=1 hour) and is cooled again at −78° C. ClCO$_2$Me is added; it is left to reach RT and stirred for 3 hours. Saturated aqueous NH$_4$Cl is added to pH=7, and it is then diluted with AcOEt (250 mL) and H$_2$O (100 mL). The organic phase is decanted, dried with anhydrous Na$_2$SO$_4$, filtered, the solvent is vacuum-removed and the residue is purified by means of silica gel column chromatography (0-5% AcOEt/hexanes) yielding the expected product 11.

Synthesis of methyl 3-(4-methylphenyl)prop-2-inoate

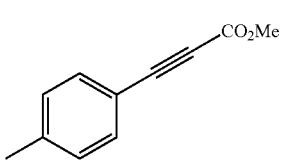

Following the general method, the mentioned compound is obtained at an 89% yield (pale yellow oil), using 1-(2,2-dibromovinyl)-4-methylbenzene (6.93 g, 25.11 mmol), n-BuLi (24 mL, 2.5 M in hexanes; 60.27 mmol) and ClCO$_2$Me (2.70 mL, 35.15 mmol), as starting materials.

Synthesis of methyl 3-(1,3-benzodioxol-5-yl)pro-2-inoate

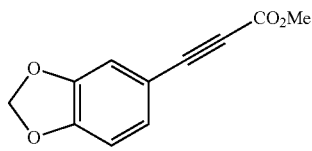 [SMILES: COC(=O)C#Cc1ccc2c(c1)OCO2]

Following the general method, the mentioned compound is obtained at an 84% yield (white solid), using 5-(2,2-dibromovinyl)-1,3-benzodioxol (7.85 g, 25.65 mmol), n-BuLi (20.5 mL, 2.5 M in hexanes; 51.32 mmol) and ClCO$_2$Me (2.78 mL, 35.91 mmol), as starting materials.

Synthesis of methyl 3-(4-ethoxyphenyl)prop-2-inoate

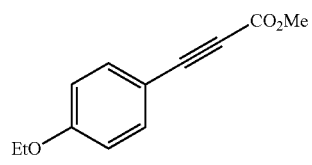

Following the general method, the mentioned compound is obtained at an 82% yield (solid yellow), using 1-(2,2-dibromovinyl)-4-ethoxybenzene (7.50 g, 24.0 mmol), n-BuLi (19.6 mL, 2.5 M in hexanes; 49.01 mmol) and ClCO$_2$Me (2.66 mL, 34.30 mmol), as starting materials.

Synthesis of methyl 3-(3,4-dimethylphenyl)prop-2-inoate

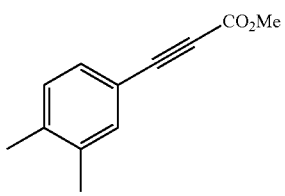

Following the general method, the mentioned compound is obtained at an 88% yield (brown oil), using 4-(2,2-dibromovinyl)-1,2-dimethylbenzene (11.40 g, 39.31 mmol), n-BuLi (31.5 mL, 2.5 M in hexanes; 78.62 mmol) and ClCO$_2$Me (4.26 mL, 55.03 mmol), as starting materials.

Synthesis of methyl 3-(4-ethylphenyl)prop-2-inoate

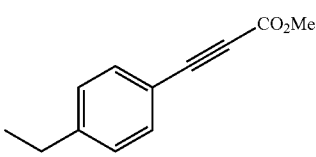

Following the general method, the mentioned compound is obtained at a 93% yield (pale yellow oil), using 1-(2,2- dibromovinyl)-4-ethylbenzene (8.50 g, 29.31 mmol), n-BuLi (23.4 mL, 2.5 M in hexanes; 58.60 mmol) and ClCO₂Me (3.18 mL, 41.03 mmol), as starting materials.

9.3.3. Synthesis of Compounds 12 from Compounds 11:

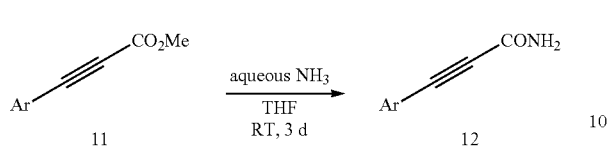

General Method:

NH₄OH (40 mL) is added to a solution of starting material 11 in THF (40 mL). The reaction is left under stirring at RT for 3 days. The solvents are removed to dryness and the obtained solid is ground with Et₂O (3×10 mL), yielding the desired product 12.

Synthesis of 3-(4-methylphenyl)prop-2-inamide

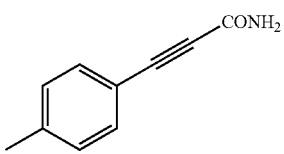

Following the general method, the mentioned compound is obtained at a quantitative yield (cream-colored solid), after 2 days of reaction, using methyl 3-(4-methylphenyl)prop-2-inoate (3.88 g, 22.27 mmol) as the starting material.

Synthesis of 3-(1,3-benzodioxol-5-yl)prop-2-inamide

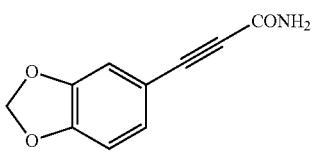 [SMILES: NC(=O)C#Cc1ccc2c(c1)OCO2]

Following the general method, the mentioned compound is obtained at a quantitative yield (white solid), after 3 days of reaction, using methyl 3-(1,3-benzodioxol-5-yl)prop-2-inoate (3.78 g, 18.51 mmol) as the starting material.

Synthesis of 3-(4-ethoxyphenyl)prop-2-inamide

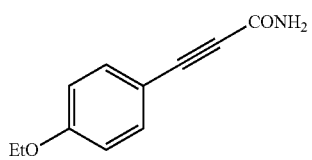 [SMILES: CCOc1ccc(C#CC(N)=O)cc1]

Following the general method, the mentioned compound is obtained at a 75% yield (white solid), after 3 days of reaction, using methyl 3-(4-ethoxyphenyl)prop-2-inoate (4.10 g, 20.07 mmol) as the starting material.

Synthesis of 3-(3,4-dimethylphenyl)prop-2-inamide

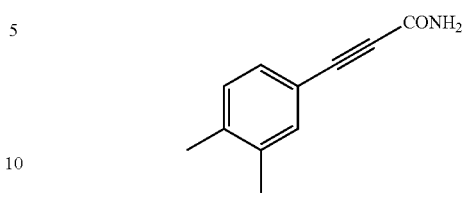

Following the general method, the mentioned compound is obtained at an 82% yield (white solid), after 1 day of reaction, using methyl 3-(3,4-dimethylphenyl)prop-2-inoate (6.52 g, 34.64 mmol) as the starting material.

Synthesis of 3-(4-ethylphenyl)prop-2-inamide

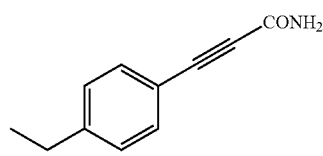

Following the general method, the mentioned compound is obtained at a quantitative yield (cream-colored solid), after 2 days of reaction, using methyl 3-(4-ethylphenyl)prop-2-inoate (5.10 g, 27.09 mmol) as the starting material.

9.3.4. Synthesis of Compounds 13 from Compounds 12:

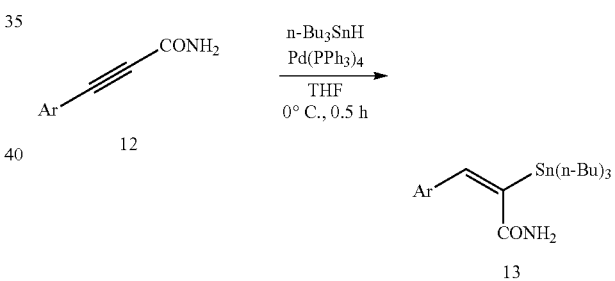

General Method:

Pd(PPh₃)₄ is added to a solution of starting material 12 in THF (80 mL), cooled at 0° C., and then Bu₃SnH is added dropwise. The reaction mixture is stirred at 0° C. for 30 minutes. The solvents are removed to dryness and the residue is purified by means of silica gel column chromatography (0-20% AcOEt/hexanes), yielding the expected product 13.

Synthesis of (E)-3-(4-methylphenyl)-2-(tributylstannyl)acrylamide

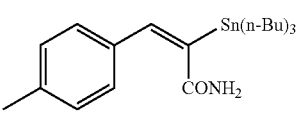

Following the general method, the mentioned compound is obtained at a 67% yield (brown oil), after 30 minutes of reaction at 0° C., using 3-(4-methylphenyl)prop-2-inamide (3.84 g, 29.27 mmol), Bu₃SnH (19.4 mL, 73.18 mmol) and Pd(PPh₃)₄ (1.69 g, 1.46 mmol) as starting materials.

Synthesis of (E)-3-(1,3-benzodioxol-5-yl)-2-(tributylstannyl)acrylamide

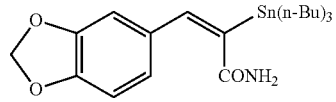

Following the general method, the mentioned compound is obtained at a 58% yield (yellow oil), after 3 hours of reaction at 0° C., using 3-(1,3-benzodioxol-5-yl)prop-2-inamide (3.82 g, 23.71 mmol), Bu₃SnH (6.90 mL, 25.98 mmol) and Pd(PPh₃)₄ (0.50 g, 0.43 mmol) as starting materials.

Synthesis of (E)-3-(4-ethoxyphenyl)-2-(tributylstannyl)acrylamide

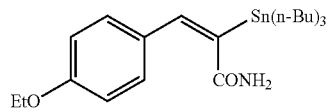

Following the general method, the mentioned compound is obtained at a 76% yield (yellow oil), after 2 hours of reaction at 0° C., using 3-(4-ethoxyphenyl)prop-2-inamide (2.35 g, 12.42 mmol), Bu₃SnH (3.95 mL, 14.90 mmol) and Pd(PPh₃)₄ (0.29 g, 0.25 mmol) as starting materials.

Synthesis of (E)-3-(3,4-dimethylphenyl)-2-(tributylstannyl)acrylamide

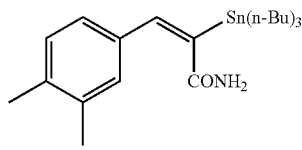

Following the general method, the mentioned compound is obtained at a 54% yield (yellow oil), after 2 hours of reaction at 0° C., using 3-(3,4-dimethylphenyl)prop-2-inamide (4.10 g, 28.23 mmol), Bu₃SnH (9.00 mL, 33.88 mmol) and Pd(PPh₃)₄ (0.65 g, 0.56 mmol) as starting materials.

Synthesis of (E)-3-(4-ethylphenyl)-2-(tributylstannyl)acrylamide

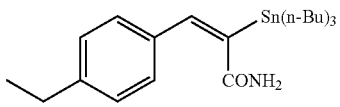

Following the general method, the mentioned compound is obtained at a 72% yield (yellow oil), after 1.5 hours of reaction at 0° C., using 3-(4-ethylphenyl)prop-2-inamide (3.93 g, 27.06 mmol), Bu₃SnH (8.60 mL, 32.47 mmol) and Pd(PPh₃)₄ (0.62 g, 0.54 mmol) as starting materials.

9.3.5. Synthesis of Compounds 14 from Compounds 13:

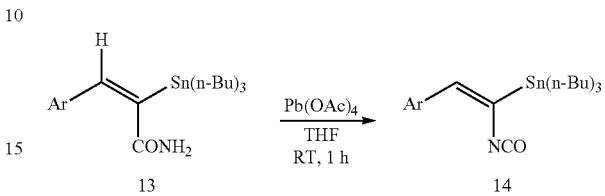

General Method:

Pb(OAc)₄ is added to a solution of starting material 13 in THF (140 mL), cooled at 0° C. It is left to reach RT and stirred for 1 hour. It is then diluted with H₂O (100 mL) and AcOEt (100 mL). The organic phase is decanted and the aqueous phase is extracted with more AcOEt (2×100 mL). The combined organic phases are dried with anhydrous Na₂SO₄, filtered, the solvent is vacuum-removed and the residue is purified by silica gel column chromatography (0-5% AcOEt/hexanes) yielding the expected product 14.

Synthesis of (E)-tributyl[1-isocyanate-2-(4-methylphenyl)vinyl]stannane

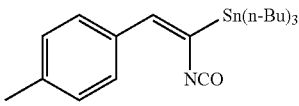

Following the general method, the mentioned compound is obtained at a 38% yield (yellow oil), after 1 hour of reaction at room temperature, using (E)-3-(4-methylphenyl)-2-(tributylstannyl)acrylamide (8.81 g, 19.57 mmol) and Pb(OAc)₄ (10.40 g, 23.48 mmol) as starting materials.

Synthesis of (E)-tributyl[1-isocyanate-2-(1,3-benzodioxol-5-yl)vinyl]stannane

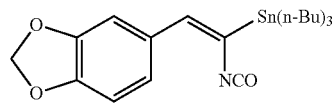

Following the general method, the mentioned compound is obtained at a quantitative yield (impure yellow oil), after 2 hours of reaction at room temperature, using (E)-3-(1,3-benzodioxol-5-yl)-2-(tributylstannyl)acrylamide (6.01 g, 12.60 mmol) and Pb(OAc)₄ (6.70 g, 15.11 mmol) as starting materials.

Synthesis of (E)-tributyl[1-isocyanate-2-(4-ethoxyphenyl)vinyl]stannane

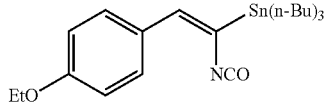

Following the general method, the mentioned compound is obtained at a 38% yield (yellow oil), after 1.5 hours of reaction at room temperature, using (E)-3-(4-ethoxyphenyl)-2-(tributylstannyl)acrylamide (4.51 g, 9.40 mmol) and Pb(OAc)$_4$ (5.00 g, 11.27 mmol) as starting materials.

Synthesis of (E)-tributyl[1-isocyanate-2-(3,4-dimethylphenyl)vinyl]stannane

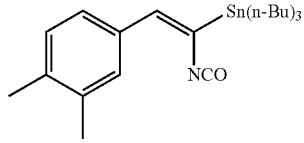

Following the general method, the mentioned compound is obtained at a 49% yield (yellow oil), after 4 hours of reaction at room temperature, using (E)-3-(3,4-dimethylphenyl)-2-(tributylstannyl)acrylamide (6.98 g, 15.03 mmol) and Pb(OAc)$_4$ (8.00 g, 18.04 mmol) as starting materials.

Synthesis of (E)-tributyl[1-isocyanate-2-(4-ethylphenyl)vinyl]stannane

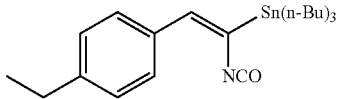

Following the general method, the mentioned compound is obtained at a 57% yield (yellow oil), after 5 hours of reaction at room temperature, using (E)-3-(4-ethylphenyl)-2-(tributylstannyl)acrylamide (8.95 g, 19.28 mmol) and Pb(OAc)$_4$ (10.26 g, 23.13 mmol) as starting materials.

9.3.6. Synthesis of Compounds 15 from Compounds 14:

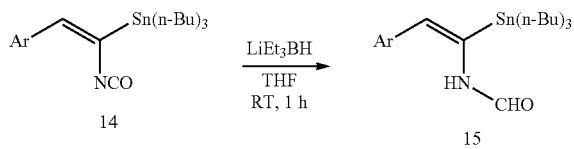

General Method:

LiEt$_3$BH (1M in THF) is added dropwise, under argon atmosphere, to a solution of starting material 14 in THF (100 mL), cooled at −78° C. It is heated at −40° C. and left to react for 2 hours at this temperature. It is then left to reach RT and saturated aqueous NaHCO$_3$ is added until reaching pH=7. Et$_2$O (100 mL) is added, the organic phase is decanted, dried with anhydrous Na$_2$SO$_4$, filtered, the solvent is vacuum-removed and the residue is purified by means of silica gel column chromatography (0-10% AcOEt/hexanes), yielding the expected product 15.

Synthesis of (E)-N-[2-(4-methylphenyl)-1-tributylstannyl)vinyl]formamide

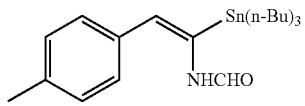

Following the general method, the mentioned compound is obtained at a 95% yield (colorless oil), after 1.5 hours of reaction, using (E)-tributyl[1-isocyanate-2-(4-methylphenyl)vinyl]stannane (3.31 g, 7.38 mmol) and LiEt$_3$BH (8.12 mL, 1 M in THF; 8.12 mmol) as starting materials.

Synthesis of (E)-N-[2-(1,3-benzodioxol-5-yl)-1-tributylstannyl)vinyl]formamide

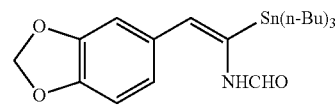

Following the general method, the mentioned compound is obtained at an 18% yield (brown oil), after 1 hour of reaction, using (E)-tributyl[1-isocyanate-2-(1,3-benzodioxol-5-yl)vinyl]stannane (6.03 g, 12.60 mmol) and LiEt$_3$BH (13.23 mL, 1 M in THF; 13.23 mmol) as starting materials.

Synthesis of (E)-N-[2-(4-ethoxyphenyl)-1-tributylstannyl)vinyl]formamide

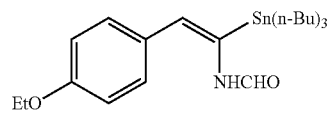

Following the general method, the mentioned compound is obtained at a 51% yield (yellow oil), after 1 hour of reaction, using (E)-tributyl[1-isocyanate-2-(4-ethoxyphenyl)vinyl]stannane (2.01 g, 4.20 mmol) and LiEt$_3$BH (4.41 mL, 1 M in THF; 4.41 mmol) as starting materials.

Synthesis of (E)-N-[2-(3,4-dimethylphenyl)-1-tributylstannyl)vinyl]formamide

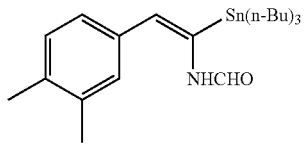

Following the general method, the mentioned compound is obtained at an 82% yield (yellow oil), after 35 minutes of reaction, using (E)-tributyl[1-isocyanate-2-(3,4-dimethylphenyl)vinyl]stannane (3.40 g, 7.35 mmol) and LiEt$_3$BH (7.72 mL, 1 M in THF; 7.72 mmol) as starting materials.

Synthesis of (E)-N-[2-(4-ethylphenyl)-1-tributylstannyl)vinyl]formamide

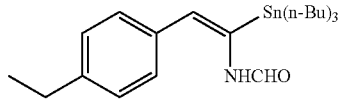

Following the general method, the mentioned compound is obtained at a 97% yield (yellow oil), after 1 hour of reaction, using (E)-tributyl[1-isocyanate-2-(4-ethylphenyl)vinyl]stannane (5.10 g, 11.03 mmol) and LiEt$_3$BH (11.58 mL, 1 M in THF; 11.58 mmol) as starting materials.

9.3.7. Synthesis of Compounds 6 from Compounds 15:

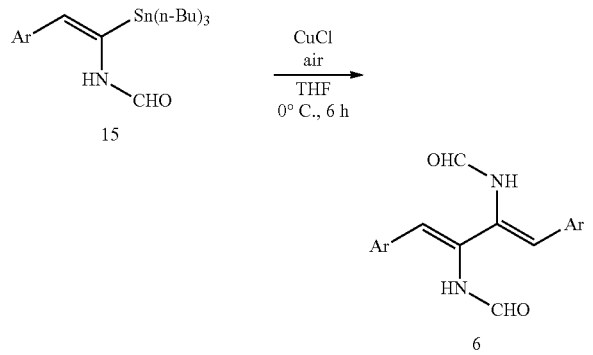

General Method:

CuCl is added to a solution of starting material 15 in THF (30 mL), cooled at 0° C. An air stream is then bubbled into the suspension, while the temperature is maintained for 6 hours. The mixture is diluted with Et$_2$O (100 mL) and filtered through celite eluting with Et$_2$O (4×20 mL). The filtration waters are concentrated to dryness, and the green solid is suspended in CH$_2$Cl$_2$ (100 mL) and washed with 10% aqueous NH$_4$OH until the washings come out colorless (7×70 mL). The organic phase is dried with anhydrous Na$_2$SO$_4$, filtered, the solvent is vacuum-removed and the residue is purified by means of silica gel column chromatography (0-2% MeOH/CH$_2$Cl$_2$). A solid ground with Et$_2$O (+drops of MeOH) is obtained, yielding the expected product 6.

Synthesis of NPS0158, (1Z,2Z)-2-(formylamino)-1-(4-methylbenzylidene)-3-(4-methylphenyl)prop-2-enylformamide

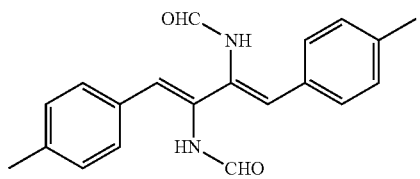

Following the general method, the mentioned compound is obtained at an 8% yield (white solid), after 4 hours of reaction, using (E)-N-[2-(4-methylphenyl)-1-(tributylstannyl)vinyl]formamide (3.14 g, 6.97 mmol) and CuCl (2.07 g, 20.91 mmol) as starting materials.

$^1$H-NMR (DMSO-d$_6$, 250 MHz) δ ppm: Rotamer mixture:

9.70-9.26 (m, 2H, CHO); [8.19 (s)+7.91-7.73 (m)] (2H, NH); 7.53-7.07 (m, 8H, ArH); 6.64-6.48 (m, 2H, alkene); 2.30 (s, 6H, CH$_3$).

Synthesis of NPS0159, (1Z,2Z)-3-(1,3-benzodioxol-5-yl)-1-(1,3-benzodioxol-5-ylmethylen)-2-(formylamino)prop-2-enylformamide

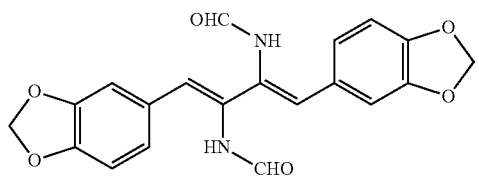 [SMILES: O=CNC(=C\c1ccc2c(c1)OCO2)/C(=C/c1ccc2c(c1)OCO2)NC=O]

Following the general method, the mentioned compound is obtained at a 25% yield (white solid), after 2 hours of reaction, using (E)-N-[2-(1,3-benzodioxol-5-yl)-1-(tributylstannyl)vinyl]formamide (0.50 g, 1.04 mmol) and CuCl (0.31 g, 3.12 mmol) as starting materials.

The purification described in the general method is varied: the reaction mixture is suspended in Me-THF (60 mL) and washed with an aqueous ammonia solution (10%, 20 mL×3). The organic phase is concentrated to dryness, obtaining a white solid which is ground with EtOH and with Et$_2$O.

$^1$H-NMR (DMSO-d$_6$, 250 MHz) δ ppm: Rotamer mixture:

9.62-9.28 (m, 2H, CHO); [8.18 (s)+7.91-7.73 (m)] (2H, NH); 7.20-6.85 (m, 6H, ArH); 6.56-6.44 (m, 2H, alkene); 6.03 (s, 4H, CH$_2$).

Synthesis of NPS0160, (1Z,2Z)-2-(formylamino)-1-(4-ethoxybenzylidene)-3-(4-ethoxyphenyl)prop-2-enylformamide

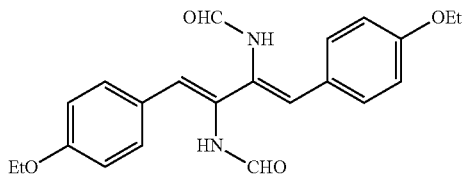 [SMILES: CCOc1ccc(/C=C(NC=O)/C(=C/c2ccc(OCC)cc2)NC=O)cc1]

Following the general method, the mentioned compound was obtained at a 39% yield (white solid), after 3 hours of reaction, using (E)-N-[2-(4-ethoxyphenyl)-1-(tributylstannyl)vinyl]formamide (1.03 g, 2.15 mmol) and CuCl (0.43 g, 4.29 mmol) as starting materials.

The purification described in the general method is varied: the reaction mixture is suspended in Me-THF (60 mL) and washed with an aqueous ammonia solution (10%, 30 mL×3). The organic phase is concentrated to dryness, obtaining a white solid which is ground with MeOH and with Et$_2$O.

$^1$H-NMR (DMSO-d$_6$, 250 MHz) δ ppm: Rotamer mixture:

9.60-9.27 (m, 2H, CHO); [8.18 (s)+7.90-7.75 (m)] (2H, NH); 7.52-6.85 (m, 8H, ArH); 6.56-6.46 (m, 2H, alkene); 4.02 (q, J=6.8 Hz, 4H, CH$_2$); 1.31 (t, J=6.8 Hz, 6H, CH$_3$).

Synthesis of NPS0161, (1Z,2Z)-1-(3,4-dimethylbenzylidene)-3-(3,4-dimethylphenyl)-2-(formylamino)-prop-2-enylformamide

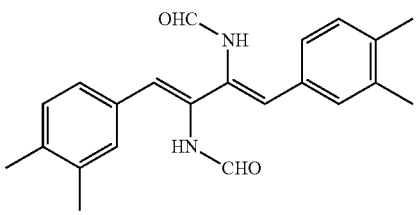

Following the general method, the mentioned compound is obtained at a 55% yield (white solid), after 1 hour of reaction, using (E)-N-[2-(3,4-dimethylphenyl)-1-(tributylstannyl)vinyl]formamide (1.38 g, 2.97 mmol) and CuCl (0.59 g, 5.95 mmol) as starting materials.

The purification described in the general method is varied: the reaction mixture is suspended in Me-THF (50 mL) and washed with an aqueous ammonia solution (10%, 50 mL×3). The organic phase is concentrated to dryness, obtaining a white solid which is ground with EtOH and with Et$_2$O.

$^1$H-NMR (DMSO-d$_6$, 250 MHz) δ ppm: Rotamer mixture:

9.69-9.28 (m, 2H, CHO); [8.19 (s)+7.90-7.70 (m)] (2H, NH); 7.38-7.03 (m, 6H, ArH); 6.62-6.42 (m, 2H, alkene); 2.20 (s, 12H, CH$_3$).

Synthesis of NPS0163, (1Z,2Z)-2-(formylamino)-1-(4-ethylbenzylidene)-3-(4-ethylphenyl)-prop-2-enyl-formamide

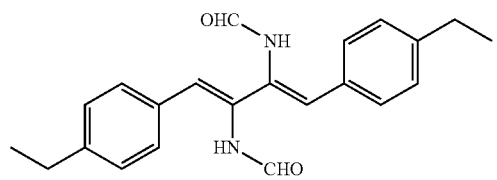 [SMILES: CCc1ccc(/C=C(NC=O)/C(=C/c2ccc(CC)cc2)NC=O)cc1]

Following the general method, the mentioned compound is obtained at a 20% yield (white solid), after 1 hour of reaction, using (E)-N-[2-(4-ethylphenyl)-1-(tributylstannyl)vinyl]formamide (1.50 g, 3.23 mmol) and CuCl (0.64 g, 6.46 mmol) as starting materials.

The purification described in the general method is varied: the reaction mixture is diluted with Me-THF (50 mL) and washed with an aqueous ammonia solution (10%, 30 mL×3). The organic phase is dried on anhydrous Na$_2$SO$_4$, filtered and concentrated to dryness, obtaining a white solid which is ground with MeOH and with Et$_2$O.

$^1$H-NMR (DMSO-d$_6$, 250 MHz) δ ppm: Rotamer mixture:

9.67-9.31 (m, 2H, CHO); [8.19 (s)+7.93-7.76 (m)] (2H, NH); 7.50-7.15 (m, 8H, ArH); 6.64-6.50 (m, 2H, alkene); 2.59 (q, J=6.7 Hz, 4H, CH$_2$); 1.17 (t, J=6.7 Hz, 6H, CH$_3$).

Compounds NPS0158, NPS0159, NPS0160, NPS0161 and NPS0163 are purified by means of forming a suspension in MeTHF, washed with aqueous ammonia, for removing copper residues. The organic suspension is subsequently concentrated and ground with alcohol (MeOH or EtOH) and with Et$_2$O, obtaining the final compounds as very pure white solids (>95%).

EXAMPLE 10

Protective Effect of the Cell Death of the Analogues NPS0158 (G+G), NPS0159 (F+F), NPS0160 (P+P) and NPS0161 (H+H)

Continuing with the study of the synthesized analogues, the researchers decided to analyze the neuroprotective effect thereof. The assays were performed on SK-N-MC human neuroblastoma culture cells, maintained as detailed in Example 2.

The inhibition of cell death by the compounds caused by treatment with xanthine/xanthine oxidase (XXO) which causes oxidative damage, which triggers cell death, was analyzed in real time. The assay was performed following the same method as the one described in Example 6, testing the analogues at 40, 100, 400 or 1000 ng/ml in the presence of XXO. The cells were incubated (at 37° C. and 5% CO$_2$) with these treatments for 72 hours, and was monitored every 10 minutes. The values that are obtained are arbitrary units indicated by cell index, calculated from the impedance data and used as a measurement of cell viability.

The results obtained for the analogues are shown in FIGS. 25-28 as the normalized cell index (A) of each condition analyzed throughout treatment; and as the percentage of cell death (B) for each treatment relating to death caused by XXO at 20 hours post-treatment. FIGS. 25, 26, 27 and 28 correspond respectively to the results of analogues NPS0158 (G+G), NPS0159 (F+F), NPS0160 (P+P) and NPS0161 (H+H). * indicates the significant difference with respect to treatment with XXO according to the Student's t test ($p<0.05$). Protection against death was observed for the four synthesized analogues, the maximum being 27% at 1000 ng/ml for NPS0158, 35% at 1000 ng/ml for NPS0159, 23% at 100 ng/ml for NPS0160 and 26% at 100 ng/ml for NPS0161. In summary, these analogues show a protective effect against human neuronal cell death caused by oxidative stress.

EXAMPLE 11

Antioxidant Effect of Analogues NPS0158 (G+G), NPS0159 (F+F), NPS0160 (P+P) and NPS0161 (H+H) in In Vitro and Cell Models 11.1. Antioxidant Effect of Analogues NPS0158 and NPS0159 In Vitro Based on the preceding results, the inventors decided to evaluate the in vitro antioxidant capacity of the synthesized analogues, using an antioxidant capacity measurement assay valid for lipophilic compounds, according to the ABTS*$^+$ method (Samaniego et al. 2007. *Analytica Chimica Acta* 593: 103-107). This method is based on forming the ABTS*$^+$ radical cation by means of oxidation with ammonium persulfate of the ABTS reagent [2,2'-azino-bis(3-ethylbenzothiazoline-6-sulfonic acid], which can be colorimetrically determined. In this assay, the compounds with antioxidant capacity suppress the oxidation of the radical in a concentration-dependent manner. A standard curve with increasing concentrations of trolox (hydrosoluble vitamin E analogue) is used to quantify antioxidant capacity, such that the results are indicated as a measurement of trolox equivalents (TE). The results obtained for analogues NPS0158 and NPS0159 are 174±13 μM TE and 165±44 μM TE, respectively, for 0.1 μg of each compound, so they show high in vitro antioxidant capacity.

Figure 29:
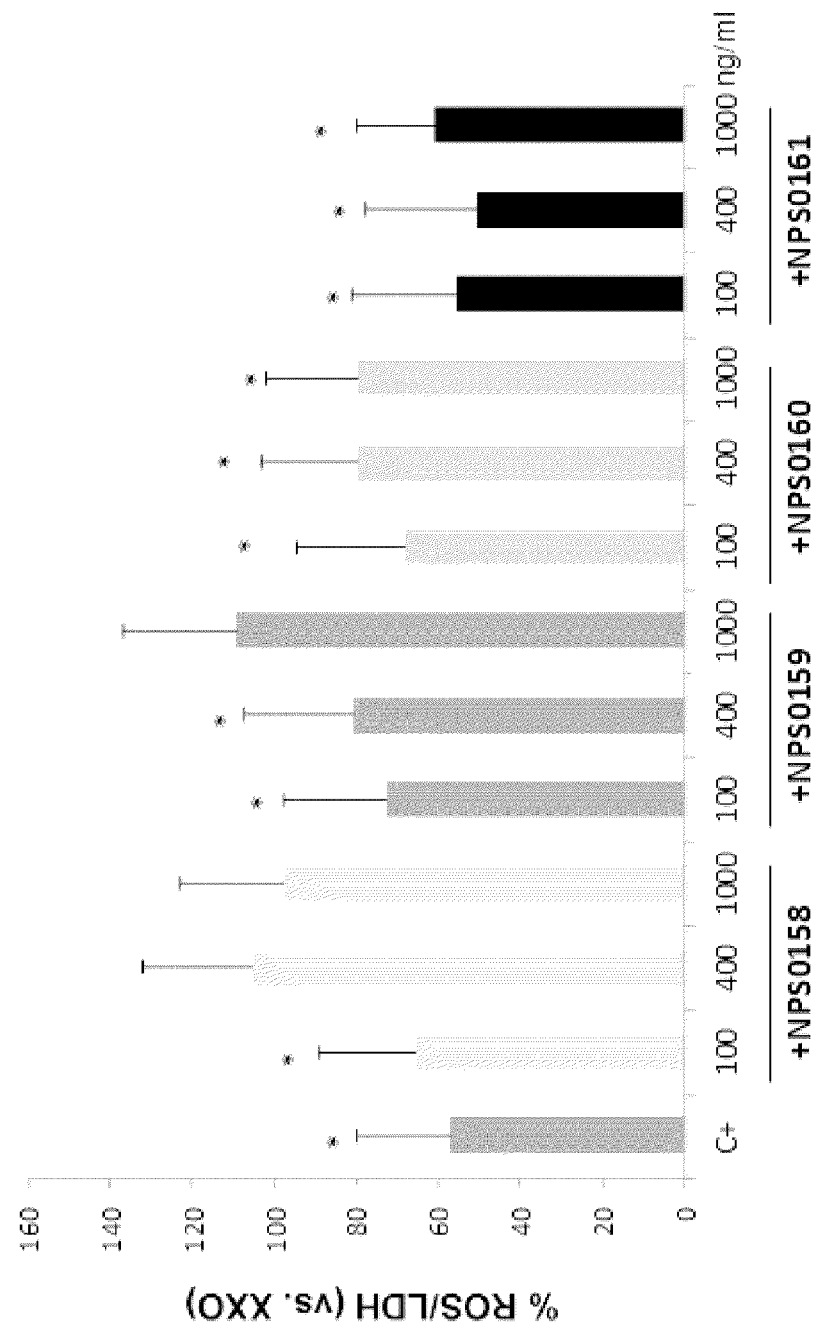
FIG. 29 shows the results obtained with analogues NPS0158, NPS0159, NPS0160 and NPS0161 on the production of Reactive Oxygen Species (ROS) corrected by LDH (lactate dehydrogenase activity), as a measurement of cell viability, with respect to treatment with XXO of each analogue in a dose-response curve. A compound known for ROS reduction control (C+) was used. The results are the mean±SD of four assays performed in sextuplicate. * is indicated for the significant difference with respect to treatment with XXO according to the Student's t test ($p<0.05$).

11.2. Reactive Oxygen Species (ROS) Reduction Capacity of Analogues NPS0158, NPS0159, NPS0160 and NPS0161 in a Cell Model Based on the preceding results, the inventors decided to evaluate the antioxidant capacity of the analogues in a cell model. The ROS measurement assay was performed on SK-N-MC human neuroblastoma culture cells, maintained as detailed in Example 2, subjected to aggression with xanthine/xanthine oxidase (XXO). The ROS measurement is taken by means of adding a permeable non-fluorescent probe in live cells (2',7'-dichlorodihydrofluorescein diacetate, $H_2DCFDA$; Biotium) which is oxidized by the action of ROS, generating 2',7'-dichlorofluorescein (DCF) which can be detected in a fluorometer at 485 nm of excitation and 538 nm of emission. The fluorescence results were normalized by cell viability, measured by means of lactate dehydrogenase (LDH) activity, using the Roche Cytotoxicity Detection Kit (LDH). The results obtained with the analogues on the production of ROS are shown in FIG. 29 as the percentage of ROS corrected by LDH with respect to treatment with XXO of each analogue in a dose-response curve. A known ROS reduction control compound (C+) was used. * indicates the significant difference with respect to treatment with XXO according to the Student's t test (p<0.05). ROS reduction was observed for the four synthesized analogues, the maximum being 34% at 100 ng/ml for NPS0158, 27% at 100 ng/ml for NPS0159, 31% at 100 ng/ml for NPS0160, 45% at 400 ng/ml for NPS0161. In conclusion, these analogues show antioxidant capacity in human neuronal cells.

EXAMPLE 12

Figure 30:
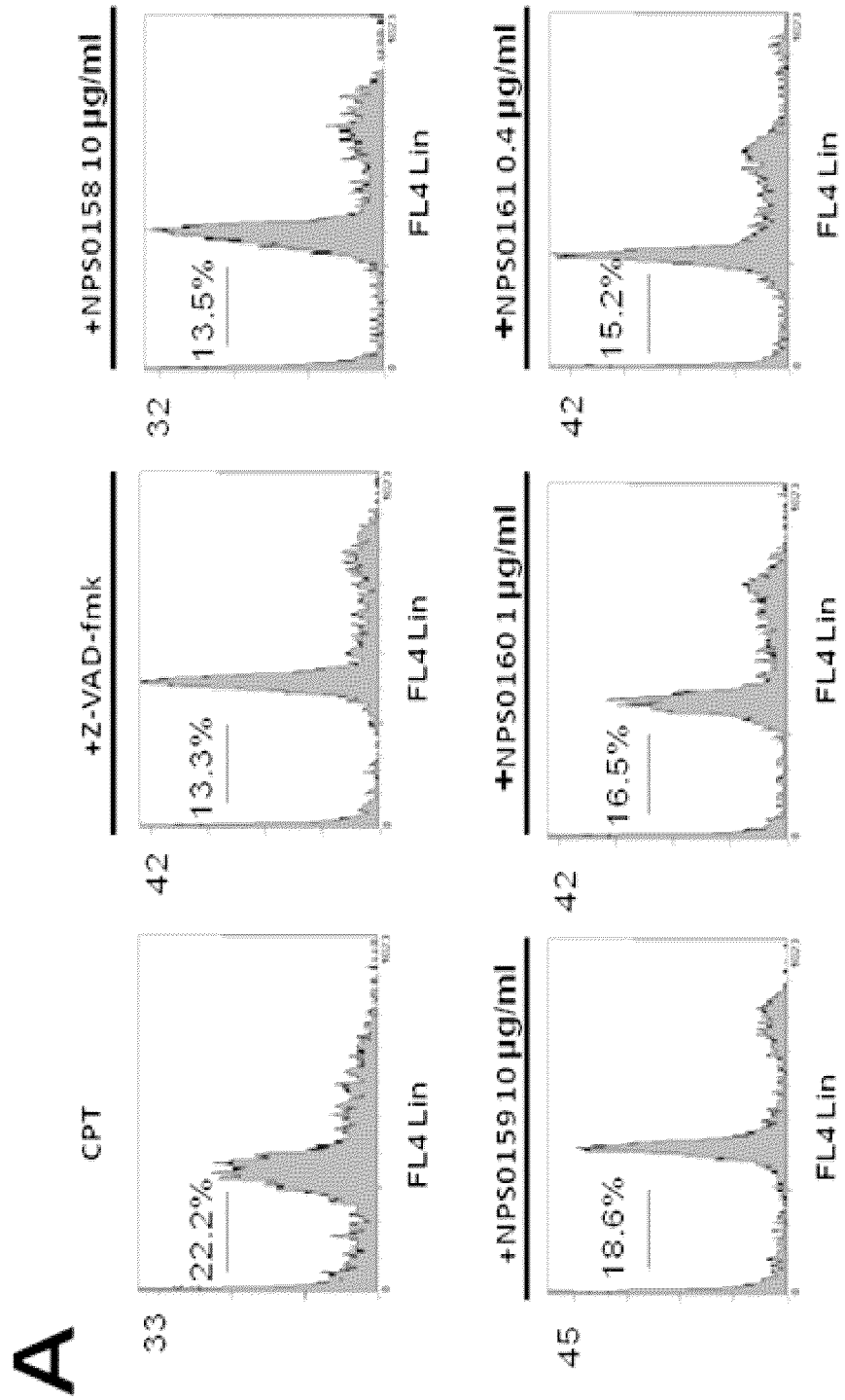
FIG. 30 shows in (A) the flow cytometry analysis of propidium iodide fluorescence with respect to the amount of DNA for SK-N-MC cells pre-treated for 24 hours with NPS0158 and NPS0159 at 10 μg/ml, NPS0160 at 1 μg/ml and NPS0161 at 0.4 μg/ml followed by treatment with 50 μM camptothecin (CPT) for 6 hours (the indicated percentage of apoptosis is measured on the sub-G1 region of each of the conditions); and in (B) the representative histograms showing the percentage of DNA fragmentation relating to SK-N-MC cells treated with CPT. Z-VAD-fmk is used as a commercial inhibitor of apoptosis. The results represent the means±SD of two independent experiments in quadruplicate. * Significant difference with respect to treatment with CPT according to the Student's t test ($p<0.05$).
Figure 30:
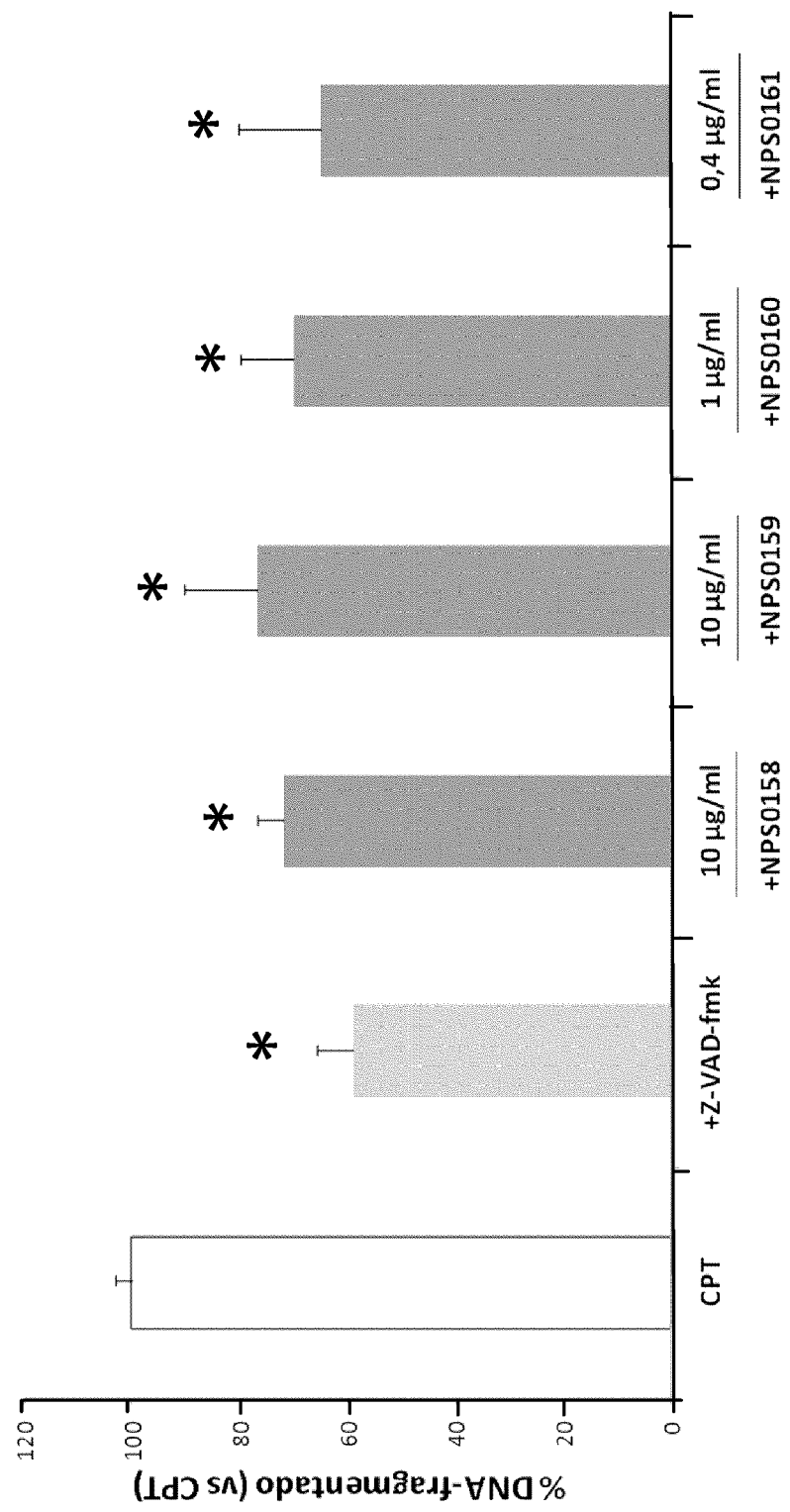

Antiapoptotic Effect of Analogues NPS0158 (G+G), NPS0159 (F+F), NPS0160 (P+P) and NPS0161 (H+H) in a Cell Model Continuing with the study, the researchers decided to analyze the antiapoptotic effect of the synthesized analogues by analyzing cellular DNA fragmentation by means of flow cytometry. The cellular fragmentation measurement assay was performed on SK-N-MC human neuroblastoma culture cells, maintained as detailed in Example 2, and subjected to an aggression with camptothecin (CPT), following the same approach as the one described in Example 8. Z-VAD-fmk at 50 μM is used as a commercial inhibitor of apoptosis. The obtained results show protection against apoptosis with NPS0158 between 1 and 10 μg/ml, the maximum being at 10 μg/ml (28%); the maximum of 23% with NPS0159 at 10 μg/ml; the maximum of 30% with NPS0160 at 1 μg/ml and the maximum of 35% with NPS0161 at 0.1 μg/ml. FIG. 30 includes the representative histograms of an assay showing the percentage of apoptosis in the sub-G1 region of each of the conditions. In conclusion, a protective effect against apoptosis in human neuronal cells is observed with the synthesized analogues.

EXAMPLE 13

Passive Permeability of Analogues NPS0158 (G+G) and NPS0161 (H+H): Prediction of the Theoretical and In Vitro Blood-Brain Barrier Crossing The researchers then decided to study the permeability of the blood-brain barrier (BBB) with respect to synthesized analogues by means of two methods: one theoretical method using the approach of Rishton et al. (Rishton et al. 2006. *Curr Opin Drug Disc & Dev*, 9[3]: 303) and another in vitro method by means of the PAMPA (Parallel Artificial Membrane Permeability Assay) assay which mimics the BBB by means of a system including a mixture of brain lipids very similar to the mixture existing in the human BBB, following the recommendations of Avdeef et al. (Avdeef et al. 2007. *Journal of Pharmaceutical Sciences* 96 [11]: 2893-2909).

13.1. Prediction of the Theoretical Blood-Brain Barrier Crossing

The Rishton equation was used to determine the theoretical barrier crossing because this formula takes into account the c Log P (octanol/water partition coefficient) and PSA (polar surface area) parameters to obtain the log BB value, which is defined as the logarithm value of brain to plasma concentration ratio. The calculation of said parameter for the synthesized analogue NPS0158 is 0.34 and 0.44 for NPS0161, which indicates that both compounds theoretically cross the barrier (values between 0 and 0.5 would indicate barrier crossing).

13.2. Prediction of the Blood-Brain Barrier Crossing In Vitro

A mixture of lipids derived from pig brain, with a phospholipid composition very similar to the composition forming the human BBB, and referred to as PBL (Porcine Polar Brain Lipid, Avanti Polar Lipids Inc) which is prepared in microtiter plates with a MAIPNTR10 filter (Millipore), with a PVDF membrane and pore size of 45 μm, was used to mimic the blood-brain barrier. 20% methanol is added to the assay buffer (28 mM $KH_2PO_4$, 41 mM $Na_2HPO_4$) to assure the solubility of the compounds. Two assay controls were used in this system; a compound that crosses the BBB (verapamil) and another compound that does not cross the barrier (theophylline). The compounds under study were maintained for 4 hours in the system after which they were measured in a spectrophotometer at a wavelength of 335 nm for compounds NPS0158 and NPS0161 and at 278 nm for the control compounds. The percentage of barrier crossing and the effective permeability (Pe) were calculated based on the absorbance data obtained. The following formula was applied to calculate the Pe:

$$P_e \approx -\frac{2.3 V_D}{A \cdot t} \cdot \log_{10}\left(\frac{1}{1-R} \cdot \frac{C_D(t)}{C_D(t=0)}\right)$$

Where
$V_D$=donor volume ($cm^3$)
A=filter area ($cm^2$)
t=assay time
R=parts per unit of retention
$C_D(t)$=donor concentration
$C_D(t=0)$=concentration of the original The results obtained in the model show that verapamil has a $P_e$ value=$1.53 \times 10^{-5}$ cm/s and a percentage of permeability of 38% and theophylline a $P_e$=$-6.16 \times 10^{-6}$ cm/s and a percentage of permeability of 2%. $P_e$ values above $4 \times 10^{-6}$ cm/s indicate elevated permeability, and $P_e$ values under $2 \times 10^{-6}$ cm/s or negative values indicate low permeability, so the results of the controls validate the quality of the membrane for the assay. The obtained results show a $P_e$ value for NPS0158 equal to $5.19 \times 10^{-6}$ cm/s and a percentage of permeability of 13% and for NPS0161 at $P_e$ equal to $1.47 \times 10^{-5}$ cm/s and a percentage of permeability of the 29%. In conclusion, a high BBB permeability of NPS0161 and a moderate permeability of NPS0158 are obtained.

What is claimed is:

1. A method for inhibiting neuronal cell death caused by oxidative stress, wherein the diseases treatable by said inhibition are selected from Alzheimer's disease, mild cognitive impairment, Huntington's disease, Parkinson's disease, Creutzfeldt-Jakob disease, amyotrophic lateral sclerosis (ALS) and multiple sclerosis (MS), as well as progeria, the method comprising:

administering to a patient needing such treatment a therapeutically effective amount of at least a compound of formula (I):

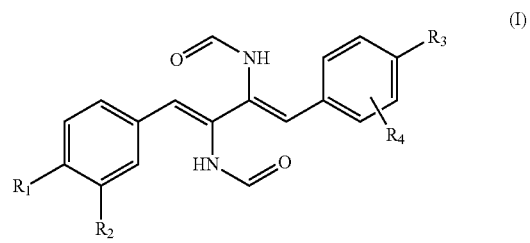

where:
R₁ is selected from alkyl, OH, O-alkyl, SH, S-alkyl, NH₂, NH-alkyl, N(alkyl)₂ and halogen,
R₂, R₃ and R₄ are selected independently from hydrogen, alkyl, OH, O-alkyl, SH, S-alkyl, NH₂, NH-alkyl, N(alkyl)₂ and halogen,
or R₁ and R₂ and/or R₃ and R₄ form an —O-alkylene-O— group,
or a pharmaceutically acceptable salt or solvate thereof.

2. The method according to claim 1, wherein the disease is Alzheimer's disease.

3. The method according to claim 1, wherein R₁ is selected from alkyl, OH and O-alkyl, or R₁ is bound to R₂ forming an —O-alkylene-O group.

4. The method according to claim 1, wherein R₂, R₃ and R₄ are selected independently from hydrogen, alkyl, OH and O-alkyl, or R₂ is bound to R₁ forming an —O-alkylene-O group, and/or R₃ and R₄ are bound to one another forming an —O-alkylene-O group.

5. The method according to claim 1, wherein R₄ is in the meta position of the aromatic ring relative to the C=C double bond.

6. The method according to claim 1, wherein R₁ is OH, methoxy, ethoxy, ethyl, methyl or forms, together with R₂, an —O-alkylene-O group.

7. The method according to claim 1, wherein R₂ is hydrogen, OH, ethyl, methyl or forms, together with R₁, an —O-alkylene-O group.

8. The method according to claim 1, wherein R₃ is OH, ethyl, methyl or forms, together with R₄, an —O-alkylene-O group.

9. The method according to claim 1, wherein R₄ is hydrogen, OH, ethyl, methyl or forms, together with R₃, an —O-alkylene-O group.

10. The method according to claim 1, wherein the compound of formula (I) is selected from the following compounds:

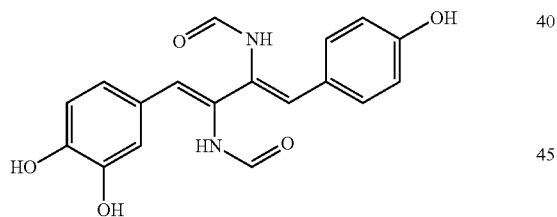

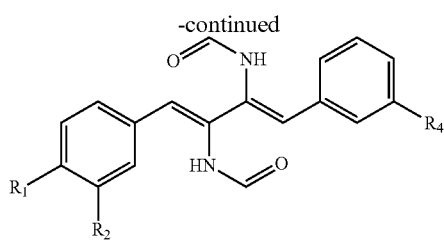

R₁ = R₂ = R₄ = Me, Et

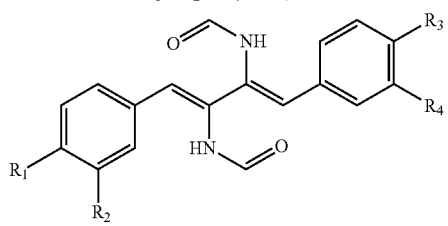

R₁ = R₂ = R₃ = R₄ = Me, Et

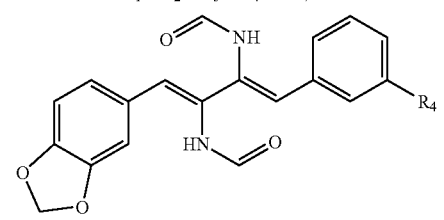

R₄ = OH, Me, Et

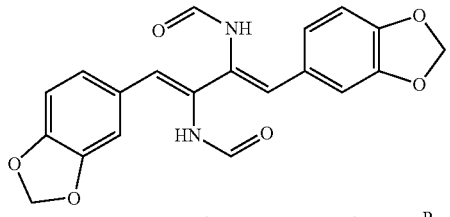

R₁ = R₃ = OH, Me, Et, OEt

* * * * *

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: NL1 primer

<400> SEQUENCE: 1
gcatatcaat aagcggagga aaag                                         24

<210> SEQ ID NO 2
<211> LENGTH: 19
<212> TYPE: DNA
<213> ORGANISM: Artificial Sequence
<220> FEATURE:
<223> OTHER INFORMATION: NL4 primer

<400> SEQUENCE: 2
ggtccgtgtt tcaagacgg                                               19

<210> SEQ ID NO 3
<211> LENGTH: 564
<212> TYPE: DNA
<213> ORGANISM: Artificial Sequence
<220> FEATURE:
<223> OTHER INFORMATION: 28S gene fragment

<400> SEQUENCE: 3
cccgcgtccg agccgagcgc gttcctcggt ctaggcaggt cgcattgcac cctcggctat    60
aagacgcccc tagggggcgtt accttccgag ggcctttgac cgaccgccca aaccgacgct   120
ggcccgcccg cggggaagta caccggcacg aatgccggct gaaccccgcg agcgagtctg   180
gtcgcaagcg cttcccttc aacaatttca cgtgcttttt aactctcttt tcaaagtgct    240
tttcatcttt cgatcactct acttgtgcgc tatcggtctc cggccaatat ttagctttag   300
atgaaattta ccacccattt agagctgcat tcccaaacaa ctcgactcgt cgaaggagct   360
tcacacgggc gcggacaccc catcccatac gggattctca ccctctatga cgtcccgttc   420
cagggcactt agatggggac cgctcccgaa gcatcctcta caaattacaa tgcggacccc   480
gaaggagcca gctttcaaat ttgagctctt gccgcttcac tcgccgttac tggggcaatc   540
cctgttggtt tcttttcctc cgct                                         564